(12) United States Patent
Baum et al.

(10) Patent No.: US 8,796,026 B2
(45) Date of Patent: Aug. 5, 2014

(54) **INSECTICIDAL PROTEINS SECRETED FROM *BACILLUS THURINGIENSIS* AND USES THEREFOR**

(75) Inventors: James A. Baum, Webster Groves, MO (US); Judith C. Donovan, Manchester, MO (US); William P. Donovan, Manchester, MO (US); James T. Engleman, Ephrata, PA (US); Karina Krasomil-Osterfeld, Ellisville, MO (US); John W. Pitkin, Wildwood, MO (US); James K. Roberts, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 1441 days.

(21) Appl. No.: 10/563,270

(22) PCT Filed: Jul. 6, 2004

(86) PCT No.: PCT/US2004/021692
§ 371 (c)(1),
(2), (4) Date: May 2, 2006

(87) PCT Pub. No.: WO2005/019414
PCT Pub. Date: Mar. 3, 2005

(65) Prior Publication Data
US 2006/0191034 A1   Aug. 24, 2006

Related U.S. Application Data

(60) Provisional application No. 60/485,483, filed on Jul. 7, 2003.

(51) Int. Cl.
*C12N 15/82* (2006.01)
*C12N 15/32* (2006.01)

(52) U.S. Cl.
USPC .................. 435/418; 536/23.71; 435/6.11

(58) Field of Classification Search
None
See application file for complete search history.

(56) References Cited

U.S. PATENT DOCUMENTS

| | | | | | |
|---|---|---|---|---|---|
| 5,024,837 | A | * | 6/1991 | Donovan et al. | 424/93.2 |
| 5,308,760 | A | * | 5/1994 | Brown et al. | 435/69.1 |
| 5,573,766 | A | * | 11/1996 | Blenk et al. | 424/93.461 |
| 5,608,142 | A | * | 3/1997 | Barton et al. | 800/302 |

FOREIGN PATENT DOCUMENTS

| | | |
|---|---|---|
| EP | 0451878 A1 | 10/1991 |
| WO | 8808880 A1 | 11/1988 |

OTHER PUBLICATIONS

Donovan et al (1988, Mol. Gen. Genet. 214:365-372.*
Chan et al., Unusual Amino Acid Determinants of Host Range in the Mtx2 Family of Mosquitocidal Toxins, *The Journal of Biological Chemistry* 271:14183-14187 (1996).
Donovan et al., Discovery and characterization if Sip1A: a novel secreted protein from *Bacillus thuringiensis* with activity against coleopteran larvae, *Appl. Microbiol. Biotechnol* 72:713-719 (2006).
Lambert et al., Novel *Bacillus thuringiensis* Insecticidal Crystal Protein with a Silent Activity against Coleopteran Larvae, *Applied and Environmental Microbiology* 58:2536-2542 (1992).
Berry et al., Complete Sequence and Organization of pBtoxis, the Toxin-Coding Plasmid of *Bacillus thuringiensis* subsp. *Israelensis*, *Applied and Environmental Microbiology* 68:5082-5095 (2002).
Hwang et al., A Novel Class of Mosquitocidal δ-Endotoxin, Cry19B, Encoded by a *Bacillus thuringiensis* serovar *higo* Gene, *System. App. Microbiol.* 21:179-184 (1998).
Donovan et al. (1988) Molecular & General Genetics 214:365-372; Isolation and characterization of EG2158, a new strain of *Bacillus thuringiensis* toxic to coleopteran larvae, and nucleotide sequence of the toxin gene.

* cited by examiner

*Primary Examiner* — Anne Kubelik
(74) *Attorney, Agent, or Firm* — Thompson Coburn LLP; J. Wendy Davis

(57) ABSTRACT

The present invention relates to the isolation and characterization of nucleotide sequences encoding novel insecticidal proteins secreted into the extracellular space from *Bacillus thuringiensis* and related strains. The proteins are isolated from culture supernatants of *Bacillus thuringiensis* and related strains and display insecticidal activity against coleopteran insects including Colorado potato beetle (*Lymantria dispar*) and Southern Corn Rootworm (*Diabrotica undecempunctata*). Insecticidal proteins encoded by nucleotide sequences that hybridize to the isolated and characterized nucleotide sequences are disclosed. Also disclosed are methods of making and using transgenic cells and plants comprising the novel nucleotide sequence of the invention.

11 Claims, 3 Drawing Sheets

Figure 1B

```
                          330              340              350
                    |....|....|....|....|....|....|....|....|....|
SEQ ID NO:4   321   NGETLYIHDTPAKFMFNGANPYYRATFTEYDGNNNPV         TIC901
SEQ ID NO:6   321   NGDTLYIHDTPAKFIHFNGANPYYRATFTEYDENKPV         TIC1201
SEQ ID NO:8   321   NGDTLYIHETPAKFHTFNGANPYYRATFTEYDDKDG          TIC407
SEQ ID NO:10  321   NGDTLYIHDTPAKFTLNGGNPYYTATFTEYDENGN           TIC417
SEQ ID NO:33  321   NGDTLYIHDTPAKFTFNGANPYYRATFTEYDENG            TIC431p
                    |....|....|....|....|....|....|....|....|....|  Consensus SEQ ID NO:4   360   VLSENFKL   367                               TIC901 p
SEQ ID NO:6   360   ILSGN      364                               TIC1201p
SEQ ID NO:8   361   FLSENYKKL  368                               TIC407p
SEQ ID NO:10  360   RL-NN-     364                               TIC417p
SEQ ID NO:33  360   HLSV-      364                               TIC431p
                    XLSEN-KL                                     Consensus
```

Figure 1c

INSECTICIDAL PROTEINS SECRETED FROM BACILLUS THURINGIENSIS AND USES THEREFOR

CROSS REFERENCE TO RELATED APPLICATIONS

This application is filed under 35 USC §371 from the international application No. PCT/US2004/021692 filed Jul. 6, 2004, which claims the benefit of priority from U.S. Provisional Patent Application Ser. No. 60/485,483 filed Jul. 7, 2003.

FIELD OF THE INVENTION

The present invention relates to a new family of nucleotide sequences encoding insecticidal proteins and insecticidal fragments thereof. In particular, the present invention is directed to exemplary proteins designated herein as TIC901, TIC1201, TIC407, TIC417, and, TIC431 and insecticidal fragments thereof, each encoded by the exemplary nucleotide coding sequences designated herein respectively as tic901, tic1201, tic407, tic417, and tic431, as well as to nucleotide sequence homologs that (1) encode insecticidal proteins and (2) hybridize to the tic901, tic1201, tic407, tic417, and tic431 coding sequences under hybridization conditions selected from the group consisting of stringent hybridization conditions and specific hybridization conditions. The present invention also relates to host cells transformed with the nucleotide sequences of the present invention or transformed with variant nucleotide sequences based on the tic901 gene, related genes, and/or homologs thereof, particularly those sequences that have been modified for improved expression in plants. In a preferred embodiment, the transformed host cells are plant cells.

BACKGROUND OF THE INVENTION

*Bacillus thuringiensis* is a gram-positive bacterium that produces proteinaceous crystalline inclusions during sporulation. These *B. thuringiensis* crystal proteins are often highly toxic to specific insects. Insecticidal activities have been identified for crystal proteins from various *B. thuringiensis* strains against insect larvae from the insect orders Lepidoptera (caterpillars), Diptera (mosquitoes, flies) and Coleoptera (beetles).

Individual *B. thuringiensis* crystal proteins, also called delta-endotoxins or parasporal crystals or toxin proteins, can differ extensively in their structure and insecticidal activities. These insecticidal proteins are encoded by genes typically located on large plasmids, greater than 30 mega Daltons (MDa) in size, that are found in *B. thuringiensis* strains. A number of *B. thuringiensis* toxin genes have been cloned and the insecticidal crystal protein products characterized for their specific insecticidal properties. Reviews of *B. thuringiensis* toxin genes and crystal proteins are available (for example, Höfte et al., 1989; Schnepf et al., 1998).

The insecticidal properties of *B. thuringiensis* have been long recognized, and *B. thuringiensis* strains have been incorporated in commercial biological insecticide products for over forty years. Commercial *B. thuringiensis* insecticide formulations typically contain dried sporulated *B. thuringiensis* fermentation cultures whose crystal proteins are toxic to various insect species.

Traditional commercial *B. thuringiensis* bio-insecticide products are derived from "wild-type" *B. thuringiensis* strains, i.e., purified cultures of *B. thuringiensis* strains isolated from natural sources. Newer commercial *B. thuringiensis* bio-insecticide products are based on genetically altered *B. thuringiensis* strains, such as the transconjugant *B. thuringiensis* strains described in U.S. Pat. Nos. 5,080,897 and 4,935,353.

Various *B. thuringiensis* strains have been classified based on the reactions of the *B. thuringiensis* flagella with antibodies. A *B. thuringiensis* strain whose flagella react with a unique antibody is classified as a unique serovar, and over thirty different *B. thuringiensis* serovars or subspecies have been described (DeBarjac and Frachon, 1990).

Each *B. thuringiensis* subspecies *often* produces unique types of insecticidal crystal proteins. For example, *B. thuringiensis* subspecies *kurstaki* produces crystal proteins of approximately 130 kilo Daltons (kD) and 70 kD in size that are toxic to caterpillars, whereas *B. thuringiensis* subspecies *tezebriottis* produces a crystal protein of about 72 kD which is toxic to beetles.

A characteristic of crystal proteins is their ability to coalesce to form crystals inside the *B. thuringiensis* mother cell. Upon lysis of the mother cell the proteins are released as crystals into the external environment. In addition, *B. thuringiensis* also produces non-crystal proteins that, in contrast to crystal proteins, are secreted by *B. thuringiensis* cells as soluble proteins into the culture medium. Secreted non-crystal proteins of *B. thuringiensis* include phospholipases, proteases, and β-lactamase that have little, if any, insecticidal activity. However, three secreted non-crystal proteins of *B. thuringiensis* designated Vip1, Vip2 and Vip3 have been reported to be toxic to coleopteran or lepidopteran insects (Estruch et al., 1996; U.S. Pat. No. 5,866,326; WO94/21795; WO96/10083). A non-crystal protein of *B. thuringiensis* designated CryV is reported to be toxic to lepidopteran insects (Kostichka et al., 1996). A number of *Bacillus thuringiensis* isolates producing extracellular secreted insecticidal protein toxins have been previously identified (U.S. Pat. No. 5,840,868; U.S. Pat. No. 5,849,870; U.S. Pat. No. 5,866,326; U.S. Pat. No. 5,872,212; U.S. Pat. No. 5,877,012; U.S. Pat. No. 5,888,801; U.S. Pat. No. 6,204,435; U.S. Pat. No. 6,242,669; U.S. Pat. No. 6,279,369). Such strains have all been shown to produce one or more of these VIP or CryV toxin proteins or closely related homologs. Surprisingly, the inventors herein disclose a new class of extracellular secreted insecticidal protein toxins that do not exhibit homology to the known VIP or CryV classes of proteins.

Comparisons of amino acid sequences indicate that the Vip1, Vip2, Vip3, WAR, MIS and CryV protein classes are not related to the proteins of the present invention. Further comparison shows that none of the one hundred thirty-seven, more or less, known insect-toxic proteins of *B. thuringiensis* (Crickmore et al., 1998), are related to the proteins of the present invention. In fact, no significant homology was found between the sequences of the proteins of the present invention and any of the thousands of protein sequences contained in the National Center for Genome Resources (GenBank), Santa Fe, N. Mex. A BLAST search identified only two proteins in the GenBank database that suggested a possible homology to TIC901. The *Bacillus sphaericus* Mtx2 insecticidal protein exhibited only a 21% amino acid sequence identity over a contiguous 135 amino acid sequence length when aligned with TIC901. A putative amino acid sequence that may be expressed from a Fowlpox virus genome exhibited only a 27% amino acid sequence identity over a contiguous 147 amino acid sequence length when aligned with TIC901.

SUMMARY OF THE INVENTION

In one embodiment, the present invention relates to an isolated and purified insecticidal protein, exhibiting an amino acid sequence substantially as set forth in SEQ ID NO: 4, SEQ ID NO:6, SEQ ID NO:8, SEQ ID NO:10, and SEQ ID NO:33 whether as precursor amino acid sequences or mature and/or processed and secreted forms of these amino acid sequences, or related amino acid sequences and homologs thereof. Insecticidal activity of TIC901 and related proteins has been demonstrated in bioassays with Colorado Potato Beetle (CPB), and with Western and Southern Corn Rootworms. In particular the proteins are toxic to coleopteran insects including Colorado potato beetle (*Lymantria dispar*) and Corn Rootworms (CRW), as shown herein.

In another embodiment, the present invention also relates to an isolated and purified nucleotide sequence, i.e. a coding sequence, comprising a nucleotide sequence as set forth in SEQ ID NO:3, SEQ ID NO:5, SEQ ID NO:7, SEQ ID NO:9, and/or SEQ ID NO:32, and related sequences or homologs thereof. The native or wild-type tic901 coding sequence as set forth in SEQ ID NO:3 encodes the native TIC901 precursor, preprotein, or pretoxin protein exhibiting the amino acid sequence as set forth in SEQ ID NO:4. Organisms producing TIC901 protein exhibit insecticidal activity and/or insect-resistance properties. An insecticidal amino acid sequence corresponding to the protein localized to the extracellular space surrounding a *Bacillus* cell expressing the protein from SEQ ID NO:3 corresponds to a protein comprising from about amino acid position 44 through about amino acid position 367 as set forth in SEQ ID NO:4. The native or wild type tic1201 coding sequence as set forth in SEQ ID NO:5 encodes the TIC1201 precursor protein exhibiting the amino acid sequence as set forth in SEQ ID NO:6. An insecticidal amino acid sequence corresponding to the protein localized to the extracellular space surrounding a *Bacillus* cell expressing the protein from SEQ ID NO:5 corresponds to a mature protein comprising from about amino acid position 44 through about amino acid position 364 as set forth in SEQ ID NO:6. The native or wild type tic407 coding sequence as set forth in SEQ ID NO:7 encodes the TIC407 precursor, preprotein, or pretoxin protein exhibiting the amino acid sequence as set forth in SEQ ID NO:8. An insecticidal amino acid sequence corresponding to the mature protein localized to the extracellular space surrounding a *Bacillus* cell expressing the protein from SEQ ID NO:7 corresponds to a protein comprising from about amino acid position 44 through about amino acid position 367 as set forth in SEQ ID NO:8. The native or wild-type tic417 coding sequence as set forth in SEQ ID NO:9 encodes the TIC417 precursor, preprotein, or pretoxin protein exhibiting the amino acid sequence as set forth in SEQ ID NO:10. An insecticidal amino acid sequence corresponding to the mature protein localized to the extracellular space surrounding a *Bacillus* cell expressing the protein from SEQ ID NO:9 corresponds to a protein comprising from about amino acid position 44 through about amino acid position 364 as set forth in SEQ ID NO:10. The native or wild type tic431 coding sequence as set forth in SEQ ID NO:32 encodes a TIC431 precursor, preprotein, or pretoxin protein exhibiting an amino acid sequence as set forth in SEQ ID NO:33. An insecticidal amino acid sequence corresponding to a mature protein localized to the extracellular space surrounding a *Bacillus thuringiensis* cell expressing the protein from SEQ ID NO:33 corresponds to a protein comprising from about amino acid 44 through about amino acid 364 as set forth in SEQ ID NO:33. Nucleotide sequence homologs, i.e., insecticidal proteins encoded by nucleotide sequences that hybridize to each or any of the sequences disclosed herein under stringent hybridization conditions, are specifically intended to be included within the scope of the present invention.

In a further embodiment, the present invention relates to a biologically pure culture of a *Bacillus thuringiensis* bacterium transformed with a plasmid vector containing a nucleotide sequence as set forth in SEQ ID NO:3, SEQ ID NO:5, SEQ ID NO:7, SEQ ID NO:9, and/or SEQ ID NO:32, and or related sequences or homologs that produces an insecticidal protein and secretes the protein into the extracellular space surrounding the bacterial strain during fermentation. An exemplary strain EG12450 has been deposited in a permanent culture collection pursuant to the Budapest Treaty and has been assigned the accession No. NRRL B-30357.

In a further embodiment, the invention also relates to a biologically pure culture of a *B. thuringiensis* bacterium designated as strain EG2158 exhibiting insecticidal activity against coleopteran insects. *B. thuringiensis* strain EG2158 represents a wild type *B. thuringiensis* strain from which a tic901 coding sequence was isolated and has been deposited in a permanent culture collection pursuant to the Budapest Treaty and has been assigned the accession No. NRRL B-18213. EG2158 is shown herein to produce at least two insecticidal proteins comprising the amino acid sequences selected from the group consisting of SEQ ID NO:4 and SEQ ID NO:10.

In a further embodiment, the present invention provides a vector comprising a nucleotide sequence as set forth in SEQ ID NO:3 encoding a TIC901 amino acid sequence as set forth in SEQ ID NO:4. An *Escherichia coli* strain containing a vector comprising SEQ ID NO:3 has been deposited on Feb. 6, 2002 in the Northern Regional Research Lab of Agricultural Research Service Center Collection (NRRL), USDA, under the provisions of the "Budapest Treaty on the International Recognition of the Deposit of Microorganism for the Purposes of Patent Procedure" and given the Accession No. NRRL B-30549. One plasmid containing said nucleotide sequence is set forth herein as pEG1381.

In a further embodiment, the present invention provides a nucleotide sequence as set forth in SEQ ID NO:3 encoding a TIC901 amino acid sequence, and an oligonucleotide portion that can be labeled and used as a hybridization probe for identifying additional related genes encoding related insecticidal proteins or homologues thereof. Other related nucleotide sequences specifically exemplified herein comprise sequences as set forth in SEQ ID NO:5, SEQ ID NO:7, SEQ ID NO:9, and SEQ ID NO:32, each of which encode insecticidal protein toxins as set forth in SEQ ID NO: 4, SEQ ID NO:6, SEQ ID NO:8, SEQ ID NO:10, and SEQ ID NO:33, respectively.

In yet a further embodiment, the invention provides plant cells and plants that have been transformed with a nucleotide sequence encoding a TIC901 protein as set forth in SEQ ID NO:4 or an insecticidal fragment thereof. The nucleotide sequence can be translated and expressed by plant cells and in plant tissues at levels sufficient to inhibit or kill Coleopteran insect pests. Both monocot and dicot plants are within the scope of the invention. Modification of the sequence may be required in order to effect the maximum level of expression and to enhance the ability of the plant containing the sequence to produce insecticidal levels of the TIC901 protein.

In yet a further embodiment, the present invention also provides a method for producing a transgenic plant that exhibits increased expression levels of a nucleotide sequence encoding TIC901, and thereafter increased levels of the insecticidal protein TIC901. Thus plants transformed with nucleotide sequences modified from those disclosed herein exhibit improved and increased levels of coleopteran pest resistance abilities in comparison to a plant lacking a nucleotide sequence encoding a TIC901 or related protein.

In accomplishing the foregoing, a method for expressing a nucleotide sequence encoding a TIC901 protein in a plant is provided comprising the steps of inserting into the genome of a plant cell a nucleic acid sequence comprising in the 5' to 3' direction, a plant functional promoter operably linked to a structural DNA sequence optimized for plant expression that causes production of an RNA sequence encoding a TIC901 polypeptide sequence as set forth in SEQ ID NO: 4, or a sequence having at least from about 80%, or from at least about 85%, or from at least about 90%, or from at least about 95%, or from at least about 99% sequence identity to the amino acid sequence as set forth in SEQ ID NO: 4; and a 3' non-translated DNA sequence that functions in the cells of the plant to cause transcription termination and polyadenylation; obtaining transformed plant cells containing said nucleic acid sequence; and regenerating from the transformed plant cells genetically transformed plants that express the nucleotide sequence encoding the TIC901 protein, wherein the transformed plants are morphologically normal and exhibit elevated or improved levels of coleopteran pest resistance compared to a plant not transformed to express said protein.

Another embodiment of the present invention is the provision for antibodies that bind specifically to epitopes presented only by the TIC901 protein or homologs. Antibodies can be used for identifying the presence of a TIC901 protein or homolog, for purifying said protein or homolog, for identifying a nucleotide sequence from which a TIC901 protein or homolog is being expressed, and for use in kits designed to allow the detection of a TIC901 protein or homolog or the detection of a nucleotide sequence expressing said protein or homolog.

A particular advantage of the present invention comprises an improvement in insect resistance management. The ability to combine two or more insecticidal agents, each toxic to the same insect pest species, into a single composition, and each agent exhibiting a mode of action different from the other insecticidal agents with which it is combined, present a means for more effectively controlling a particular insect pest species by substantially reducing the likelihood that resistance to the insecticidal composition will develop in a population. The TIC901 protein of the present invention can be combined with any number of known insectidical agents to achieve the level of resistance management in a particular composition, preferably by expression of the combination of insecticidal agents in plants. In particular TIC901 protein compositions can be combined with Cry3 or Cry3 amino acid sequence variants to achieve control of various coleopteran plant pest species, or with other appropriate Cry proteins such as PS149B1, CryET33/34, CryET80176, CryET70, Cry22, CryET39, CryET76, Cry5Ba, Cry6a, and Cry12a, and the like, and with VIP, WAR, or MIS proteins and the like, and with various insecticidal compositions derived from *Xenorhabdus* and *Photorhabdus* bacterium species that have been shown to exhibit insecticidal bioactivity directed to Coleopteran plant pest species. Preferably the in planta use of these compositions would be directed to enhanced expression of the proteins in the parts of the plant that exhibit the greatest vulnerability to coleopteran insect predation. For protection of potato against CPB, it would be preferable to achieve the highest levels of expression in the leaves and stems of the plant. For maize species susceptible to wireworm and to rootworms, it would be preferable to achieve the highest levels of expression in the subterranean parts of the plant, i.e., within the root systems of the plant.

Another embodiment comprises an isolated polynucleotide that encodes a *Bacillus thuringiensis* insecticidal toxin or insecticidal fragment thereof, active against an insect pest, wherein the toxin or insecticidal fragment has a molecular weight between approximately 36,000 Daltons and approximately 42,500 Daltons. In addition, the nucleotide sequence encoding the toxin, or the complement thereof, hybridizes under stringent conditions to SEQ ID NO:3. The toxin preferably exhibits biological activity in controlling or killing a coleopteran insect pest, preferably Colorado potato beetle and/or corn rootworms. In one embodiment the nucleotide sequence encoding the toxin is optimized for expression in plants, yet encodes substantially the toxin or an insecticidal fragment thereof, i.e., encodes the same or substantially the same amino acid sequence as present in the native amino acid sequence.

Another embodiment of the present invention provides for host cells transformed to contain a polynucleotide encoding an insecticidal protein of the present invention or an insecticidal fragment thereof. Preferably the nucleotide sequences of the present invention are modified to improve expression of the proteins of the present invention in a preferred host cell. The host cell of the present invention is selected from the group consisting of a bacterial cell, a fungal cell, and a plant cell. Expression in a plant cell can comprise expression to achieve accumulation of the insecticidal protein in the cytoplasm, or can result in the insecticidal protein being accumulated into a subcellular organelle such as a plastid, chloroplast, or mitochondria. Alternatively the insecticidal protein of the present invention or insecticidal fragments thereof could be localized to the protein secretion machinery of the particular host cell and result in an accumulation of the protein product out side of the cell and into the extracellular spaces surrounding the cell.

An additional embodiment of the present invention provides a method for controlling infestation of a plant by a coleopteran insect species. Preferably a pesticidal amount of an insecticidal protein of the present invention or insectidal fragment thereof is provided for consumption by the insect pest in the diet of the insect. The diet can consist of a plant part that the insect normally feeds upon, such as a plant tissue or plant cell. The insecticidal protein or insecticidal fragment thereof can be provided in a composition that is applied to the surface of the plant tissue, plant part, or plant cell or more preferably can be produced by the protein synthesis machinery of the cell and, as described above, accumulated within the plant cell or secreted outside of the plant cell, so long as the amount of the protein toxin provided is an insecticidal amount sufficient to inhibit the insect pest from further feeding, or to inhibit the further growth and development of the insect pest, or to cause mortality to the insect pest. The diet provided to the insect can also be an artificial diet that contains the toxin protein uniformly distributed within or topically applied to the exposed surface(s) of the diet substrate, or included as a concentration gradient within or topically applied to the exposed surface(s) of the diet substrate. The insecticidal toxin or fragment thereof is derived from a nucleotide sequence that is encoded in *Bacillus thuringiensis* by a nucleotide sequence that hybridizes under stringent conditions to the nucleotide sequence substantially complementary to SEQ ID NO:3.

The present invention also provides a method for detecting a first nucleotide sequence that hybridizes to a second nucleotide sequence as set forth in SEQ ID NO:3, wherein the first nucleotide sequence encodes an insecticidal protein or insecticidal fragment thereof and hybridizes under stringent hybridization conditions to the second nucleotide sequence. Exemplary sequences are SEQ ID NO:2 and SEQ ID NO:3.

The present invention also provides non-naturally occurring or synthetic nucleotide sequences that encode a TIC901 insecticidal protein or insecticidal fragment thereof or homolog thereof, wherein said TIC901 protein or insecticidal fragment thereof or homolog thereof is selected from the group of sequences consisting of SEQ ID NO:5, and SEQ ID NO:7. Preferably the non-naturally occurring nucleotide sequence or sequences provided for herein that encode an insecticidal protein or insecticidal fragment thereof are provided for expression of a TIC901 or related protein in plant cells. Therein, plant cells transformed with such sequences are provided for herein. Plants grown from the transformed plant cells are provided by the instant inventions. Seeds from the transformed plants of the present invention are also provided so long as the seeds contain at least the sequences encoding the insecticidal proteins or insecticidal protein fragments thereof.

Exemplary sequences of the present invention, in addition to those related to SEQ ID NO:3 and SEQ ID NO:4 include at least: (1) the nucleotide sequence as set forth in SEQ ID NO:5, and the amino acid sequence encoded by SEQ ID NO:5 as set forth in SEQ ID NO:6, also referred to herein as insecticidal protein TIC1201; (2) the nucleotide sequence as set forth in SEQ ID NO:7, and the amino acid sequence encoded by SEQ ID NO:7 as set forth in SEQ ID NO:8, also referred to herein as insecticidal protein TIC407; (3) the nucleotide sequence as set forth in SEQ ID NO:9, and the amino acid sequence encoded by SEQ ID NO:9 as set forth in SEQ ID NO:10, also referred to herein as insecticidal protein TIC417, and (4) the nucleotide sequence as set forth in SEQ ID NO:32, and the amino acid sequence encoded by SEQ ID NO:32 as set forth in SEQ ID NO:33, also referred to herein as insecticidal protein TIC431. Each of these proteins and the native B. t. nucleotide sequences encoding these proteins are related to TIC901 as defined herein. For example, and respectively, SEQ ID NO:5 is a nucleotide sequence encoding a TIC1201 insecticidal protein as set forth in SEQ ID NO:6. SEQ ID NO:5 as shown herein is identifiable by hybridization to SEQ ID NO:3 under stringent conditions. SEQ ID NO:5 encodes a protein that exhibits coleopteran toxic biological activity, exhibiting toxicity to corn rootworms and to Colorado potato beetles. SEQ ID NO:5, SEQ ID NO:3, SEQ ID NO:7, SEQ ID NO:9, and SEQ ID NO:32 are each capable of hybridizing to each other under hybridization conditions selected from the group consisting of stringent hybridization conditions and specific hybridization conditions. Each sequence can also be identified by hybridization to SEQ ID NO:2 under conditions selected from the group consisting of stringent hybridization conditions and specific hybridization conditions. Each sequence can also be identified by amplification using, for example, an oligonucleotide primer pair as set forth in SEQ ID NO:11 and SEQ ID NO:12, and an oligonucleotide primer pair as set forth in SEQ ID NO:23 and SEQ ID NO:27. The primer pair as set forth in SEQ ID NO:11 and SEQ ID NO:12, and the primer pair as set forth in SEQ ID NO:23 and SEQ ID NO:27 are exemplary and diagnostic for identifying the presence of a nucleotide sequence encoding a TIC901 or related insecticidal protein in a sample. These oligonucleotide pairs, when used alone or together under defined amplification conditions and in the presence of a suitable nucleotide sequence substrate, produce an amplicon consisting of from about 540 to about 640 base pairs. Thermal amplification reactions using these primer sets are useful for detecting the presence of a B.t. gene encoding an insecticidal protein corresponding to a TIC901 or related protein in a sample, and greatly simplifies the search for and identification of such related sequences. Other amplicons derived from the use of other primer pairs are also envisioned based on the nucleotide sequence alignment of, for example, SEQ ID NO:3, SEQ ID NO:5, SEQ ID NO:7, SEQ ID NO:9, and SEQ ID NO:32. Regions of substantial amino acid sequence identity of the proteins encoded by these nucleotide sequences correspond to nucleotide sequences that can be used for preparing complementary or substantially complementary sequences for use as probes or primers for use in thermal amplification reactions that allow for the detection of sequences related to TIC901, TIC1201, TIC407, TIC417, and TIC431.

Degenerate oligonucleotide probes and primers as set forth in SEQ ID NO:23 through SEQ ID NO:29 are additionally provided as a means for identifying any nucleotide sequence encoding a secreted insecticidal protein from at least a *Bacillus thuringiensis* species in which the nucleotide sequence identified with the degenerate oligonucleotide probes hybridizes under stringent conditions to one or more of the sequences selected from the group consisting of SEQ ID NO:2, SEQ ID NO:3, SEQ ID NO:5, SEQ ID NO:7, SEQ ID NO:9, SEQ ID NO:11, SEQ ID NO:12, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, and SEQ ID NO:32. Exemplary sequences identifiable using such oligonucleotides include sequences selected from the group consisting of SEQ ID NO:3, SEQ ID NO:5, SEQ ID NO:7, SEQ ID NO:9, SEQ ID NO:30, and SEQ ID NO:32, each encoding respectively peptides as set forth in SEQ ID NO:4, SEQ ID NO:6, SEQ ID NO:8, SEQ ID NO:10, SEQ ID NO:31, and SEQ ID NO:33.

Another embodiment comprises a method of detecting tic901 and related protein coding sequences in *Bacillus* strains comprising the steps of culturing a *Bacillus* species for from about 16 to about 45 hours in rich broth under aerobic conditions, detecting a protein in the culture supernatant that exhibits TIC901 related antigen identity and/or cross reactivity to an antibody that binds specifically to one or more TIC901 protein peptides or antigens, identifying and purifying a nucleotide sequence that encodes the detected protein, expressing the protein from the nucleotide sequence, and demonstrating insecticidal activity using the expressed protein.

Kits for detecting the presence of the nucleotide sequences of the present invention, as well as probes, primers, analogues and derivatives of the same, are also contemplated. Such kits contain one or more nucleotide sequences each for use either as a probe for detecting the presence of a nucleotide sequence encoding an insecticidal protein of the present invention or fragment thereof or related nucleotide sequences, or for use in combination with one or more other probes or primers included in such kit for amplifying one or more sequences of the present invention or a related nucleotide sequence. Such kits could also or alternatively contain antibody specific for binding to one or more peptides or the proteins of the present invention, as well as reagents for use with the probe or antibody, and the kits would also contain control samples for use in ensuring that the nucleotides or peptides identified with the probe and or antibody and reagents were functioning according to the manufacturers' instructions. All of the reagents necessary for carrying out the methods of identification of either nucleotide sequences or peptides would be packaged together in a kit along with instructions for use. An exemplary kit will contain a nucleotide sequence derived from a TIC901, TIC1201, TIC407, TIC417, and/or TIC431 coding sequence along with a sample of nucleotide sequence amplification primers, for example, as set forth in SEQ ID NO:11 and SEQ ID NO:12, or various combinations of SEQ ID NO:23-26 and SEQ ID NO:27-29 together with the reagents necessary for carrying out an amplification reaction, all packaged together in said kit.

It is therefore contemplated that the compositions and methods disclosed by the present invention will provide many advantages over the prior art including those specifically outlined above. In addition, the present invention provides an entirely new class of insecticidal proteins and nucleotide sequences encoding these proteins that were not previously known in the art.

BRIEF DESCRIPTION OF THE SEQUENCES

Figure 1A:
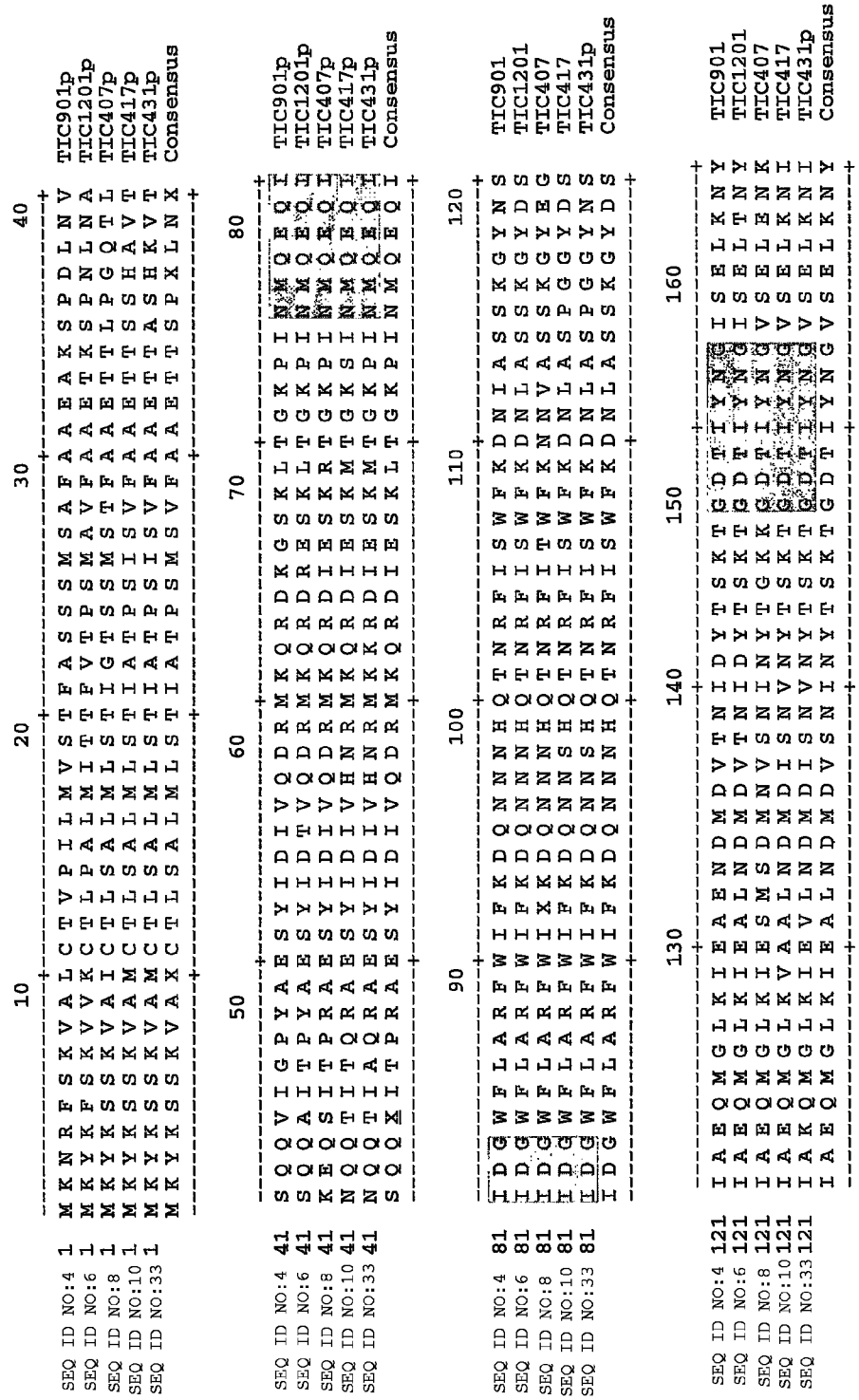
FIG. 1 is an amino acid sequence alignment of the precursor proteins TIC901p, TIC407p, TIC417p, TIC1201p, and TIC431p; each amino acid sequence contains a predicted thirty (30) amino terminal amino acid sequence characteristic of a type II signal peptide followed by thirteen additional amino acids from amino acid position thirty-one (31) through amino acid position forty-three (43) of their respective sequences that is not present in the mature protein isolated from spent fermentation media. The underlined amino acid in the consensus sequence at position 44 represents the mature protein amino terminal amino acid. The native nucleotide sequence encoding the corresponding shaded amino acids at positions 75-83, 147-153, and 275-283 were used as the basis for constructing redundant nucleotide probes and primers used for identifying sequences encoding these and other related insecticidal proteins from Bacillus species nucleotide sequences.

SEQ ID NO: 1 represents an amino acid sequence deduced from the results of Edman degradation of a gel purified about 38 kDa insecticidal protein secreted into the media by B. thuringiensis strain EG2158 cells, and corresponds substantially to the amino acid sequence as set forth in SEQ ID NO:4 from amino acid sequence position 44 through 58.

SEQ ID NO: 2 represents a synthetic nucleotide sequence for use as a probe for detecting a tic901 or related nucleotide sequence, or for use as one of a pair of thermal amplification primers to amplify all or a part of a tic901 or related nucleotide sequence, and corresponds to codon triplets preferred for use by B. thuringiensis and other Bacillus species, in particular exhibiting codon usage that is biased towards containing an A or a T at the third base pair position within each codon.

SEQ ID NO: 3 represents a native (also referred to herein as wild-type) Bacillus thuringiensis nucleotide sequence encoding a TIC901 protein. A predicted Pribnow box or Shine & Dalgarno sequence is located at about nucleotides 141-147. The predicted ORF encoding the predicted precursor TIC901 protein corresponds to nucleotides from position 153 through position 1,253. Nucleotides from position 282-325 correspond substantially to the sequence of the oligonucleotide probe as set forth in SEQ ID NO:2, which hybridizes to the complement of nucleotides 282-325 as set forth in SEQ ID NO:3. The GTA valine codon at nucleotide position 282-284 corresponds to the amino terminal amino acid in the secreted form of TIC901.

SEQ ID NO: 4 represents a 367 residue TIC901 amino acid sequence deduced from the open reading frame as set forth in SEQ ID NO:3 from nucleotide position 153 through nucleotide position 1,253. The full length 367 residue amino acid sequence corresponds to the predicted precursor protein amino acid sequence expressed from the native/wild type coding sequence in B. thuringiensis. The amino acid sequence from residue number 1 through residue 30 as set forth in SEQ ID NO:4 corresponds to the predicted amino terminal signal peptide or secretory signal peptide that is produced in B. thuringiensis from the expression of the nucleotide sequence as set forth in SEQ ID NO:3, is followed by thirteen (13) amino acids that are not present in the mature/secreted form of the 324 amino acid residue mature insecticidal protein sequence upon expression in B. thuringiensis. The 324 amino acid residue mature insecticidal protein sequence corresponds to the insecticidally effective TIC901 mature and secreted protein sequence. The 43 residue amino terminal amino acid sequence is predicted to be proteolytically cleaved from the precursor protein, either in part during translocation across the bacterial cytoplasmic membrane, or in part by an as yet undefined signal peptidase or other protease that recognizes the consensus sequence comprising the amino acid sequence residues XAA1-XAA2-GLN immediately before the scissile breakpoint, releasing the mature insecticidal protein into the extracellular milieu, where XAA1 corresponds to serine (SER), lysine (LYS), or asparagine (ASN), and XAA2 corresponds to glutamate (GLU) or glutamine (GLN).

SEQ ID NO:5 represents a native B. thuringiensis nucleotide sequence encoding an insecticidal protein designated herein as TIC1201. The sequence includes 529 nucleotides of sequence upstream of the predicted ATG initiation codon positioned at nucleotide position 530-532. A predicted consensus Pribnow box or Shine & Dalgarno sequence is positioned upstream of the predicted ATG initiation codon from nucleotide position 518 through 524. The open reading frame encoding the predicted precursor TIC1201 protein, like TIC901, comprises an amino terminal amino acid sequence corresponding to a predicted signal peptide or secretory targeting peptide. The sequence encoding the TIC1201 signal peptide is predicted to encode thirty (30) amino acids, followed by thirteen (13) additional amino acids that are not present in the mature/secreted form of the insecticidal protein. These thirteen additional amino acids terminate in a sequence encoding the SER-GLN-GLN peptidase recognition sequence identical to the sequence present in the TIC901 precursor protein sequence. The amino acid sequence of the insecticidal TIC1201 protein released into the media from B. thuringiensis strains expressing this sequence is predicted from the coding sequence to comprise 321 amino acid residues, being encoded by the nucleotide sequence from position 659 through 1621 as set forth in SEQ ID NO:5. Ever though the predicted ORF encoding the TIC1201 precursor protein is identified herein as being within nucleotides 530-1621, the ORF could possibly extend from nucleotide 437 through 1621. This is predicted to be unlikely because of the similarity of the signal peptide to that of TIC901, and the lack of any consensus Pribnow box or Shine & Dalgarno sequence within an reasonable proximity to any ATG initiation codon upstream of that positioned at nucleotides 518 through 524.

SEQ ID NO:6 represents a deduced 395 amino acid sequence of the TIC1201 precursor protein as encoded by the nucleotide sequence from nucleotide 530 through nucleotide 1621 as set forth in SEQ ID NO:5.

SEQ ID NO:7 represents a nucleotide sequence encoding the insecticidal protein designated herein as TIC407.

SEQ ID NO:8 represents a deduced 368 amino acid sequence for TIC407 as encoded by the nucleotide sequence from nucleotide position 196 through 1299 as set forth in SEQ ID NO:7.

SEQ ID NO:9 represents a nucleotide sequence encoding the insecticidal protein designated herein as TIC417.

SEQ ID NO:10 represents a deduced 364 amino acid sequence for TIC417 as encoded by the nucleotide sequence from nucleotide position 92 through 1173 as set forth in SEQ ID NO:9.

SEQ ID NO:11 represents a forward amplification thermal primer sequence, or a probe sequence, designated herein as prJWP139, corresponding to the coding sequence as set forth in SEQ ID NO:3 from nucleotide position 438 through 458, and further corresponding to the codons encoding the amino acid sequence ASN-ASN-ASN-HIS-GIN-THR-ASN-ARG from amino acid sequence position 96-103 as set forth in SEQ ID NO:4, biased towards codons preferred for use in gene sequences derived from *Bacillus thuringiensis* or other *Bacillus* species strains, in which the codons contain A and or T in the third position.

SEQ ID NO:12 represents a reverse amplification thermal primer sequence, or a probe sequence, designated herein as prJWP143, corresponding to the reverse complement of the coding sequence as set forth in SEQ ID NO:3 from nucleotide position 978 through 998, and further corresponding to the codons encoding the amino acid sequence GLN-LYS-PHE-ILE-TYR-PRO-ASN from amino acid sequence position 276-282 as set forth in SEQ ID NO:4, biased towards codons preferred for use in gene sequences derived from *Bacillus thuringiensis* or other *Bacillus* species strains, in which the codons contain A and or T in the third position.

SEQ ID NO:13 represents a synthetic, artificial, or non-naturally occurring nucleotide sequence encoding a TIC901 amino acid sequence variant.

SEQ ID NO:14 represents an amino acid sequence deduced from the coding sequence as set forth in SEQ ID NO:13 from nucleotide position 1 through nucleotide position 1104.

SEQ ID NO:15 represents an artificial nucleotide sequence for use as a probe or primer, described herein as prJWP151.

SEQ ID NO:16 represents an artificial nucleotide sequence for use as a probe or primer, described herein as prJWP152.

SEQ ID NO:17 represents an artificial nucleotide sequence for use as a probe or primer, described herein as prJWP186.

SEQ ID NO:18 represents an artificial nucleotide sequence for use as a probe or primer, described herein as prJWP183.

SEQ ID NO:19 represents an artificial nucleotide sequence for use as a probe or primer, described herein as prJWP155.

SEQ ID NO:19 represents an artificial nucleotide sequence for use as a probe or primer, described herein as prJWP155.

SEQ ID NO:20 represents an artificial nucleotide sequence for use as a probe or primer, described herein as prJWP156.

SEQ ID NO:21 represents an artificial nucleotide sequence for use as a probe or primer, described herein as prJWP168.

SEQ ID NO:22 represents an artificial nucleotide sequence for use as a probe or primer, described herein as prJWP170.

SEQ ID NO:23 represents a degenerate artificial oligonucleotide sequence for use as a probe or primer, described herein as prJWP200.

SEQ ID NO:24 represents a degenerate artificial oligonucleotide sequence for use as a probe or primer, described herein as prJWP201.

SEQ ID NO:25 represents a degenerate artificial oligonucleotide sequence for use as a probe or primer, described herein as prJWP202.

SEQ ID NO:26 represents a degenerate artificial oligonucleotide sequence for use as a probe or primer, described herein as prJWP203.

SEQ ID NO:27 represents a degenerate artificial oligonucleotide sequence for use as a probe or primer, described herein as prJWP204.

SEQ ID NO:28 represents a degenerate artificial oligonucleotide sequence for use as a probe or primer, described herein as prJWP205.

SEQ ID NO:29 represents a degenerate artificial oligonucleotide sequence for use as a probe or primer, described herein as prJWP206.

SEQ ID NO:30 represents a fragment of a nucleotide coding sequence derived from thermal amplification of the genome of EG2158 with oligonucleotides prJWP200 and prJWP204.

SEQ ID NO:31 represents the amino acid sequence from the primary open reading frame set forth in SEQ ID NO:30.

SEQ ID NO:32 represents a nucleotide sequence encoding the insecticidal protein designated herein as TIC431.

SEQ ID NO:33 represents a deduced 364 amino acid sequence for TIC431 as encoded by the nucleotide sequence from nucleotide position 1 through 1092 as set forth in SEQ ID NO:32.

DETAILED DESCRIPTION OF THE INVENTION

In accordance with the present invention, a new genus of nucleotide sequences encoding a new genus of insecticidal proteins derived from *Bacillus thuringiensis* and related *Bacillus* strains has been discovered. As defined elsewhere herein, these nucleotide coding sequences hybridize to one another under appropriate hybridization conditions and the proteins encoded by these nucleotide sequences cross react with antiserum raised against any one of the other proteins. An alignment of the nucleotide sequences encoding the mature/secreted forms of the TIC1201, TIC901, TIC407, TIC417, and TIC431 proteins reveals that the coding sequence encoding the mature TIC901 protein fragment (secreted form of TIC901 from amino acid position 44 through amino acid position 367 as set forth in SEQ ID NO:4) is from about 79 to about 91 percent identical to each of the sequences encoding the other four mature protein fragments disclosed herein; the sequence encoding the predicted mature/secreted TIC417 protein fragment (amino acid position 44 through amino acid position 364 as set forth in SEQ ID NO:10) is from about 75 to about 95 percent identical to each of the sequences encoding the other three mature protein fragments disclosed herein; the sequence encoding the predicted mature/secreted TIC407 protein fragment (amino acid position 44 through amino acid position 368 as set forth in SEQ ID NO:8) is from about 75 to about 82 percent identical to each of the sequences encoding the other four mature protein fragments disclosed herein; the sequence encoding the mature/secreted TIC1201 fragment (amino acid position 44 through amino acid position 395 as set forth in SEQ ID NO:6) is from about 80 to about 91 percent identical to each of the sequences encoding the other four mature protein fragments disclosed herein, and the sequence encoding the mature/secreted TIC431 fragment (amino acid position 44 through amino acid position 364 as set forth in SEQ ID NO:33) is from about 75 to about 95 percent identical to each of the sequences encoding the other four mature protein fragments disclosed herein. The proteins encoded by each of these nucleotide coding sequences exhibit coleopteran species inhibitory biological activity, exhibit substantial amino acid sequence identity in part and substantial amino acid sequence similarity in part, and therefore are considered to be related insecticidal proteins. The predicted mature/secreted form amino acid sequence for the TIC417 insecticidal protein MIC417m) is about 78.9 percent identical to the corresponding mature/secreted form amino acid sequence for TIC901 (TIC901m). The predicted mature/secreted form amino acid sequence for the TIC1201 insecticidal protein (TIC1201m) is about 90.1 percent identical to the corresponding amino acid sequence for TIC901m, and is about 80.7 percent identical to the corresponding amino acid sequence for TIC417m and TIC431m. The predicted mature/secreted form amino acid sequence for the TIC407 insecticidal protein MC407m) is about 80% identical to the corresponding TIC901m, about 75% identical to the corresponding TIC417m, and about 82% identical to the corresponding TIC1201m. The predicted mature/secreted form amino acid sequence for the TIC431 insecticidal protein (TIC431m) is about 75% identical to the mature TIC407, about 79% identical to the mature TIC901, about 80% identical to the TIC1201, and about 95% identical to the TIC417 mature protein amino acid sequence. Each of the proteins encoded by the nucleotide sequences disclosed herein can be expressed in plants alone or in various combinations with each other or with other coleopteran inhibitory insecticidal agents such as proteins, crystal proteins, S-endotoxins, lectins, patatins, and other toxins and the like to achieve a means of insect resistance management in the field that has not been feasible before by merely using the known coleopteran insecticidal proteins derived from *Bacillus thuringiensis* strains, such as Cry3 proteins, VIP and/or WAR and/or MIS proteins, and various coleopteran inhibitory insecticidal proteins derived from *Bacillus latersoporous* species, *Bacillus sphaericus* species, and *Xenorhabdus* and *Photorhabdus* bacterial species. The proteins of the present invention can also be used in plants in combination with other types of insecticidal agents and or insecticidal toxins for achieving plants transformed to contain at least one means for controlling one or more of each of the common plant pests selected from the groups consisting of coleopteran insect pests, lepidopteran insect pests, piercing and sucking insect pests, and the like. Other proteins and or insect controlling agents that can be expressed in a plant in combination with the proteins of the present invention include but are not limited to lepidopteran insecticidal proteins from *Bacillus* species; such as Cry proteins derived from *Bacillus thuringiensis*, *Bacillus laterosporous*, and *Bacillus sphaericus* species, and WAR, MIS, and/or VIP proteins isolatable from various *Bacillus* species, insecticidal proteins derived from *Xenorhabdus* and *Photorhabdus* bacterial species, and compositions such as transgenic dsRNA's expressly directed to suppression of one or more genes in one or more target insect pests. As used herein, "insecticidal polypeptide" or "insecticidal protein" or "insecticidal fragment thereof" refers to a polypeptide exhibiting insecticidal properties, e.g., a polypeptide that inhibits the growth, development, viability or fecundity of target insect pests, and an insecticidal agent including all of these as well as double stranded RNA's directed to suppression of one or more genes in one or more target pests.

Surprisingly, the proteins of the present invention appear to be unrelated to any of the *Bacillus thuringiensis* insecticidal proteins heretofore discovered in the art. The proteins of the present invention are shown herein to be excreted into the extracellular space surrounding the *Bacillus* species from which they are derived. These proteins are shown herein to be significantly smaller than the known Cry, VIP, WAR and MIS proteins previously known in the art, and may be expressed during the vegetative stage of growth of isolated and purified bacterial cell cultures. This is unlike the expression of Cry proteins which are expressed generally in the sporulation phase of growth and which form various crystalline bodies within the forespore of the cell.

As will become apparent to those of skill in the art, the inventors herein disclose the isolation and purification of a nucleotide sequence, tic901, encoding a precursor TIC901 protein (TIC901p) that is subsequently proteolytically processed to release a mature TIC901 protein (TIC90m) that exhibits coleopteran species inhibitory biological activity. The inventors herein disclose the use of the tic901 sequence as a means for identifying a multitude of other related sequences, which each also encode insecticidal proteins related to TIC901, TIC901p, and TIC901m, and disclose the use of antibodies raised against TIC901m in an ELISA method for detecting strains of Bt that produce TIC901 related proteins expressed from coding sequences related to that encoding TIC901.

Nucleotide sequences disclosed herein and encoding TIC901 were derived from strains of *Bacillus thuringiensis*, including strains EG2158, EG6489, EG6561, EG12450, and EG4653. These strains have been deposited under the provisions of the Budapest Treaty with the permanent collection of the Agricultural Research Service Culture Collection, Northern Regional Research Laboratory (NRRL), U.S. Department of Agriculture (USDA), 1815 North University Street, Peoria, Ill. 61604. The relevant strains were deposited with the NRRL between Apr. 29, 1987 and Feb. 6, 2002. *B. thuringiensis* strain EG2158 was provided with the NRRL accession No. NRRL B-18213; and *B. thuringiensis* strain EG12450 was provided with the NRRL accession No. NRRL B-30357. Nucleotide sequences related to tic901, and amino acid sequences related to TIC901 (including precursor and mature species of TIC901) which are disclosed herein include but are not limited to tic1201 and the encoded insecticidal protein TIC1201 isolated from and produced at least by B.t. strains EG3618 and 86833, tic407 and the encoded insecticidal protein TIC407 isolated from and produced at least by B.t. strain EG6618, and tic417 and the encoded insecticidal protein TIC417 isolated from and produced at least by B.t. strains EG2158, EG6489, and EG6561. and TIC431 encoded at lease by B.t. strain EG4653.

A broth culture derived from the purified B.t. strain EG2158 was tested for insecticidal activity, and was determined to exhibit coleopteran insect inhibitory biological activity directed against Colorado Potato Beede (CPB). A protein exhibiting a mass of about 38 kDa as judged by SDS-PAGE was purified from the broth culture and was observed to contain the indicated coleopteran toxicity. This protein was subjected to automated Edmund degradation, and the results yielded an amino acid sequence believed to be the 15 amino terminal amino acid sequence (SEQ ID NO:1) of the about 38 kDa protein, i.e., the TIC901m protein. A semi-redundant synthetic oligonucleotide sequence (WD444; SEQ ID NO:2) corresponding to naturally occurring codons preferred for use in protein coding sequences isolated from *Bacillus thuringiensis* or related *Bacillus* species bacteria, i.e. exhibiting a preference for A or T in the third position of each codon, was constructed for use as a probe for detecting sequences of homology that could conceivably encode the about 38 kDa insecticidal protein in *Bacillus thuringiensis*. A nucleotide sequence library was constructed from DNA purified from Bt strain EG2158. The purified DNA was digested to completion with HindIII, and fragments were inserted into a HindIII digested, calf intestine phosphatase treated pUC18 plasmid vector to construct a Bt strain EG2158 genomic library. The DNA library was transformed into an *E. coli* strain and the transformation mixture was plated onto solid selection media. The colonies that arose were probed with a sample of alkaline phosphatase conjugated synthetic nucleotide sequence probe WD444 (SEQ ID NO:2). A recombinant *E. coli* strain designated as EG12447 containing plasmid pEG1379 (also known as pMON74007), a pUC18 derivative that contained an 8 kb HindIII fragment isolated from *B.*

*thuringiensis* strain EG2158, hybridized to the alkaline phosphatase conjugated oligonucleotide probe. The 8 kb HindIII fragment in plasmid pEG1379 was determined by nucleotide sequence analysis to contain the entire nucleotide sequence encoding the TIC901p protein. NRRL received a viable deposit of strain EG12447 and designated the deposited sample with the NRRL accession No. NRRL B-30549 on Feb. 6, 2002.

The nucleotide sequence of the open reading frame encoding the about 38 kDa insecticidal protein was determined. The open reading frame encoding the TIC901p protein was designated as tic901. The open reading frame consists of a nucleotide sequence of 1101 nucleotides (nucleotides 153-1,253 as set forth in SEQ ID NO:3), and is predicted to encode a precursor protein consisting of 367 amino acids (SEQ ID NO:4). The predicted molecular weight of the amino acid sequence deduced from the open reading frame is 41,492 Daltons, which is within reasonable expectations of the mass of the secreted protein estimated by SDS-PAGE analysis as about 38 kDa considering the loss of mass of a signal peptide of between three and four kDa. The precursor protein (TIC901p) is predicted to exhibit an isoelectric point of 6.368 and a net charge of −2.102 at pH 7.0. The total composition of the nucleotide sequence encoding the precursor protein is comprised of 69% AT, which is consistent with other coding sequences identified from *B. thuringiensis* and other *Bacillus* strains. The nucleotide composition of the coding sequence is also consistent with other genes characterized from *Bacillus* species, containing about 39% adenosine, about 18% guanosine, about 30% thymidine and about 13% cytosine.

The native tic901 coding sequence in pEG1379 appeared to be incapable of producing a measurable amount of the TIC901m protein from recombinant *E. coli* cultures containing this plasmid. This was not unexpected given the known lack of functionality of *Bacillus* promoters in *E. coli*, and the differences in codon preference between the two organisms. No CPB inhibition was observed with strain EG12447 culture supernatants or cells containing this plasmid. The 8 kB insert was excised and placed into an *E. coli/B. thuringiensis* shuttle vector to form plasmid pEG12450. pEG12450 was transformed into an acrystalliferous strain of *Bacillus thuringiensis*, EG10650 (U.S. Pat. No. 6,468,523), to produce strain EG12450. EG10650 was derived from an acrystalliferous *B. thuringiensis* strain EG10368 (identified in U.S. Pat. No. 5,322,687) by replacing the npr and apr (neutral protease and acidic protease genes, respectively) with deletion mutant alleles of these two protease genes, npr3 and apr1 respectively (U.S. Pat. No. 5,759,538). Culture supernatants derived from EG12450 tested positive for Colorado Potato Beetle (CPB) inhibitory activity. Protein purified from the culture supernatants from EG12450 also tested positive for CPB inhibitory activity. No crystal structures were observed in sporulated cultures, but the cell pellets/sporulated culture biomass also tested positive for CPB inhibitory bioactivity suggesting that some portion of the TIC901 protein remained associated with the spore/culture or that spores consumed by the test species of insect germinated within the insect and produced sufficient TIC901 insecticidal protein to cause an observable inhibitory effect.

The culture supernatants and purified protein from strain EG12450 were also tested for biological activity against corn rootworms. Inhibitory bioactivity was observed for both Southern and Western corn rootworms (*Diabrotica undecempunctata howardii* and *Diabrotica virgifera virgifera* respectively).

A diverse collection of *Bacillus* strains was examined as disclosed herein by the inventors in order to determine whether these *B. thuringiensis* and/or *B. sphaericus* strains also produced extracellular proteins related to TIC901. In particular, cell paste and spent media were processed from 279 strains and provided in bioassay to southern corn rootworm larvae. About one third of the strains produced secreted proteins into the growth media that tested positive for rootworm inhibitory activity. Priority was given to thirty six (36) strains that produced extracellular proteins that exhibited the greatest effective rootworm inhibition. These strains were screened further by determining whether the TIC901 coding sequence hybridized to sequences present in each strains' genome, and comparing the results for these strains with the results obtained by probing strain EG2158 with the native TIC901 coding sequence. The results are shown in Table 1.

TABLE 1

RFLP Isotypes of *Bacillus* Strains Producing Secreted CRW Insecticidal Proteins

| Strain | tic901 RFLP[1] | TIC Protein Homolog ID |
|---|---|---|
| EG 2158[2] | A | 901/417 |
| EG 2211 | B | 1201 |
| EG 2874 | B | 1201 |
| EG 2904 | B | 1201 |
| EG 3109 | B | 1201 |
| EG 3111 | B | 1201 |
| EG 3116 | B | 1201 |
| EG 3117 | B | 1201 |
| EG 3119 | B | 1201 |
| EG 3120 | B | 1201 |
| EG 3171 | B | 1201 |
| EG 3173 | B | 1201 |
| EG 3177 | B | 1201 |
| EG 3354 | B | 1201 |
| EG 3458 | B | 1201 |
| EG 3461 | B | 1201 |
| EG 3618 | B | 1201[3] |
| EG 3619 | B | 1201 |
| EG 3620 | B | 1201 |
| EG 3753 | B | 1201 |
| EG 3787 | B | 1201 |
| EG 4189 | B | 1201 |
| EG 4191 | B | 1201 |
| EG 4193 | B | 1201 |
| EG 4332[4] | — | |
| EG 4834 | B | 1201 |
| EG 5194 | B | 1201 |
| EG 5552 | — | |
| EG 5858[4] | — | |
| EG 6489 | A | 901/417 |
| EG 6555 | B | 1201[3] |
| EG 6561 | A | 901/417 |
| EG 6564 | B | 1201 |
| EG 6618 | C | 407[3] |
| EG 6890 | B | 1201 |
| EG 10650 | — | |
| 86833 | B | 1201 |

[1]Total DNA isolated from each strain was digested to completion with HindIII and analyzed by Southern blot. The letter A, B, C or D corresponds to the size of a particular restriction fragment (polymorphism) illuminated by tic901 or SEQ ID NO: 2 probe.
[2]EG 2158 also contains a 3rd nucleotide sequence homolog related to tic/901, tic1201, tic407, and tic417 as set forth in SEQ ID NO: 30
[3]indicates only partial nucleotide sequence identification obtained, but all or portion of sequence obtained encodes protein sequence 100% identical to indicated TIC protein
[4]indicates that these strains have been shown to produce extracellular substances that exhibit *Lygus* inhibitory biological activity Four (4) of the thirty-six (36) strains failed to produce a nucleotide fragment that hybridizes with the VIP1 or VIP 2 probes (strains EG4332, EG5858, EG6618, and 86833) under conditions of high stringency, i.e., washes at 0.5×SSC and at 65° C. All other strains produced a nucleotide fragment that hybridized to a TIC901 probe, however, interesting hybridization signal intensity variations were observed, specifically with reference to the HindIII restriction fragment(s) that were illuminated by the TIC901 probe. There were essentially three different sized restriction fragments (polymorphisms) that were identified by hybridization to a tic901 probe. It was at first believed that only one of the three different fragments capable of hybridizing under these conditions to a tic901 probe was shown to be present in any one strain. Two restriction fragment polymorphisms exhibited a different signal intensity when hybridized with the tic901 probe compared to the signal produced by hybridization of this probe to the tic901 gene fragment from strain EG2158. This result suggests that there are at least three alleles of the tic901 coding sequence present in these thirty six (36) strains. Sequence analysis, as described herein, of each of these three restriction fragment length polymorphisms has allowed the identification of each of these related ORF's (open reading frames) encoding a TIC901 related protein contained within each sequence. A comparison of these nucleotide sequences has been made as shown herein by aligning the sequences to the native TIC901 coding sequence to determine the extent of identity. In addition, the proteins encoded by the TIC901 and TIC1201 ORF's identified in these restriction fragments have been tested for insecticidal properties, and each exhibits coleopteran pest toxicity. It is therefore believed that the TIC407 and TIC417 proteins will also exhibit coleopteran insecticidal biological activity based on their high degree of relationship to the TIC901 and TIC1201 proteins. As a consequence of the significant identity of amino acid sequence relationship between the TIC407, TIC417, and TIC1201 proteins in comparison to TIC901, the proteins are described herein as amino acid sequence variants of each other. TIC1201, for example, contains three fewer amino acids than TIC901 and contains 31 amino acid sequence variations in comparison to TIC901. Therefore, when compared to TIC901, the other TIC amino acid sequences contain amino acid variations that may contribute to different insecticidal spectrum and/or virulence and potency. Subsequent analysis of these and other strains using thermal amplification methods with primer pairs that have degeneracy incorporated into their sequences based on nucleotide sequence alignments of the coding sequences for the TIC901, TIC407, TIC1201, and TIC417 proteins resulted in amplicons that could correspond to a TIC407 coding sequence present in the genome of the strains EG5858, EG5552, and EG4332. These sequences may not have appeared using a TIC901 specific blot because it was determined that the TIC407 sequence was present on a large, approximately 18-19 kb, HindIII fragment which may not have transferred effectively to the blot membrane.

It is intended that the proteins of the present invention be used for agricultural purposes, i.e., for protecting plants from insect pest infestation, and more particularly for protecting plants from coleopteran insect pest infestation. As exemplified herein, the proteins of the present invention are useful for protecting plants at least from Colorado Potato Beetle infestation and at least from Corn Rootworm infestation. Plant protection can be achieved by topical application of a plant or plant parts such as by applying to the surface of the plant, i.e., the leaves, flowers, stems, stalks, and roots, a composition in the form of a dust, spray, powder, or emulsion or other agriculturally acceptable excipient that contains an insecticidally effective amount of one or more of the proteins of the present invention. Alternatively, the agricultural excipient can contain, in addition to one or more of the proteins of the present invention, one or more additional insecticidal proteins effective for inhibiting the same spectrum of insect pests believed to be controlled by the proteins of the present invention such as Cry3 proteins, CryET33/34, CryET80/76, PS149B1 and other coleopteran inhibitory binary toxin proteins, VIP/MIS/WAR proteins, and the like, and/or proteins that are effective in controlling an altogether different spectrum of plant insect pests such as Cry1's, Cry2's, Cry9's, and the like. It is also within the scope of the present invention for an agricultural excipient as described above to contain other types of pesticidal compositions such as fungicides and/or acaricides and the like. Alternatively, and preferably, the plant itself will be transformed to contain one or more nucleotide sequences modified for improved expression of one or more of the proteins of the present invention in planta or expression of an insecticidal portion thereof, alone or in combination with other insecticidal agents such as those capable of being produced in planta using methods in molecular biology, including double stranded RNA mediated methods for suppressing genes in target pest cells.

The TIC901, TIC1201, TIC407, TIC417, and TIC431 proteins are insecticidal compounds active against coleopteran insects such as CPB and rootworms. These proteins as set forth in SEQ ID NO:4, SEQ ID NO:6, SEQ ID NO:8, SEQ ID NO:10, and SEQ ID NO:33 respectively, and insecticidal fragments thereof, and related insecticidal proteins may be used as the active ingredient in insecticidal formulations useful for controlling coleopteran insects. As used herein and with reference to insecticidal proteins that are related to these proteins, it is intended that related insecticidal proteins are those that are identified as homologs of these proteins or those that are identified as being encoded by a nucleotide sequence that hybridizes either under stringent hybridization conditions or specific hybridization conditions to all or a part of the native Bacillus thuringiensis sequence encoding the TIC901 protein, the TIC1201 protein, the TIC417 protein, the TIC407 protein, the TIC431 protein or an insecticidal portion thereof. Stringent conditions, as defined herein, comprise at least hybridization at 42° C. followed by two washes for five minutes each at room temperature with 2×SSC, 0.1% SDS, followed by two washes for thirty minutes each at 65° C. in 0.5×SSC, 0.1% SDS. Of course, one skilled in the art will recognize that, due to the redundancy of the genetic code, many other sequences are capable of encoding such related proteins, and those sequences, to the extent that they function to express insecticidal proteins either in Bacillus strains or in plant cells, are intended to be encompassed by the present invention, recognizing of course that many such redundant coding sequences will not hybridize under these conditions to the native sequences encoding TIC901, TIC1201, TIC407, TIC417, and/or TIC431. It should be understood that when referring to a TIC901 or related insecticidal protein or insecticidal fragment thereof, or when referring to a nucleotide sequence encoding a TIC901 or related insecticidal protein or insecticidal fragment thereof, that TIC901 is interchangeable and indistinguishable from reference to TIC407, TIC417, TIC431, and TIC1201 and the like, including the amino acid sequence SEQ ID NO:31 encoded by the nucleotide sequence as set forth in SEQ ID NO:30, which includes the full length insecticidal protein encoded therefrom by the full length coding sequence for the protein, a part of which is exemplified by the amino acid sequence as set forth in SEQ ID NO:31.

Some nucleotide sequences that may, be related to the nucleotide sequences of the present invention may not hybridize under stringent conditions, but may in fact hybridize to a tic901, tic1201, tic407, tic431, and/or tic417, or a related sequence using specific hybridization conditions. Such sequences may encode a protein that has at least about 30% amino acid sequence identity to the proteins of the present invention. Proteins exhibiting at least about 30% sequence identity may also exhibit very similar tertiary structures and so may also exhibit similar or related biological activity. With reference to the instant invention, such similarity in tertiary structure would include insecticidal biological activity. Specific hybridization conditions that enable the identification of more distantly related nucleotide sequences include a first hybridization at a low temperature, typically about 40° C. or so, followed by washes as indicated above at room temperature to remove non-specifically bound probe, followed by exposure to film (in instances in which an investigator uses isotopic labeling means) or exposure to immunological reagents and chemical developing reagents to identify nucleotide fragments that hybridize to a specific gene probe. An indication that the hybridization is non-specific is one in which many hybridizing fragments are observed. In instances in which a number of hybridizing fragments are observed, the blot is washed one or more times, each time at a slightly higher temperature than the previous wash (for example, each wash could be accomplished at a temperature of about 5° C. more than the previous wash) until only one or a few (two or three) hybridizing fragments are observed, this one or few fragments being exhibiting specific hybridization, and can then be cloned and sequences to determine the extent of homology and/or identity to the original probe sequence. Such sequences would be specifically related in that they encode proteins that have a related function, for example, insecticidal activity, to the protein encoded by the original sequence derived from the nucleotide probe.

Coding sequences are conceivable that function to encode all or an insecticidal portion of a TIC901 or related protein that do not hybridize under stringent conditions. However, such sequences are derived from the native nucleotide sequence on the basis that the native nucleotide sequence is capable of being modified to exhibit a non-native sequence that still encodes the same or substantially the same native amino acid sequence, or that the native amino acid sequence is capable of being used along with a codon table to back-translate from the amino acid sequence, allowing the skilled artisan to arrive at a nucleotide sequence that encodes all or an insecticidal portion of a TIC901 or related protein. All such sequences are intended to be within the scope of the present invention.

Insecticidal compositions can be produced from bacterial strains expressing the proteins of the present invention. A *B. thuringiensis* strain containing one or more nucleotide sequences encoding one or more TIC901 or related proteins and/or substantial equivalents thereof, can be cultured using known standard media and fermentation techniques. Because the proteins of the present invention are preferably secreted into the extracellular milieu, upon completion of the fermentation cycle, the bacteria expressing TIC901 or a homolog thereof can be harvested by first separating the *B. thuringiensis* along with any spores and crystals produced therein, from the spent fermentation broth by means well known in the art. The recovered *B. thuringiensis* spores and crystals can be formulated into a wettable powder, a liquid concentrate, granules, solution, emulsion, spray, suspension, powder, foam, paste, aerosol, capsule or other finely or coarsely divided material or impregnant for natural or synthetic material, or other formulation, in admixture with suitable carriers, diluents, adjuvants, preservatives, dispersants, solvents, emulsifying agents, inert carriers and other components suitable for physically or chemically associating with plants or their locus, for oral uptake by target plant pathogens, and to facilitate handling and application for particular target pests. The formulation and application procedures are all well known in the art.

Formulated bait granules containing an attractant and spores and crystals of the *B. thuringiensis* isolates or concentrated spent fermentation media or insecticidal proteins purified from the spores or spent fermentation media, or recombinant microbes comprising the nucleotide sequences encoding TIC901 or related insecticidal proteins obtainable from the *B. thuringiensis* isolates disclosed herein, can be applied to the environment of the pest. The bait may be applied liberally since the toxin does not affect animals or humans. Product may also be formulated as a spray or powder. Pests pick the product up on their feet or abdomen and carry it back to the nest where other pests will be exposed to the toxin. The *B. thuringiensis* isolate or recombinant host expressing a nucleotide sequence or gene encoding a TIC901 or related protein of the present invention may also be incorporated into a bait or food source for the pest.

As would be appreciated by a person skilled in the art, the pesticidal concentration will vary widely depending upon the nature of the particular formulation, particularly whether it is a concentrate or to be used directly. The pesticide will be present in at least 1% by weight and may be 100% by weight. The dry formulations will have from about 1-95% by weight of the pesticide while the liquid formulations will generally be from about 1-60% by weight of the solids suspended or capable of being suspended in the liquid phase. The formulations will generally have from about $10^2$ to about $10^4$ cells/mg or from about 5 to about 100 parts per million of the active component insecticidal protein, i.e., the TIC901 protein, amino acid sequence variant thereof, insecticidal portion or fragment thereof, or homolog thereof such as TIC431, TIC1201, TIC417, and TIC407. These formulations will be administered at from about 50 mg (liquid or dry) to about 1 kg or more per hectare. The formulations can be applied to the environment of the coleopteran pests, e.g., plants, soil, or water by spraying, dusting, sprinkling, or the like, and can also be applied to the surfaces of seeds as a seed treatment or seed coating and can be permeated into the seed coat and/or cotyledon(s). One skilled in the art will also recognize that combinations of the proteins of the present invention when combined together in a composition or formulation, may also have particularly useful and beneficial effects, for example, providing a broader host range for controlling insect infestation, or increasing the virulence and potency of a composition intended for use as an insecticidal agent.

It is well within the skill of the art to construct a variant or modified nucleotide sequence that encodes the insecticidal protein of the present invention, or an insecticidal fragment thereof, or an insectidical amino acid sequence variant thereof that exhibits improved insecticidal activity compared to the native amino acid sequence, and place that nucleotide sequence into an expression cassette that functions in plants to cause the transcription of the coding sequence into a messenger RNA that is subsequently translated in the cells of the plant such that an insecticidally effective amount of the insecticidal protein is produced within the plant tissues. It also within the skill of the art to transform a plant cell, preferably a corn, cotton, soybean, canola, rice, wheat, oat, milo, grass, forage plant, fruit tree, ornamental flower, tomato, potato, carrot, kale, and tobacco plant cell and the like with a nucleotide sequence embedded within a plant functional expression cassette, to select for cells that contain the sequence and are expressing insecticidally effective amounts of a TIC901 protein, (and/or amino acid sequence variant thereof, insecticidal portion or fragment thereof, or homolog thereof such as TIC431, TIC1201, TIC417, and TIC407) and to produce plants from such transformed cells. One skilled in the art would know to use electroporation, infusion, ballistic methods, or *Agrobacterium tumefaciens* mediated methods and the like for introducing the nucleotide sequences of the present invention or modifications thereof into a plant cell. Such methods are well known in the art.

The term "variant or modified" with reference to nucleotide sequences is intended to refer to nucleotide sequences which encode the same toxins or which encode equivalent toxins having similar insecticidal activity, the term "equivalent toxin" referring to a toxin exhibiting the same, essentially the same, or improved biological activity against the target pests as the claimed native or referent toxin. A variant or modified nucleotide sequence intended for use in dicot plants would encode substantially the same amino acid sequence as the native coding sequence, i.e., the coding sequence found in nature, but would comprise a total combined GC composition from about 49 to about 58 percent, and would avoid utilizing the least preferred codon used by the intended dicot plant, determined by compiling such preference and usage frequencies from a consortium of coding sequences derived from one or more individual dicot plant species intended to be transformed with the variant or modified nucleotide sequence. A variant or modified nucleotide sequence intended for use in a monocot plant would also encode substantially the same amino acid sequence as the native coding sequence, and would comprise a total combined GC composition from about 52 to about 64 percent or more, and would also avoid utilizing the least preferred codon for encoding any amino acid as determined by compiling such preference and usage frequencies from a consortium of coding sequences derived from one or more individual monocot plant species intended to be transformed with the variant or modified nucleotide sequence. Codon usage frequency is intended to refer to the number of times, on average, that a particular codon is used in a coding sequence. For a particular plant species, a codon that is intended to cause the incorporation of a particular amino acid into a nascent amino acid sequence will be utilized on average with some relative fixed frequency. For amino acids that utilize only two codons, this frequency is generally about fifty-fifty, i.e., each codon being used about half the time, unless one of the codons utilizes a substantially greater number of purines or pyrimidines that are not typically representative of the GC content of the particular plant species. For *Bacillus* species, for example, coding sequences generally are from about 60 to about almost 70 percent AT. Codon usage in *Bacillus* species is biased toward the use of codons that are enriched for the presence of A or T in a particular codon, and more particularly with A or T in the third base position of any particular codon. Therefore, codons that primarily utilize G or C are used in a native and/or naturally occurring *Bacillus* coding sequence with a much lower frequency than codons that contain A's or T's. Therefore, when producing a variant or modified nucleotide sequence intended for use in a particular plant, monocot or dicot, it is important to ensure that appropriate attention is given to avoiding using the least preferred codon with any great frequency for that particular plant. In fact, for monocots, it is preferred that the coding sequence mimic the GC distribution found in most native or naturally occurring monocot plants; that being a preferred about 65% GC for about the first 10% of the coding sequence, tapering down to about 60% GC for the second 10-15% of the coding sequence, and leveling off to about a 50-55% GC for the middle one half or more of the coding sequence, and then gradually increasing the GC % of the coding sequence up to about 60-64% through the last 15-20% of the coding sequence. This distribution of GC % seems to mimic as closely as possible the GC % distribution of a naturally occurring monocot gene and therefore it is believed that a synthetic or artificially produced gene or coding sequence should resemble this architecture as well.

As used herein, "synthetic coding sequences" or "non-naturally occurring coding sequences" encoding the *B. thuringiensis* TIC901 proteins or homologs or derivatives thereof as insecticidal toxins of the present invention are those prepared in a manner involving any sort of genetic isolation or manipulation that results in the preparation of a coding sequence that encodes a TIC901 insecticidal protein or related amino acid sequence or homolog or variant or the substantial equivalent thereof including coding sequences that encode at least an insecticidal portion of a TIC901 protein, a TIC431 protein, a TIC1201 protein, a TIC407 protein, or a TIC417 protein. This includes isolation of the coding sequence from its naturally occurring state, manipulation of the coding sequence as by codon modification (as described herein), chemical synthesis such as phosphoramidite chemistry and the like, or site-specific mutagenesis (as described herein), truncation of the coding sequence or any other manipulative or isolative method.

As used herein, the phrase "percentage of sequence identity" is determined by comparing two optimally aligned sequences over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity. A sequence which is identical at every position in comparison to a reference sequence is said to be identical to the reference sequence and vice-versa. A first nucleotide sequence when observed in the 5' to 3' direction is said to be a "complement" of a second or reference nucleotide sequence observed in the 3' to 5' direction if the first nucleotide sequence exhibits complete complementarity with the second or reference sequence. As used herein, nucleic acid sequence molecules are said to exhibit "complete complementarity" when every nucleotide of one of the sequences read 5' to 3' is complementary to every nucleotide of the other sequence when read 3' to 5'. A nucleotide sequence that is identical at every position when read 5' to 3' in comparison to a reference nucleotide sequence read 5' to 3' is said to be identical to the reference sequence and vice-versa. A nucleotide sequence that is complementary to a reference nucleotide sequence will exhibit a sequence identical to the reverse complement sequence of the reference nucleotide sequence. These terms and descriptions are well defined in the art and are easily understood by those of ordinary skill in the art.

As used herein, "substantial homology", with reference to nucleic acid sequences, refers to nucleotide sequences that hybridize under stringent conditions to the coding sequences as set forth in SEQ ID NO:3, SEQ ID NO:5, SEQ ID NO:7, SEQ ID NO:9, or SEQ ID NO:32 or the complements thereof. Sequences that hybridize under stringent conditions to SEQ ID NO:3, SEQ ID NO:5, SEQ ID NO:7, SEQ ID NO:9, or SEQ ID NO:32 or the complements thereof, in particular from about nucleotide position 153 to about nucleotide position 1,253 of SEQ ID NO:3, and more particularly from about nucleotide position 282 to about nucleotide position 1,253 of SEQ ID NO:3; or from about nucleotide position 437 to about nucleotide position 1621 of SEQ ID NO:5, more particularly from about nucleotide position 530 to about nucleotide position 1621 of SEQ ID NO:5, and even more particularly from about nucleotide position 659 to about nucleotide position 1621 of SEQ ID NO:5; or from about nucleotide position 196 to about nucleotide position 1299 of SEQ ID NO:7, or more particularly from about nucleotide position 325 to about nucleotide position 1299 of SEQ ID NO:7; or from about nucleotide position 215 to about nucleotide position 1306 of SEQ ID NO:9, or more particularly from about nucleotide position 344 to about nucleotide position 1306 of SEQ ID NO:9, or from about nucleotide position 1 through about nucleotide position 1092 as set forth in SEQ ID NO:32, or more particularly from about nucleotide position 130 to about nucleotide position 1092 as set forth in SEQ ID NO:32, contain one or more contiguous nucleotide sequences that are sufficiently identical to one or more contiguous nucleotide sequences of SEQ ID NO:3, SEQ ID NO:5, SEQ ID NO:7, SEQ ID NO:32, or SEQ ID NO:9, such that an alignment is able to take place between the two sequences, and the two sequences are then able, under stringent conditions, to form hydrogen bonds with corresponding bases on the opposite strand to form a duplex molecule that is sufficiently stable under the stringent conditions for a long enough period of time to be detectable using methods well known in the art. Such substantially homologous sequences are preferably from about 67% to about 70% identical, or more preferably from about 80% to about 85% identical, or most preferable from about 90% to about 95% identical, to about 99% identical or greater to the referent nucleotide sequences as set forth in SEQ ID NO:32, SEQ ID NO:3, SEQ ID NO:5, SEQ ID NO:7, or SEQ ID NO:9, or the complements thereof. In addition, nucleotide sequences that encode insecticidal proteins isolatable from Bacillus thuringiensis or other Bacillus species strains and the like, that hybridize under stringent conditions to SEQ ID NO:2 are also envisioned to exhibit substantial homology with the above listed referent nucleotide sequences that hybridize under stringent conditions to the tic901, tic1201, tic407, tic417, and tic431 coding sequence as set forth in SEQ ID NO:3 or SEQ ID NO:5, SEQ ID NO:7, SEQ ID NO:9, and SEQ ID NO:32 respectively or the complements thereof. Such nucleotide sequences are referred to herein as homologs of SEQ ID NO:3 and the like and comprise SEQ ID NO:5, SEQ ID NO:7, SEQ ID NO:9, and SEQ ID NO:32 and related sequences and homologues thereof.

With reference to polypeptide sequences, the terms "substantial identity" or "substantial similarity" refers to polypeptides which exhibit a substantial amino acid sequence identity or a substantial amino acid sequence similarity to a referent amino acid sequence, particularly in view of the fact, as described herein, that certain amino acids may be substituted by other amino acids based on hydropathicity or hydrophilicity indices and still result in a protein with similar biological activity, i.e. still obtain a biological functionally equivalent protein. Therefore, an amino acid sequence exhibiting a substantial identity or a substantial similarity to a referent polypeptide or amino acid sequence would exhibit from about 30% to about 50% amino acid sequence identity to the referent sequence, and more preferably exhibit from about 70% to about 80% amino acid sequence identity to the referent sequence, more preferably from about 86% to about 90% amino acid sequence identity to the referent sequence, and even more preferably from about 95% to about 99% amino acid sequence identity to the referent polypeptide sequence. More specifically, the inventors envision peptides exhibiting insecticidal activity that are related to the peptides of the present invention exhibit substantial peptide identity or substantial peptide similarity to the peptides of the present invention and exhibit at least from about 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, and 99 percent identity or similarity to the referent polypeptide sequences as set forth herein and selected from the group consisting of SEQ ID NO:1, SEQ ID NO:4, SEQ ID NO:6, SEQ ID NO:8, SEQ ID NO:10, and SEQ ID NO:33.

With reference to the proteins of the instant application, the terms "variant amino acid sequence", or "amino acid sequence variant", or "modified amino acid sequence variant" are intended to refer to amino acid sequences that are substantially equivalent to the amino acid sequences of the present invention. For example, a protein produced by the introduction of a restriction site for convenience of molecular manipulations into a coding sequence of the present invention that results in the addition or subtraction of one or more codons without otherwise (1) disrupting the native coding sequence, (2) disrupting the native open reading frame, and (3) disrupting the insecticidal biological activity of the protein, would constitute (a) a variant amino acid sequence compared to the native insecticidal toxin, (b) an amino acid sequence variant compared to the native insecticidal toxin, or (c) a modified amino acid sequence variant compared to the native insecticidal toxin. One skilled in the art would recognize that there are other types of modifications that can be made to the amino acid sequence of the present invention without disrupting the biological activity of the protein. The use of the term "disrupting", with reference to biological activity, is intended to refer to modifications of the native amino acid sequence by insertion or deletion of one or more amino acids, or exchange or substitution of one amino acid for another, which do not decrease the insecticidal biological activity of the protein. Insertions, deletions, and substitutions are within the scope of the present disclosure to the extent that the resulting amino acid sequence variant exhibits insecticidal activity no less than that of the native insecticidal protein. Chimeras of the proteins disclosed herein, fusions of the proteins or parts of the proteins disclosed herein, and permuteins of the proteins disclosed herein are specifically contemplated.

Proteins that are substantially equivalent to the proteins of the instant application are intended to be biologically functionally equivalent. As used herein, the phrase "biological functional equivalents", with respect to the insecticidal proteins of the present invention, are peptides, polypeptides and proteins that contain a sequence or moiety exhibiting sequence similarity to the novel peptides of the present invention, such as a TIC901 protein or insecticidal fragment thereof, or a TIC1201, TIC410, TIC407, or TIC431 protein or insecticidal fragments thereof, and that exhibit the same or similar functional properties as that of the polypeptides disclosed herein, including insecticidal activity. Biological equivalents also include peptides, polypeptides and proteins that react with, i.e. specifically bind to antibodies raised against epitopes present on or within TIC901 and related proteins such as TIC1201, TIC417, TIC407, and TIC431 and insecticidal fragments thereof, and that exhibit the same or similar binding or reactive activity, including to both monoclonal and polyclonal antibodies.

It is also contemplated that the proteins of the present invention could be useful for protecting dicot plants from insect infestation. Such infestations could be the result of coleopteran, dipteran, lepidopteran, or even infestation by mites, mealworms, grubs, or a wide variety of insects that injure the plant by piercing the plant tissues and extracting the nutrients intended for plant growth and development. Modifications to the primary amino acid sequence of the proteins of the present invention could result in a protein that exhibits a host range different from that of the native protein.

The proteins of the present invention, because of their localization into the extracellular space when expressed by *Bacillus* strains, may be useful for targeting other proteins for localization into the extracellular space. For example, the skilled artisan would know to link a first protein that is not normally secreted into the extracellular space to a second protein that is normally secreted into the extracellular space in order to achieve the localization of the first protein into the extracellular space. The proteins of the present invention could be fused by any number of means well known in the art to one or more insecticidal toxins such as crystalline delta-endotoxins to form a chimeric protein that is targeted for secretion into the extracellular space surrounding a particular host cell. It is even envisioned that the secretion event itself could lead to the separation of the two protein parts such that two separate and distinct insecticidal proteins are released into the extracellular space surrounding a particular host cell. The two proteins could either (1) both be toxic to the same insect species but effectuate their insecticidal activity using different modes of action, or (2) each be toxic to different insect species. It is conceivable that any number of insecticidal proteins could be linked end-to-end to the proteins of the present invention to form multimeric chimeras that are targeted to the extracellular space surrounding a particular host cell. Such "other" proteins conceivably could be green fluorescent and related proteins and variants, kinases and phosphatases for modulating cell signaling processes, nucleases, lipases, herbicide tolerance proteins expressed from genes such as gox, various epsps homologues, bar and homologues and the like, PhnO, NptII, Aad, and the like. All of these proteins could be used as selectable markers as well, particularly when linked to a gene encoding one or more of the proteins of the present invention, to track the presence of the genes encoding one or more of the proteins of the present invention in a plant or other host cell.

The proteins of the present invention could be targeted for import into a subcellular organelle. For example, a first nucleotide sequence encoding a chloroplast or plastid targeting sequence could be operably linked or fused to a second nucleotide sequence encoding an insecticidal protein of the present invention to produce a chimeric precursor protein that is targeted for insertion into the chloroplast or plastid within a plant cell. Expression of such chimeric proteins would result in the import of the proteins of the present invention into the plant chloroplast or plastid, resulting in the localization of the insecticidal toxin or insecticidal fragment thereof into the chloroplast or plastid. Additionally, a nucleotide sequence encoding one or more proteins of the present invention could be localized to the chloroplast or plastid for expression. The localization of the nucleotide sequences to the plastid or chloroplast could result in the incorporation of the nucleotide sequences into the chloroplast or plastid genome, or could result in the presence of an autonomously replicating nucleic acid sequence encoding the protein of the present invention. In either sense, the proteins of the present invention would be localized to the chloroplast or plastid. As used herein therefore, the phrase "chloroplast or plastid localized" refers to a biological molecule, either polynucleotide or polypeptide, which is positioned within the chloroplast or plastid such that the molecule is isolated from the cellular cytoplasmic milieu, and functions within the chloroplast or plastid cytoplasm to provide the effects claimed in the instant invention. Localization of a biological molecule to the chloroplast or plastid can occur, with reference to polynucleotides, by artificial mechanical means such as electroporation, mechanical microinjection, or by polynucleotide coated microprojectile bombardment, or with reference to polypeptides, by secretory or import means wherein a natural, synthetic, or heterologous plastid or chloroplast targeting peptide sequence is used which functions to target, insert, assist, or localize a linked polypeptide into a chloroplast or plastid.

As used herein, the phrase "operatively linked" or "operably linked" refers to nucleic acid coding segments connected in frame so that the properties of one influence the expression of the other. These phrases and groups of words can also be used to refer to amino acid sequences which exhibit some function when linked to another amino acid sequence, for example, a signal peptide when linked to a protein of interest is referred to as being operably linked to the protein of interest for the purpose of targeting the protein of interest to the secretory apparatus of the host cell in which the protein is produced, or to a subcellular compartment such as an endoplasmic reticulum, a chloroplast or a plastic, a mitochondrion, a vacuole, the nucleus or nucleolus, or other subcellular compartment and the like.

For the purposes of the present invention, the word "gene" refers to a nucleotide sequence that contains an open reading frame encoding a TIC901 protein, a TIC1201 protein, a TIC417 protein, a TIC407 protein, a TIC431 protein, or an insecticidal fragment thereof, or an amino acid sequence variant thereof, or a related protein homolog or insecticidal fragment thereof or amino acid sequence variant thereof that is at least operably linked to a promoter sequence and a transcription termination sequence, wherein the promoter and transcription termination sequences are functional in the host cell in which the protein is produced. As used herein, "structural gene" refers to a gene that is expressed to produce a polypeptide. A structural gene of the present invention can contain, in addition to promoter and transcription termination sequences, five prime untranslated sequences, intronic sequences, and enhancer elements that function in plants in particular, and preferably those that are derived from maize or other monocotyledonous plants that, when linked together in proper sequence with one or more coding sequences of the present invention result in improved levels of expression in particular plant tissues, and preferably result in enhanced expression in root tissues of maize plants.

Nucleotide sequence information provided by the present invention allows for the preparation of relatively short DNA sequences, referred to herein as probes or primers, having the ability to specifically hybridize to sequences of the selected polynucleotides disclosed herein. Such nucleic acid probes of an appropriate length are prepared based on a consideration of selected polypeptide sequences encoding the insecticidal polypeptides of the present invention, e.g., a sequence such as that shown in SEQ ID NO:2, all or a probe specific part of SEQ ID NO:3 from about nucleotide 153 to about nucleotide 1,253; all or a probe specific part of SEQ ID NO:5 from about nucleotide 530 to about nucleotide 1621, all or a probe specific part of SEQ ID NO:7, all or a probe specific part of SEQ ID NO:9, all or a probe specific part of SEQ ID NO:32, or all or a probe specific or primer specific part of the sequences selected from the group consisting of SEQ ID NO:11, SEQ ID NO:12, SEQ ID NO:13, SEQ ID NO:15, SEQ ID NO:16, SEQ ID NO:17, SEQ ID NO:18, SEQ ID NO:19, SEQ ID NO:20, SEQ ID NO:21, and SEQ ID NO:22, and complements thereof and the like. Reference to the phrase "all or a probe specific part of" is intended to refer to a probe comprising at least a 15 to 50, more or less, contiguous nucleotide sequence selected from the group of nucleotides set forth in a particular referent sequence such as SEQ ID NO:2, SEQ ID NO:3, SEQ ID NO:5, SEQ ID NO:7, SEQ ID NO:9, SEQ ID NO:11, SEQ ID NO:12, SEQ ID NO:13, SEQ ID NO:15, SEQ ID NO:16, SEQ ID NO:17, SEQ ID NO:18, SEQ ID NO:19, SEQ ID NO:20, SEQ ID NO:21, SEQ ID NO:22, and SEQ ID NO:32 and complements thereof and the like. The ability of such nucleic acid probes to specifically hybridize to a nucleotide sequence encoding an insecticidal polypeptide sequence lends to them particular utility in a variety of embodiments. Most importantly, the probes may be used in a variety of assays for detecting the presence of complementary sequences in a given sample.

In certain embodiments, it is advantageous to use oligonucleotide primers. The sequence of such primers is designed using a polynucleotide of the present invention for use in detecting, amplifying or modifying a defined segment of an insecticidal protein coding sequence from *B. thuringiensis* or from *Bacillus sphaericus* and the like using thermal amplification technology. Segments of nucleotide sequences related to the polynucleotides encoding the insecticidal polypeptides of the present invention may also be isolated and characterized using thermal amplification technology and such primers.

To provide certain of the advantages in accordance with the present invention, a preferred nucleic acid sequence employed for hybridization studies or assays or as a primer includes sequences that are complementary to at least a 14 to 30 or more contiguous stretch of nucleotides of a polynucleotide sequence encoding all or a part of an insecticidal protein of the present invention, such as that shown in SEQ ID NO:2, SEQ ID NO:3, SEQ ID NO:5, SEQ ID NO:7, SEQ ID NO:9, SEQ ID NO:11, SEQ ID NO:12, SEQ ID NO:13, SEQ ID NO:15, SEQ ID NO:16, SEQ ID NO:17, SEQ ID NO:18, SEQ ID NO:19, SEQ ID NO:20, SEQ ID NO:21, SEQ ID NO:22, and SEQ ID NO:32 and complements thereof and the like.

A primer or probe size of at least 14 nucleotides in length helps to ensure that the fragment will be of sufficient length to form a duplex molecule that is both stable and selective. Molecules having complementary sequences over segments greater than 14 bases in length are generally preferred. In order to increase stability and selectivity of the hybrid, and thereby improve the quality and degree of specific hybrid molecules obtained, one will generally prefer to design nucleic acid molecules having tic901-complementary sequences and the like of 14 to 20 nucleotides, or even longer where desired; or having tic1201-complementary sequences and the like of 14 to 20 nucleotides, or even longer where desired; tic417-complementary sequences and the like of 14 to 20 nucleotides, or even longer where desired; tic407-complementary sequences and the like of 14 to 20 nucleotides, or even longer where desired; and tic431-complementary sequences and the like of 14 to 20 nucleotides, or even longer where desired. Such fragments may be readily prepared by, for example, directly synthesizing the fragment by chemical means, by application of nucleic acid reproduction technology, or by excising selected DNA fragments from recombinant sequences localized in plasmids or other vectors containing appropriate inserts and suitable restriction sites.

The inventors herein have also designed degenerate universal probes and primers for use in identifying naturally occurring nucleotide sequences encoding amino acid sequences derived from insecticidal proteins that are homologues of the proteins of the present invention. The nucleotide sequences identified using the exemplified probes and primers set forth in SEQ ID NO:23-SEQ ID NO:29 hybridize under stringent conditions to the nucleotide sequences encoding secreted insecticidal proteins as set forth herein.

The amino acid sequences alignment as shown in FIG. 1 provided a basis for identifying amino acid sequences that are highly conserved between the four aligned insecticidal precursor proteins. For example, the amino acid sequence as set forth in SEQ ID NO:4 from about amino acid seventy-five (75) through about amino acid eighty-three (83) is a sequence that is conserved in both sequence and position within the primary sequences of the TIC901, TIC1201, TIC407, TIC417, and TIC431 proteins. This is described herein as a 'first conserved amino acid sequence'. The amino acid sequence from about amino acid one-hundred-forty-seven (147) through about one-hundred-fifty-three (153) as set forth in SEQ ID NO:4 is also conserved in both sequence and position within the primary sequences of the TIC901, TIC1201, TIC407, TIC431, and TIC417 proteins. This is described herein as a 'second conserved amino acid sequence'. Similarly, the amino acid sequence from about amino acid two-hundred-seventy-five (275) through about amino acid two-hundred-eighty-three (283) as set forth in SEQ ID NO:4 is also conserved in both sequence and position within the primary sequences of the TIC901, TIC1201, TIC407, TIC431, and TIC417 proteins. This is described herein as a 'third conserved amino acid sequence'. These sequences each correspond to substantially conserved but slightly degenerate nucleotide sequences in the respective coding sequence for each protein that can be used either as a probe sequence or as a primer sequence for identifying the presence of a nucleotide segment homologous to a sequence comprising at least a fourteen base sequence selected from the group consisting of SEQ ID NO:3, SEQ ID NO:5, SEQ ID NO:7, SEQ ID NO:32, and SEQ ID NO:9 or the complement thereof. For example, a thermal amplification reaction that uses a degenerate primer sequence, the synthesis of which is based on the compiled sequences selected from SEQ ID NO:3, SEQ ID NO:5, SEQ ID NO:7, SEQ ID NO:32, and SEQ ID NO:9, and the complements thereof when inverse thermal amplification is contemplated, corresponding to the sequence coding for the 'first conserved amino acid sequence' as described above, comprises a twenty-six-mer (26mer) oligonucleotide corresponding to the first conserved nucleotide sequence, for example as set forth in SEQ ID NO:3 from about nucleotide position three-hundred-seventy-five (375) to about nucleotide position four-hundred-one (401), would be one of the degenerate sequences that could be used for probing a sample for the presence of a nucleotide sequence homologue corresponding to a sequence that hybridizes to the corresponding sequence within SEQ ID NO:3, SEQ ID NO:5, SEQ ID NO:7, SEQ ID NO:32, and SEQ ID NO:9. Alternatively, the oligonucleotide sequence could be used as one of a pair of oligonucleotide primers in a thermal amplification reaction for producing an amplicon sequence that would hybridize to the corresponding sequences within one or more of the sequences as set forth herein, for example, within a sequence comprising SEQ ID NO:3, SEQ ID NO:5, SEQ ID NO:7, SEQ ID NO:32, and SEQ ID NO:9, under stringent hybridization conditions.

The inventors herein have therefore constructed sets of primers and probes that can be used alone or in combination with each other for identifying sequences that are related to the proteins of the present invention, including TIC901, TIC201, TIC407, TIC431, and TIC417, that encode secreted insecticidal proteins, and that hybridize to one or more of the sequences disclosed herein under stringent hybridization conditions. One set of primers consists of degenerate oligonucleotide sequences that correspond to sequences as set forth in SEQ ID NO:23 through SEQ ID NO:25. SEQ ID NO:23 corresponds to a set of degenerate oligonucleotide sequences corresponding to from about nucleotide position three-hundred-seventy-five (375) to about nucleotide position four-hundred-one (401) as set forth in SEQ ID NO:3, from about nucleotide position seven-hundred-fifty-two (752) to about nucleotide position seven-hundred-seventy-eight (778) as set forth in SEQ ID NO:5, from about nucleotide position three-hundred-ninety-one (391) to about nucleotide position four-hundred-seventeen (417) as set forth in SEQ ID NO:7, from about nucleotide position four-hundred-thirty-seven (437) to about nucleotide position four-hundred-sixty-three (463) as set forth in SEQ ID NO:9, and from about nucleotide position two-hundred-twenty-three (223) to about nucleotide position two-hundred-forty-nine (249) as set forth in SEQ ID NO:32. All possible combinations of nucleotide sequences encoding the corresponding 'first conserved amino acid sequence' described herein above that would reasonably be expected to be present within a Bacillus species are contemplated therein as set forth in SEQ ID NO:23. SEQ ID NO:24 and SEQ ID NO:25 are degenerate oligonucleotide sequences comprising subsets of the sequences corresponding to SEQ ID NO:23, and like SEQ ID NO:23, contain codons that are biased toward the codon usage preference of Bacillus coding sequences.

A second set of primers and probes that can be used for identifying sequences as described herein that are related to SEQ ID NO:3, SEQ ID NO:5, SEQ ID NO:7, SEQ ID NO:9, and SEQ ID NO:32 and that encode secreted insecticidal proteins is contemplated by the degenerate sequences as set forth in SEQ ID NO:26. These oligonucleotide sequences correspond to the range of anticipated nucleotide sequences that would be preferred by a Bacillus species for encoding the amino acid sequence described herein above as the 'second conserved amino acid sequence', and further correspond to from about nucleotide position five-hundred-ninety-one (591) through about nucleotide position six-hundred-eleven (611) as set forth in SEQ ID NO:3, from about nucleotide position nine-hundred-sixty-eight (968) to about nucleotide position nine-hundred-eighty-eight (988) as set forth in SEQ ID NO:5, from about nucleotide position six-hundred-sever (607) to about nucleotide position six-hundred-twenty-seven (627) as set forth in SEQ ID NO:7, from about nucleotide position six-hundred-fifty-three (653) to about nucleotide position six-hundred-seventy-three (673) as set forth in SEQ ID NO:9, and from about nucleotide position four-hundred-thirty-nine (439) to about nucleotide position four-hundred-fifty-six (456) as set forth in SEQ ID NO:32. All possible combinations of nucleotide sequences encoding the corresponding 'second conserved amino acid sequence' described herein above that would reasonably be expected to be present within a Bacillus species are contemplated therein as set forth in SEQ ID NO:26 and the codons selected for incorporation into the degenerate oligonucleotide sequence are biased toward the codon usage preference of Bacillus coding sequences.

Still, a third set of primers and probes that can be used for identifying sequences as described herein that are related to SEQ ID NO:3, SEQ ID NO:5, SEQ ID NO:7, SEQ ID NO:9, and SEQ ID NO:32 and that encode secreted insecticidal proteins are contemplated by the degenerate sequences as set forth in SEQ ID NO:27-SEQ ID NO:29. These oligonucleotide sequences correspond to the range of anticipated nucleotide sequences that would be preferred by a Bacillus species for encoding the amino acid sequence described herein above as the 'third conserved amino acid sequence', and further correspond to the reverse complement of the nucleotide sequence from about nucleotide position nine-hundred-seventy-five (975) to about nucleotide position one-thousand-one (1,001) as set forth in SEQ ID NO:3, the reverse complement of the nucleotide sequence from about nucleotide position one-thousand-three-hundred-fifty-two (1,352) to about nucleotide position one-thousand-three-hundred-seventy-eight (1,378) as set forth in SEQ ID NO:5, the reverse complement of the nucleotide sequence from about nucleotide position nine-hundred-ninety-one (991) to about nucleotide position one-thousand-seventeen (1,017) as set forth in SEQ ID NO:7, the reverse complement of the nucleotide sequence from about nucleotide position one-thousand-thirty-seven (1,037) to about nucleotide position one-thousand-sixty-three (1,063) as set forth in SEQ ID NO:9, and the reverse complement of the nucleotide sequence from about nucleotide position eight-hundred-twenty-three (823) to about nucleotide position eight-hundred-forty-six (846) as set forth in SEQ ID NO:32. All possible combinations of oligonucleotide sequences encoding the corresponding 'third conserved amino acid sequence' described herein above that would reasonably be expected to be present within a Bacillus species are contemplated therein as set forth in SEQ ID NO:27. SEQ ID NO:28 and SEQ ID NO:29 are also degenerate nucleotide sequences comprising subsets of the sequences corresponding to SEQ ID NO:27, and like SEQ ID NO:27, contain codons that are biased toward the codon usage preference of Bacillus coding sequences.

Any of the sequences contemplated by the sequences as set forth in SEQ ID NO:23 through SEQ ID NO:29 can be used alone as a probe for identifying the presence of a nucleotide sequence in a sample that encodes a secreted insecticidal protein related to any of the proteins exemplified herein, in particular a nucleotide sequence that hybridizes to one or more of the nucleotide sequences of the present invention, including but not limited to SEQ ID NO:2, SEQ ID NO:3, SEQ ID NO:5, SEQ ID NO:7, SEQ ID NO:9, SEQ ID NO:32 and any of the nucleotide sequences set forth herein as probes and/or primers selected from the group consisting of SEQ ID NO:11, SEQ ID NO:12, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, and SEQ ID NO:29.

Alternatively, and preferably, various combinations of the probes and primers set forth herein can be used together in a thermal amplification reaction to produce one or more amplicons that are diagnostic for the presence of a nucleotide sequence in a sample that encodes a secreted insecticidal protein related to the proteins of the present invention in that the nucleotide sequence encoding the insecticidal protein hybridizes to one or more of the nucleotide sequences exemplified herein comprising SEQ ID NO:2, SEQ ID NO:3, SEQ ID NO:5, SEQ ID NO:7, SEQ ID NO:9, SEQ ID NO:11, SEQ ID NO:12, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, and SEQ ID NO:32 or the complements thereof, under stringent hybridization conditions. For example, combining one or more of the nucleotides as set forth in SEQ ID NO:23-25, such as primer prJWP200 (SEQ ID NO:23), with one or more of the nucleotides as set forth in SEQ ID NO:27-29, such as primer prJWP204 (SEQ ID NO:27), each at a concentration of at least about 1 pico-mole per micro-liter in a thermal amplification reaction containing 1×TAQ amplification buffer, 0.2 molar each deoxy-nucleotide tri-phosphate (dATP, dTTP, dCTP, and dGTP), 2 milli-molar $MgCl_2$, 2 units TAQ polymerase, and from about ten (10) to about one hundred (100) nano-grams of a sample containing DNA template in which one or more of the sequences of the present invention encoding a secreted insecticidal protein or fragment thereof is present, results in the synthesis of a double-stranded DNA fragment that is an amplicon comprising from about 600 to about 650 base pairs, more preferably from about 615 to about 630 base pairs, and even more preferably from about 623 to about 626 base pairs. An amplicon of this size is diagnostic for the presence of a nucleotide sequence in a sample encoding all or part of an secreted insecticidal protein that is related to one or more of the proteins of the present invention, and is of a size that can reasonably be anticipated, in particular if the thermal amplification cycle conditions consist of an initial denaturation of about 2 minutes at 94° C. followed by 35 cycles of a denaturation step of 30 seconds at 94° C., an annealing step of 30 seconds at 50° C., and an extension step of 45 seconds at 72° C. followed by a final extension step of 7 minutes at 72° C. The temperature of the annealing step should be decreased by 0.3° C. for each successive cycle so that the final annealing temperature is about 39.8° C. Also, combining one or more of the nucleotides as set forth in SEQ ID NO:26 such as prJWP203 with one or more primers as set forth in SEQ ID NO:27-29 in a similar thermal amplification reaction would result in the synthesis of an amplicon of from about 400 to about 415 base pairs, or an amplicon of from about 400 to about 415 base pairs, or from about 405 to about 410 base pairs, that is diagnostic for the presence of a nucleotide sequence in a sample that encodes a secreted insecticidal protein related the proteins of the present invention.

Following these conditions, and using the primers prJWP200 (SEQ ID NO:23) and prJWP204 (SEQ ID NO:27) along with genomic DNA from strain EG2158, resulted in the production of an amplicon segment corresponding to about 620 base pairs. Several individual clones representing this segment were isolated at random from the amplification reaction and the nucleotide sequence of each individual clone was obtained. As expected, a first sequence identical to the corresponding nucleotide sequence for TIC901 was identified in the clone population (not including the primer sequences at either end of the clone, from about nucleotide position four-hundred-two (402) through about nucleotide position nine-hundred-seventy-four (974) as set forth in SEQ ID NO:3). Also, and as expected, a second sequence identical to the corresponding nucleotide sequence for TIC417 was identified in the clone population (not including the primer sequences at either end of the clone, from about nucleotide position four-hundred-sixty-four (464) through about nucleotide position one-thousand-thirty-six (1,036) as set forth in SEQ ID NO:9).

Surprisingly, a third sequence (SEQ ID NO:30) was also identified in the clone population that did not correspond identically to any of the sequences set forth herein but which was substantially similar in nucleotide sequence to each of the sequences of the present invention, including the corresponding coding sequence within the tic901, tic1201, tic407, tic417, and tic431 coding sequences. As exemplified herein, it was quite unexpected to find the tic417 coding sequence in the strain EG2158 genomic DNA. However, it was even more surprising to identify yet a third nucleotide sequence from the EG2158 genome that likely corresponds to a nucleotide segment that encodes yet a third secreted insecticidal protein different from TIC901, TIC1201, TIC407, TIC417, and TIC431, but which is sufficiently similar in sequence to the proteins of the present invention to be classified as one of the species within the genus of secreted insecticidal proteins encoded by a nucleotide sequence that hybridizes to one or more of the sequences set forth herein, and is exemplary of the novelty and utility of the degenerate oligonucleotide probes and primers exemplified herein for use in identifying sequences that encode secreted insecticidal proteins and that hybridize under stringent conditions to the related tic901, tic1201 tic07, tic417, and tic431 coding sequences as set forth herein.

The amino acid sequence encoded by the uninterrupted open reading frame as set forth in SEQ ID NO:30, which has had the twenty-six-mer degenerate oligonucleotide sequences deleted from both the 5' and 3' ends, is set forth in SEQ ID NO:31. The amino acid sequence set forth in SEQ ID NO:31 is substantially similar to the amino acid sequence of TIC901 from about amino acid position eighty-five (85) through about amino acid position two-hundred-seventy-four (274) as set forth in SEQ ID NO:4, containing only two (2) amino acids that are different from the analogous sequence in SEQ ID NO:4, corresponding to an about 98.9% identity between SEQ ID NO:31 and the corresponding sequence in SEQ ID NO:4. The amino acid sequence set forth in SEQ ID NO:31 is substantially similar to the amino acid sequence of TIC1201 from about amino acid position eighty-five (85) through about amino acid position two-hundred-seventy-four (274) as set forth in SEQ ID NO:6, containing only thirteen (13) amino acids that are different from the analogous sequence in SEQ ID NO:6, corresponding to an about 93.2% identity between SEQ ID NO:31 and the corresponding sequence in SEQ ID NO:6. The amino acid sequence set forth in SEQ ID NO:31 is substantially similar to the amino acid sequence of TIC417 from about amino acid position eighty-five (85) through about amino acid position two-hundred-seventy-four (274) as set forth in SEQ ID NO:10, containing only thirty (30) amino acids that are different from the analogous sequence in SEQ ID NO:10, corresponding to an about 83.7% identity between SEQ ID NO:31 and the corresponding sequence in SEQ ID NO:10. The amino acid sequence set forth in SEQ ID NO:31 is also substantially similar to the amino acid sequence of TIC401 from about amino acid position eighty-five (85) through about amino acid position two-hundred-seventy-four (274) as set forth in SEQ ID NO:8, containing forty-one (41) amino acids that are different from the analogous sequence in SEQ ID NO:8, corresponding to an about 78.4% identity between SEQ ID NO:31 and the corresponding sequence in SEQ ID NO:8. The amino acid sequence as set forth in SEQ ID NO:31 is also substantially similar to the amino acid sequence as set forth in SEQ ID NO:33 (TIC431).

The present invention also contemplates an expression vector comprising a polynucleotide of the present invention. Thus, in one embodiment an expression vector is an isolated and purified DNA molecule comprising a promoter operatively linked to a coding region that encodes a polypeptide of the present invention, which coding region is operatively linked to a transcription-terminating region, whereby the promoter drives the transcription of the coding region. The coding region may include a segment encoding a *B. thuringiensis* insecticidal toxin of the present invention and a segment encoding a chloroplast or plastid targeting peptide. The DNA molecule comprising the expression vector may also contain a functional intron sequence positioned either upstream of the coding sequence or even within the coding sequence, and may also contain a five prime (5') untranslated leader sequence (i.e., a UTR or 5'-UTR) positioned between the promoter and the point of translational initiation.

As used herein and with reference to promoter elements, the terms "operatively linked" or "operably linked" are intended to indicate that a nucleotide sequence that contains a promoter, i.e. a genetic element that functions in a particular host cell to drive the initiation of transcription, is connected to a coding region in such a way that the transcription of that coding region is controlled and substantially regulated by that promoter. Means for operatively linking a promoter to a coding region are well known in the art. Promoters that function in bacteria are well known in the art. Exemplary and preferred promoters for the *B. thuringiensis* crystal proteins include the sigA, sigE, and sigK gene promoters. Alternatively, native, mutagenized, heterologous, or recombinant promoters derived from *Bacillus thuringiensis* or other *Bacillus* species can be used for achieving expression of the proteins of the present invention in a *Bacillus* species strain.

Where a nucleotide sequence encoding all or an insecticidal part of a protein of the present invention is to be used to transform a plant, a promoter is selected that has the ability to drive expression of the coding sequence in that particular species of plant. Promoters that function in different plant species are also well known in the art. Promoters useful for expression of polypeptides in plants are those which are inducible, viral, synthetic, or constitutive as described in Odell et al. (Nature 313:810-812, 1985), and/or promoters that are temporally regulated, spatially regulated, and spatio-temporally regulated. Preferred promoters include the enhanced CaMV35S promoters, and the FMV35S promoter. For optimum control of rootworm species by expression of the proteins of the present invention in plants, it is preferable to achieve the highest levels of expression of these proteins within the roots of maize plants. A number of root enhanced promoters have been identified and are known in the art. (Lu et al., J. Plant Phys., 2000, 156(2):277-283; U.S. Pat. No. 5,837,848; U.S. Pat. No. 6,489,542). Substantial temporal or spatial regulation refers to the expression of a gene within a plant or plant tissue from a plant operable promoter. With reference to temporal regulation, a promoter may be regulated for expression only during specific times during plant cell or tissue or even whole plant growth and development. A promoter which is actively expressing one or more genes only during seed germination would be one example of temporal regulation. Other examples could include promoters which are actively expressing one or more genes only during times when the plant, plant cell or plant tissue is exposed to certain light intensities or during total darkness. Substantial temporal regulation refers to a promoter which is actively expressed at a certain time but which may or may not be completely suppressed at other times, such that expression may still be detected by monitoring for the presence of some indicator such as an enzyme produced from a coding sequence linked to such promoter, or as measured by the increase or decrease in some gene product such as an mRNA produced at various times throughout plant growth, differentiation, and development and/or in response to various environmental stimuli. Substantial spatial regulation refers to the expression of a gene linked to a promoter from which expression proceeds only during growth and development of certain cells or tissues within a plant. For example, a tapetal promoter would only be expected to be substantially spatially expressed during flower growth and development. Similarly, a root specific or root enhanced promoter would only be expected to be substantially spatially expressed from within root cells or root tissues. Substantially spatially regulated also refers to the level of expression from a particular tissue specific promoter in that particular tissue and as related to levels of expression from that or a similar promoter in other tissues, wherein expression may also be detected in tissues other than the particular tissue in which the promoter expression is preferred, but at significantly lower expression levels as measured by the production of an enzyme produced from a coding sequence linked to the promoter or by the appearance of some detectable gene product. Promoters can also be both substantially temporally and substantially spatially regulated together and simultaneously in a coordinately regulated manner. Other promoters specifically intended to be within the scope of the present invention include but are not limited to the ubiquitin promoter, the sugarcane bacilliform DNA virus promoter, the ribulose bis-phosphate carboxylase large subunit promoter, among others.

Preferred intron sequences for achieving optimum expression of non-naturally occurring nucleotide sequences in monocotyledonous plants may also be included in the DNA expression construct. Such an intron is typically placed near the 5'-end of the mRNA within or immediately downstream of an untranslated sequence. The intron could be obtained from, but not limited to, a set of introns consisting of the maize Heat Shock Protein (HSP) 70 intron (U.S. Pat. No. 5,424,412; 1995), the rice Act1 intron (McElroy et al., Plant Cell 2:163-171, 1990), the Adh intron 1 (Callis et al., Genes & Develop. 1:1183-1200, 1987), or the sucrose synthase intron (Vasil et al., Plant Phys. 91:1575-1579, 1989).

Another element that functions to regulate or to modulate gene expression is the DNA sequence between the transcription initiation site and the start of the coding sequence, termed the untranslated leader sequence (UTL). Compilations of leader sequences have been made to predict optimum or sub-optimum sequences and generate "consensus" and preferred leader sequences (Joshi, Nucl. Acids Res. 15:9627-9640, 1987). Preferred-leader sequences are contemplated to include those that comprise sequences predicted to direct optimum expression of the linked structural gene, i.e. to include a preferred consensus leader sequence that increases or maintains mRNA stability and prevents inappropriate initiation of translation. The choice of such sequences will be known to those of skill in the art in light of the present disclosure. Sequences that are derived from genes that are highly expressed in plants, and in particular in maize will be most preferred. One particularly useful leader is the petunia HSP70 leader.

Transcription enhancers or duplications of enhancers could be used to increase expression. These enhancers often are found 5' to the start of transcription in a promoter that functions in eukaryotic cells, but can often be inserted in the forward or reverse orientation 5' or 3' to the coding sequence. Examples of enhancers include elements from the CaMV 35S promoter, octopine synthase genes (Ellis et al., EMBO Journal 6:11-16, 1987), the rice actin gene, and promoter from non-plant eukaryotes (e.g., yeast; Ma et al., Nature 334:631-633, 1988).

RNA polymerase transcribes a nuclear genome DNA coding sequence through a site where polyadenylation occurs. Typically, DNA sequences located a few hundred base pairs downstream of the polyadenylation site serve to terminate transcription. Those DNA sequences are referred to herein as transcription-termination regions. Those regions are required for efficient polyadenylation of nuclear transcribed messenger RNA (mRNA). For coding sequences introduced into a chloroplast or plastid, or into a chloroplast or plastid genome, mRNA transcription termination is similar to methods well known in the bacterial gene expression art. For example, either in a polycistronic or a monocistronic sequence, transcription can be terminated by stem and loop structures or structures similar to bacterial rho dependent sequences.

Expression constructs will typically include a coding sequence exemplified in the present invention or a derivative thereof along with a 3' end DNA sequence that functions as a signal to terminate transcription and, in constructs intended for expression from the plant nuclear genome, allow for the 3' end polyadenylation of the resultant RNA transcript. The most preferred 3' elements are contemplated to be those from the nopaline synthase gene of *A. tumefaciens* (nos 3'end), the terminator for the T7 transcript from the octopine synthase gene of *A. tumefaciens*, and the pea RUBISCO synthase E9 gene (E9 3') 3' non-translated transcription termination and polyadenylation sequence. These and other 3' end regulatory sequences are well known in the art.

Preferred plant transformation vectors include those derived from a Ti plasmid of *Agrobacterium tumefaciens*, as well as those disclosed, e.g., by Herrera-Estrella (Nature 303: 209-213, 1983), Bevan (Nature 304:184-187,1983); Klee (Bio/Technol. 3:637-642, 1985) and Eur. Pat Appl. No. EP 0120516 (each specifically incorporated herein by reference).

The present invention discloses isolated and purified nucleotide sequences encoding insecticidal proteins derived from *Bacillus* species, and particularly from *Bacillus thuringiensis* species. In particular, the *B. thuringiensis* strains 86833, EG2158, EG3618, EG6489, EG6561, EG6618, and EG4653 are each shown herein to produce one or more soluble insecticidal proteins that are localized to culture supernatants (see Table 1 except for EG4653 which is described in detail in Example 11).

The *B. thuringiensis* strains and other bacterial strains described herein may be cultured using conventional growth media and standard fermentation techniques. The *B. thuringiensis* strains harboring one or more tic901, tic1201, tic407, tic417, tic431 or related genes may be fermented as described herein until the cultured *B. thuringiensis* cells reach the stage of their growth cycle when the TIC901, TIC1201, TIC407, TIC417, TIC431 and/or related proteins are produced.

Subject cultures have been deposited under conditions that assure that access to the culture will be available to authorized parties during the pendency of this patent application or patents issued. However, it should be understood that the availability of a deposit does not constitute a license to practice the subject invention in derogation of patent rights granted by governmental action.

Further, these microorganism deposits have been made under the provisions of the "Budapest Treaty on the International Recognition of the Deposit of Microorganism for the Purposes of Patent Procedure." The subject culture deposits will be stored and made available to the public in accord with the provisions of the Budapest Treaty, i.e., it will be stored with all the care necessary to keep it viable and uncontaminated for a period of at least five years after the most recent request for the furnishing of a sample of the deposits, and in any case, for a period of at least 30 (thirty) years after the date of deposit or for the enforceable life of any patent which may issue disclosing the culture. The depositor acknowledges the duty to replace the deposits should the depository be unable to furnish a sample when requested, due to the conditions of the deposits. AU restrictions on the availability to the public of the subject culture deposit will be irrevocably removed upon the granting of a patent disclosing it.

TIC901, TIC1201, TIC407, TIC417, TIC431 and related proteins of the present invention are shown herein to be produced and secreted into the growth media by several stains of *Bacillus thuringiensis*. Fermentations using the strains of the present invention may be continued through the sporulation stage when crystal proteins, if any, are formed along with the spores. The spores and cell debris can be separated from the supernatant by centrifugation, and the spent culture medium can be used to isolate the insecticidal proteins of the present invention. The inventors herein illustrate the method of ammonium sulfate precipitation as one means for concentrating and collecting all or most of the proteins present in the spent and clarified culture medium. However, one skilled in the art will recognize that there are a number of other means available for purifying and isolating the proteins of the present invention. Gel filtration and size exclusion chromatography are two readily available means for extracting proteins directly from the spent media. Spent media can also be desalted and the filtrate used to extract protein using ion exchange columns. Also, affinity columns, containing antibodies that bind specifically to TIC901, TIC1201, TIC407, TIC417, TIC431 or related proteins can be used to purify the proteins of the present invention directly from the media.

The amino acid sequences of the present invention have been compared to the amino acid sequences present in commercially available protein sequence databases, and no significant homologies or similarities have been identified. Based on this analysis, the TIC901, TIC1201, TIC407, TIC417, and TIC431 proteins and related sequences appear to be unique and form the basis for the establishment of a new and separate class of *Bacillus* insecticidal proteins because the proteins of the present invention have not been observed to exhibit any significant relationship to other known insecticidal proteins.

Modification and changes may be made in the structure of the peptides of the present invention and DNA segments that encode them and still obtain a functional molecule that encodes a protein or peptide with desirable characteristics. The biologically functional equivalent peptides, polypeptides, and proteins contemplated herein should possess from about 65 to about 70% or greater amino acid sequence similarity, or from about 80% or greater amino acid sequence similarity, or from about 90% or greater amino acid sequence similarity, to the sequence of, or corresponding moiety within, the fundamental TIC901 amino acid sequence as set forth in SEQ ID NO:4, or the corresponding moiety within the amino acid sequences of TIC1201, TIC407, TIC417, and TIC431 as set forth respectively in SEQ ID NO:6, SEQ ID NO:8, SEQ ID NO:10, and SEQ ID NO:32 and related sequences.

According to the present invention reference to the tic901 gene and encoded protein toxin, includes not only the full length sequences disclosed herein but also fragments of these sequences, natural variants; mutants, and recombinant or genetically engineered derivatives of the tic901 gene comprising SEQ ID NO: 3. Proteins encoded by these sequences should retain essentially the same as or greater characteristic insecticidal properties than those of the TIC901 protein comprising SEQ ID NO:4. The proteins useful in the present invention may also include fusion proteins that retain the characteristic insecticidal properties essentially the same as or greater than those of the TIC901 protein. In some instances, the fusion protein may contain, in addition to the characteristic insecticidal properties of the proteins specifically exemplified herein, another insecticidal activity contributed by the amino acid sequence of the fusion partner. Alternatively, crystallographic analysis of the TIC901 protein or insecticidal variants thereof may provide a means for determining whether the protein would be a candidate for the construction of a permutein that exhibits the same or preferably greater insecticidal activity than the native TIC901 or related protein, and which preferably exhibits improved characteristics related to expression in a preferred host cell such as a plant cell. The same qualities and characteristics apply as well to tic1201, tic407, and tic417; to not only the full length sequences disclosed herein but also fragments of these sequences, natural variants, mutants, and recombinant or genetically engineered derivatives of these genes comprising respectively SEQ ID NO:5, SEQ ID NO:7, SEQ ID NO:9, and SEQ ID NO:32. The proteins encoded by these sequences should retain essentially the same as or greater characteristic insecticidal properties than those of the TIC1201, TIC407, TIC417, and TIC431 proteins comprising respectively SEQ ID NO:6, SEQ ID NO:8, SEQ ID NO:10, and SEQ ID NO:32.

It should be apparent to a person skilled in the art that nucleotide sequences encoding insect inhibitory toxins, and particularly coleopteran inhibitory toxins, can be identified and obtained through several means as disclosed herein. The specific sequences and related sequences as exemplified herein may be obtained from the isolates deposited at a culture depository as described above. These sequences, or insecticidal portions or variants thereof, may also be constructed synthetically, for example, by use of a nucleotide sequence synthesizer. Variations of coding sequences may be readily constructed using standard techniques for making point mutations. Also, fragments of these sequences can be made using commercially available exonucleases or endonucleases according to standard procedures. For example, enzymes such as Bal31 or site-directed mutagenesis may be used to systematically excise nucleotides from the ends of such sequences as exemplified herein or from within the protein coding sequence. Also, nucleotide sequences that encode insecticidally active protein fragments may be obtained using a variety of restriction enzymes, endonucleases, thermal amplification methods, and the like. Proteases such as proteinase K, trypsin, chymotrypsin, pepsin, and the like may be used to directly obtain active fragments of these toxins.

Other toxins and nucleotide sequences encoding such toxins related to the toxins and coding sequences of the present invention can be derived from DNA obtained from *B. thuringiensis, B. laterosperous, B. sphaericus*, and related *Bacillus* species isolates using the teachings provided in the art in combination with the nucleotide sequences disclosed herein. Such toxins and nucleotides sequences that are related to the toxins and coding sequences of the present invention are deemed herein to be equivalent to the toxins and nucleotide sequences of the present invention. By "equivalent" it is meant that a protein exhibits the characteristics of one or more of the proteins described herein, including but not limited to similar insecticidal inhibitory bioactivity, host range of insecticidal bioactivity, exhibits similar antigenic epitopes that cross react with antibodies raised against TIC901, TIC1201, TIC407, and TIC417 and the like, and including related proteins, exhibit a similar size relative to TIC901 and related proteins, exhibit similar expression profiles and characteristics, exhibit a propensity for seclusion to the extracellular environment when expressed in *Bacillus thuringiensis* or related bacterial species, and the like. The phrase "exhibit a propensity for seclusion to the extracellular environment" is intended to include TIC901 and related proteins including but not limited to TIC1201, TIC407, TIC417, and TIC431 and the like that are produced by the bacterium or host cell as a precursor protein that contains an amino acid sequence inked to the insecticidal protein that functions to target the insecticidal protein to a bacterial or host cell secretory apparatus and which, upon contact with the secretory apparatus, is proteolytically cleaved by a signal peptidase, releasing the mature or insecticidal protein into the extracellular environment in the case of a gram positive microbe, at least into the periplasm in the case of a gram negative microbe, and into the endoplasmic reticulum or secretory vesicle or into a subcellular organelle such as a mitochondria or chloroplast or plastic in the case of a fungal or plant or other eukaryotic host cell. Cryptic nucleotide coding sequences are also contemplated to be within the scope of the invention herein.

There are a number of methods for identifying the presence of and obtaining equivalent insecticidal toxins related to the peptides disclosed herein. For example, antibodies to the insecticidal toxins disclosed and claimed herein can be used to identify and isolate other toxins from a mixture of proteins. Specifically, antibodies may be raised to the portions of the toxins that are most constant within the new class of proteins and most distinct from other *B. thuringiensis* toxins. These antibodies can then be used to specifically identify equivalent toxins with the characteristic activity by immuno-precipitation, enzyme linked immuno-sorbent assay (ELISA), or Western blotting. Antibodies to the toxins disclosed herein, or to equivalent toxins, or fragments of these toxins, can readily be prepared using standard procedures in the art. The nucleotide sequences that encode these toxins can then be obtained from the microorganism or other various sources.

A further method for identifying the toxins and genes of the present invention is through the use of oligonucleotide probes. These probes are essentially nucleotide sequences that hybridize under stringent hybridization conditions to the TIC901 coding sequence or a sequence related to a TIC901 coding sequence. As is well known in the art, if a probe molecule and nucleic acid sequence molecule in a sample hybridize by forming a strong enough bond between the two molecules, it can be reasonably assumed that the two molecules exhibit substantial homology. Probe binding is detected using any number of means known in the art including but not limited to fluorescence, luminescence, isotopic, immunological, surface plasmon resonance spectroscopy, and the like. Such probe analysis provides a rapid method for identifying toxin-encoding genes of the present invention. The nucleotide segments that are used as probes according to the invention can be synthesized by use of DNA synthesizers using standard procedures or by other means known in the art. These nucleotide sequences can also be used as PCR primers to amplify nucleotide sequences of the present invention or portions thereof.

Fragments and equivalents of related proteins that retain at least the insecticidal activity of the exemplified toxins are within the scope of the present invention. Also, because of the redundancy of the genetic code, a variety of different DNA sequences can encode the amino acid sequences disclosed herein. It is well within the skill of a person trained in the art to create these alternative DNA sequences encoding the same, or essentially the same, toxins. These variant DNA sequences are within the scope of the present invention.

It is well known in the art that certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the peptide sequences of the disclosed compositions, or corresponding DNA sequences which encode said peptides without appreciable loss of their biological utility or activity. Such substitutions are also known in the art as conservative substitutions.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e. still obtain a biological functionally equivalent protein. In making such changes, the substitution of amino acids whose hydropathic indices are within ±2 is preferred, those that are within ±1 are particularly preferred, and those within ±0.5 are even more particularly preferred.

It is also understood in the art that the substitution of like amino acids can be made effectively on the basis of hydrophilicity. The greatest local average hydrophilicity of a protein, as governed by the hydrophilicity of its adjacent amino acids, correlates with a biological property of the protein (U.S. Pat. No. 4,554,101).

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those that are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take the various foregoing characteristics into consideration are well known to those of skill in the art and include: arginine and lysine; glutamate and aspartate; serine and threonine; glutamine and asparagine; and valine, leucine and isoleucine.

Peptides, polypeptides, and proteins biologically functionally equivalent to TIC901, TIC1201, TIC407, TIC417, TIC431 and related proteins and the like include amino acid sequences containing conservative amino acid changes in the fundamental sequence shown in SEQ ID NO: 4, SEQ ID NO:6, SEQ ID NO:8, SEQ ID NO:10, and SEQ ID NO:33. In particular, with reference to SEQ ID NO:4 from about amino acid 44 through about amino acid 367, with reference to SEQ ID NO:6 from about amino acid 44 through about amino acid 364, with reference to SEQ ID NO:8 from about amino acid 44 through about amino acid 368, with reference to SEQ ID NO:10 from about amino acid 44 through about amino acid 364, and with reference to SEQ ID NO:33 from about amino acid 44 through about amino acid 364, for such amino acid sequences, one or more amino acids in the fundamental sequence can be substituted with another amino acid(s), the charge and polarity of which is similar to that of the native amino acid, i.e. a conservative amino acid substitution, resulting in a silent change.

Substitutes for an amino acid within the fundamental polypeptide sequence can be selected from other members of the class to which the naturally occurring amino acid belongs. Amino acids can be divided into the following four groups: (1) acidic amino acids; (2) basic amino acids; (3) neutral polar amino acids; and (4) neutral non-polar amino acids. Representative amino acids within these various groups include, but are not limited to: (1) acidic (negatively charged) amino acids such as aspartic acid and glutamic acid; (2) basic (positively charged) amino acids such as arginine, histidine, and lysine; (3) neutral polar amino acids such as glycine, serine, threonine, cyteine, cystine, tyrosine, asparagine, and glutamine; (4) neutral nonpolar (hydrophobic) amino acids such as alanine, leucine, isoleucine, valine, proline, phenylalanine, tryptophan, and methionine.

Conservative amino acid changes within the fundamental polypeptide sequences of the present invention can be made by substituting one amino acid within one of these groups with another amino acid within the same group. Biologically functional equivalents of TIC901, TIC1201, TIC407, TIC417, TIC431 and the like and related sequences can have 10 or fewer conservative amino acid changes, more preferably seven or fewer conservative amino acid changes, and most preferably five or fewer conservative amino acid changes. The encoding nucleotide sequence (gene, plasmid DNA, cDNA, or synthetic DNA) will thus have corresponding base substitutions, permitting it to encode biologically functional equivalent forms of the TIC901, TIC1201, TIC407, TIC417, and TIC431 proteins and related sequences.

Amino acid sequence variants of the proteins of the present invention and related sequences can be made by procedures well known in the art. For example, a TIC901 amino acid sequence variant protein that is not secreted into the extracellular milieu can be obtained through ethylmethane sulfonate (EMS) mutagenesis of a nucleotide sequence encoding TIC901. The mutants can also be constructed using ultraviolet light and nitrosoguanidine by procedures well known in the art, or by constructing a coding sequence that lacks all or a part of the coding sequence encoding a signal peptide amino acid sequence.

Site-specific mutagenesis is another technique useful in the preparation of individual peptides, or biologically functional equivalent proteins or peptides, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the sequence targeted for modification. Typically, a primer of from about 17 to about 25 nucleotides in length is preferred, with at least from about 5 to about 10 residues of identity being available on both sides of the target sequence being modified.

The preparation of sequence variants of the selected peptide-encoding DNA segments using site-directed mutagenesis is provided as a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylamine, to obtain sequence variants.

The tic901 and related nucleotide coding sequences isolated from *B. thuringiensis* strains as set forth herein in SEQ ID NO:3, SEQ ID NO:5, SEQ ID NO:7, SEQ ID NO:9, and SEQ ID NO:32 and the like may be used as hybridization probes to identify and isolate naturally occurring variants of these and related nucleotide coding sequences from other strains of *B. thuringiensis* or from other microorganisms such as from microbial species such as *Clostridium, Bacillus, Xenorhabdus*, and *Photorhabdus*. The present invention encompasses nucleotide sequences from microorganisms, where the nucleotide sequences are isolatable by hybridization with all, or part, of the *Bacillus* nucleotide sequence of the invention. Proteins encoded by such nucleotide sequences can be tested for insecticidal activity. The invention also encompasses the proteins encoded by the nucleotide sequences. For example, an alignment of these four nucleotide sequences provides regions of identity that would be preferred for use as probes and primers. Also, an alignment of the amino acid sequences encoded by these and related nucleotide coding sequences provides information regarding regions of identity and/or substantial similarity between the proteins, and provides a basis for constructing probes and or primers that can be used to identify these and other related nucleotide sequences encoding such insecticidal proteins. For example, SEQ ID NO:23-SEQ ID NO:29 are representative of such probes and primers and are exemplified herein in Example 10.

Antibodies raised in response to immune challenge by TIC901, TIC1201, TIC407, TIC417, and TIC431 and the like or related proteins of the present invention may be produced using standard immunological techniques for production of polyclonal antisera and, if desired, immortalizing the antibody-producing cells of the immunized host for sources of monoclonal antibody production. Techniques for producing antibodies to any substance of interest are well known, e.g., as in Harlow and Lane (1988) and as in Goding (1986). For example, antibodies that bind to epitopes on or within TIC901 may be used as probes to identify *B. thuringiensis* strains or other microorganisms that produce variants of TIC901 or related proteins that are encoded by variations of a tic901 or related gene. The present invention encompasses insecticidal proteins that cross-react with antibodies raised against one or more of the insecticidal proteins of the present invention.

The antibodies produced in the present invention are also useful in immunoassays for determining the amount or presence of a TIC901, TIC1201, TIC407, TIC417, and TIC431 or related protein in a biological sample. Such assays are also useful in quality-controlled production of compositions containing one or more of the proteins of the present invention or related proteins. In addition, the antibodies can be used to assess the efficacy of recombinant production of one or more of the proteins of the present invention or a related protein, as well as for screening expression libraries for the presence of a nucleotide sequence encoding one or more of the proteins of the present invention or related protein coding sequences. Antibodies are useful also as affinity ligands for purifying and/or isolating any one or more of the proteins of the present invention and related proteins. The proteins of the present invention and proteins containing related antigenic epitopes may be obtained by over expressing full or partial lengths of a sequence encoding all or part of a protein of the present invention or a related protein in a preferred host cell.

The peptides of the present invention are primarily, though not exclusively, intended for use in plants, and in certain preferred embodiments, nucleotide sequences modified for encoding the proteins of the present invention in plants are contained within one or more plasmid vectors. Such vectors may contain a variety of regulatory and other elements intended to allow for optimal expression of the proteins of the present invention in plant cells. These additional elements may include promoters, terminators, and introns as outlined above. Any vector containing the DNA construct and any regulatory or other elements may be selected from the group consisting of a yeast artificial chromosome, bacterial artificial chromosome, a plasmid, or a cosmid, and the like. Further, the expression vectors themselves may be of a variety of forms. These forms may differ for various reasons, and will likely be comprised of varying components depending upon whether they are intended to be used to transform a monocotyledonous plant or a dicotyledonous plant.

Vectors further envisioned to be within the scope of the present invention include those vectors capable of containing a tic901, tic1201, tic407, tic417 or related nucleic acid compositions disclosed above, as well as any other DNA constructs which further comprise plant-expressible coding regions for other insecticidal proteins derived from *Bacillus* species.

The nucleotide sequence encoding a TIC901 (SEQ ID NO:3 encoding SEQ ID NO:4) or encoding a related peptide sequence such as TIC1201 (SEQ ID NO:5 encoding SEQ ID NO:6), TIC407 (SEQ ID NO:7 encoding SEQ ID NO:8), TIC417 (SEQ ID NO:9 encoding SEQ ID NO:10), and TIC431 (SEQ ID NO:32 encoding SEQ ID NO:33) may be introduced into a variety of microorganism hosts without undue experimentation, using procedures well known to those skilled in the art of transforming suitable hosts, and under conditions which allow for stable maintenance and expression of the introduced nucleotide sequence (Sambrook et al., 1989, Molecular Cloning: A Laboratory Manual $2^{nd}$ Ed., Cold Spring Harbor Press, New York). Suitable hosts that allow for expression of the proteins of the present invention and related sequences include *B. thuringiensis* and other *Bacillus* species such as *Bacillus subtilis, Bacillus sphaericus, Bacillus laterosporous, Bacillus megaterium*, or *Bacillus anthracis*. Genetically altered or engineered microorganisms containing a gene encoding one or more of the proteins of the present invention, including TIC901, TIC1201, TIC407, TIC417, and TIC431 and the like can also contain nucleotide sequences encoding other toxin proteins present in the same microorganism; these coding sequences could concurrently produce insecticidal proteins different from the proteins of the present invention or related proteins. In particular, it would be preferable to produce two or more different insecticidal proteins in a host cell, wherein each protein is toxic to the same insect species and each protein exhibits a mode of action different from the other(s).

Plant-colonizing or root-colonizing microorganisms may also be employed as host cells for the production of one or more of the proteins of the present invention or related protein. Exemplary microorganism hosts for *B. thuringiensis* toxin genes include the plant-colonizing microbe *Clavibacter xyli* as described by Turner et al. (1993; Endophytes: an alternative genome for crop improvement; International Crop Science Congress, Ames, Iowa, USA, 14-22 Jul. 1992, pp. 555-560) and root-colonizing pseudomonad strains, as described by Obukowicz et al. (U.S. Pat. No. 5,229,112).

The toxin-encoding nucleotide sequences obtainable from the isolates of the present invention can be introduced into a wide variety of microbial or plant hosts. Expression of the toxin gene results, directly or indirectly, in the intracellular production and maintenance of the pesticide. With suitable microbial hosts, e.g., *Pseudomonas*, the microbes can be applied to the situs of the pest, where they will proliferate and be ingested by the pest. The result is a control of the pest exhibited by reduced plant damage, increased plant yield, decreased prevalence of the plant pest in the general local environment of the transgenic organism expressing the toxin protein(s), and the death or stunted growth of the plant pest, generally without any additional impact on the microbial flora surrounding the plant or transgenic organism expressing the toxin protein(s), and without any additional impact on the environment in general. Alternatively, the microbe hosting the toxin gene can be treated under conditions that prolong the activity of the toxin and stabilize the cell. The treated cell, which retains the toxic activity, then can be applied to the environment of the target pest.

Where the toxin gene of the present invention or a related nucleotide coding sequence is introduced by means of a suitable vector into a microbial host, and the host is applied to the environment in a living state, it is advantageous to use certain host microbes. For example, microorganism hosts can be selected which are known to occupy the pest's habitat. Microorganism hosts may also live symbiotically with a specific species of pest. These microorganisms are selected so as to be capable of successfully competing in the particular environment with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the habitat of pests. These microorganisms include bacteria, algae, and fungi. Of particular interest are microorganisms, such as bacteria, e.g., genera *Bacillus, Escherichia, Pseudomonas, Erwinia, Serratia, Klebsiella, Salmonella, Pasteurella, Xanthomonas, Streptomyces, Rhizobium, Rhodopseudomonas, Methylophilius, Agrobacterium, Acetobacter, Lactobacillus, Arthrobacter, Azotobacter, Leuconostoc,* and *Alcaligenes*; fungi, e.g., genera *Metarhizium, Bavaria, Saccharomyces, Cryptococcus, Kluyveromyces, Sporobolomyces, Rhodotorula,* and *Aureobasidium*.

A wide variety of means are available for introducing a toxin gene encoding a toxin into a microorganism host under conditions that allow for stable maintenance and expression of the gene. These methods are well known to those skilled in the art and are described, for example, in U.S. Pat. No. 5,135, 867.

As mentioned above, *B. thuringiensis* or recombinant cells expressing a protein of the present invention or a related toxin protein can be treated to prolong the toxin activity and stabilize the cell. The pesticide microcapsule that is formed comprises one or more of the proteins of the present invention or one or more related toxins within a structure that has been stabilized and which functions to protect the toxin or toxins when the microcapsule is applied to the environment of the target pest. Suitable host cells may include either prokaryotes or eukaryotes, normally being limited to those cells that do not produce substances toxic to higher organisms, such as mammals. However, organisms which produce substances toxic to higher organisms could be used, where the toxic substances are unstable or the level of application sufficiently low as to avoid any possibility of toxicity to a mammalian host. Of particular interest as hosts will be prokaryotes as well as lower eukaryotes such as fungi. The cells of these organisms will usually be intact and be substantially in the proliferative form when treated, rather than in a spore form, although in some instances spores may be employed. Such microcapsules can also contain one or more of the proteins of the present invention or one or more related proteins along with one or more unrelated insecticidal protein compositions including but not limited to delta endotoxins such as Cry1, Cry2, Cry3, Cry9, Cry22, ET70, TIC851, and/or binary toxins such as ET80/76, ET33/34, PS149B1, and ET100/101 and the like, and insecticidal proteins or insecticidal protein complexes from such diverse organisms such as *Xenorhabdus* and/or *Photorhabdus*, or VIP, WAR, and/or MIS protein toxins and related proteins.

Treatment of the microbial cell, e.g., a microbe containing a nucleotide sequence or a nucleotide segment of the present invention or a related coding sequence, can be by chemical or physical means, or by a combination of chemical and/or physical means, so long as the technique does not deleteriously affect the properties of the toxin, nor diminish the cellular capability of protecting the toxin. Examples of chemical reagents are halogenating agents, particularly halogens of atomic no. 17-80. More particularly, iodine can be used under mild conditions and for sufficient time to achieve the desired results. Other suitable techniques include treatment with aldehydes, such as glutaraldehyde; anti-infectives, such as zephiran chloride and cetylpyridinium chloride; alcohols, such as isopropyl and ethanol; various histologic fixatives, such as Lugol iodine, Bouin's fixative, various acids, and Helly's fixative (See: Humason, 1967); or a combination of physical (heat) and chemical agents that preserve and prolong the activity of the toxin produced in the cell when the cell is administered to the host animal. Examples of physical means are short wavelength radiation such as gamma-radiation and X-radiation, freezing, UV irradiation, lyophilization, and the like. Methods for treatment of microbial cells are disclosed in U.S. Pat. Nos. 4,695,455 and 4,695,462.

The cells generally will have enhanced structural stability that will enhance resistance to environmental conditions. Where the pesticide is in a proform or precursor form, the method of cell treatment should be selected so as not to inhibit processing of the proform to the mature form of the pesticide by the target pest pathogen. For example, formaldehyde will crosslink proteins and could inhibit processing of the proform of a polypeptide pesticide. The method of cell treatment retains at least a substantial portion of the bio-availability or bioactivity of the toxin.

Characteristics of particular interest in selecting a host cell for purposes of production include ease of introducing one or more of the coding sequences of the present invention or one or more related coding sequences into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; survival in aqueous environments; lack of mammalian toxicity; attractiveness to pests for ingestion; ease of killing and fixing without damage to the toxin; and the like. Other considerations include ease of formulation and handling, economics, storage stability, and the like.

The cellular host containing a nucleotide sequence encoding a protein of the present invention or a related protein may be grown in any convenient nutrient medium, where the DNA construct provides a selective advantage, providing for a selective medium so that all or substantially all of the cells retain the nucleotide sequence encoding the protein of the present invention or related coding sequence. These cells may then be harvested in accordance with conventional ways. Alternatively, the cells can be treated prior to harvesting.

The coding sequences of the present invention, including those as set forth in SEQ ID NO:3, SEQ ID NO:5, SEQ ID NO:7, SEQ ID NO:9, and SEQ ID NO:32 and the like can be used as the basis for constructing modified nucleotide sequences for incorporation into plant cells. Even more preferable is the synthesis of a non-naturally occurring nucleotide sequence that encodes one or more of the proteins of the present invention or a related insecticidal protein or its equivalent for expression in a plant cell, the synthesis of the non-naturally occurring nucleotide sequence being based on the amino acid sequence of the native protein without reference to the native nucleotide sequence from which the native amino acid sequence was deduced. Expression of such sequences in plant cells would render a plant comprised of such cells more resistant to insect attack by coleopteran species and the like. Genetic engineering of plants with modified sequences encoding one or more of the proteins of the present invention or a related protein or a related insecticidal amino acid sequence may be accomplished by introducing the desired plantized (the word 'plantized' being synonymous with the words 'modified' or 'synthetic') DNA containing the coding sequence into plant tissues or cells, using DNA molecules of a variety of forms and origins that are well known to those skilled in plant genetic engineering. Examples of techniques for introducing DNA into plant tissue are disclosed at least by Perlak et al. (1991).

DNA containing a modified gene encoding a protein of the present invention such as a TIC901, a TIC1201, a TIC407, a TIC417, or a TIC431 and the like, or a related insecticidal protein, operatively linked to a plant functional promoter, may be delivered into the plant cells or tissues directly by a number of means including but not limited to *Agrobacterium* mediated transformation, plant viruses, electroporation, microinjection, vacuum infiltration, liposome fusion means, and ballistic methods and the like. The plant promoter may be a constitutive promoter; or the promoter may be a temporally, spatially, chemically, photosynthetically, thermally, or artificially regulated promoter; a tissue-specific promoter; or even a chimeric or hybrid promoter assembled from parts of other plant functional promoters. For example, the promoter may be a cauliflower mosaic virus (CaMV) 35S promoter or a plant functional derivative thereof.

Native bacterial genes and coding sequences are often poorly expressed in transgenic plant cells. Plant codon usage more closely resembles that of other higher organisms than unicellular organisms, such as bacteria. Several reports have disclosed methods for improving expression of recombinant genes in plants (Murray et al., 1989, Nucleic Acids Research, Vol. 17:477-498; Diehn et al., 1998, Plant Physiology, 117: 1433-1443; Rocher et al., 1998, Plant Phys. 117:1445-1461). These reports disclose various methods for engineering coding sequences to represent sequences which are more efficiently translated based on plant codon frequency tables, improvements in codon third base position bias, using recombinant sequences which avoid suspect polyadenylation or A/T rich domains or intron splicing consensus sequences. While these methods for synthetic gene construction are notable, synthetic genes of the present invention for expression in particular plants are prepared substantially according to the method of Brown et al. (U.S. Pat. No. 5,689,052).

The work described herein takes advantage of methods of potentiating in planta expression of one or more of the proteins of the present invention and related insecticidal proteins, which confer resistance to coleopteran or even lepidopteran plant insect or even nematode pathogens, by incorporation or localization of coding sequences into the nuclear, plastid, or chloroplast genome of susceptible plants. U.S. Pat. No. 5,500,365 and related patents describe methods for synthesizing plant genes to achieve optimum expression levels of the protein for which the synthesized, non-naturally occurring, synthetic, or artificial gene encodes. These methods relate to the modification of native Bt structural gene sequences to produce a coding sequence that is more "plant-like" and therefore more likely to be translated and expressed by the plant, monocot or dicot. However, the method as disclosed in Brown et al. (U.S. Pat. No. 5,689,052) provides for enhanced expression of transgenes, preferably in monocotyledonous plants.

Thus, the amount of a gene or nucleotide sequence or nucleotide segment coding for a polypeptide of interest, e.g. all or an insecticidal part of a TIC901, TIC1201, TIC407, TIC417, TIC431 or related polypeptide, can be increased in plants by transforming those plants using transformation methods mentioned above. In particular, transformation of chloroplast or plastid organelles can result in desired coding sequences being present in up to about 10,000 copies per cell in tissues containing these subcellular organelle structures (McBride et al., WO 95/24492).

DNA encoding the peptides of the present invention and related proteins can also be introduced into plants by utilizing a direct DNA transfer method into pollen as described (Zhou et al., 1983, Mol. Cell Biol., 10:4529-4537; Hess, 1987, Intern Rev. Cytol., 107:367.). Expression of polypeptide coding sequences, i.e., tic901 and the like, can be obtained by injection of the DNA into reproductive organs of a plant as described (Pena et al., 1987, Nature, 325:274). The DNA can also be injected directly into the cells of immature embryos and into rehydrated desicated embryos as described (Neuhaus et al., 1987, Theor. Appl. Genet., 75:30).

After effecting delivery of exogenous nucleotide sequences encoding the insecticidal proteins of the present invention or related proteins to recipient cells, the next step to obtain a transgenic plant generally concerns identifying the transformed cells for further culturing and plant regeneration, i.e., selection of the transformed cells. As mentioned herein, in order to improve the ability to identify transformants, one may desire to employ a selectable or screenable marker gene as, or in addition to, the expressible gene of interest. In this case, one would then generally assay the potentially transformed cell population by exposing the cells to a selective agent or agents, or one would screen the cells for the desired marker gene trait.

An exemplary embodiment of methods for identifying transformed cells involves exposing the transformed cultures to a selective agent, such as a metabolic inhibitor, an antibiotic, herbicide or the like. Cells that have been transformed and have stably integrated a marker gene conferring resistance to the selective agent used, will grow and divide in culture. Sensitive cells will not be amenable to further culturing. One example of a preferred marker gene confers resistance to the herbicide glyphosate. When this gene is used as a selectable marker, the putatively transformed cell culture is treated with glyphosate. Upon exposure to glyphosate, transgenic cells containing a recombinant GOX enzyme or a recombinant glyphosate insensitive EPSPS enzyme will be available for further culturing while sensitive, or non-transformed cells, will not. (U.S. Pat. No. 5,569,834). Another example of a preferred selectable marker system is the neomycin phosphotransferase (nptII) resistance system by which resistance to the antibiotic kanamycin is conferred, as described in U.S. Pat. No. 5,569,834. Again, after transformation with this system, transformed cells will be available for further culturing upon treatment with kanamycin, while non-transformed cells will not. Yet another preferred selectable marker system involves the use of a gene construct conferring resistance to paromomycin. Use of this type of a selectable marker system is described in U.S. Pat. No. 5,424,412. Other selectable markers are well known in the art, including but not limited to antibiotic resistance markers such at nptII, tet, aad, and the like, phnO and other various acetylases (U.S. Pat. No. 6,448,476), various esterases (U.S. Pat. No. 6,107,549), barnase (Hartley, 1988), J. Mol. Biol. 202: 913), bacterial enzymes conferring glyphosate oxidase activity upon the transformed cell (gox) (Barry et al., 1992, Inhibitors of amino acid biosynthesis: Strategies for imparting glyphosate tolerance to crop plants. In: Biosynthesis and Molecular Regulation of Amino Acids in Plants. pp. 139-145. Singh, Flores, and Shannon Eds., American Society of Plant Physiologists, Rockville, Md.) and the like.

Transplastonomic selection (selection of plastid or chloroplast transformation events) is simplified by taking advantage of the sensitivity of chloroplasts or plastids to spectinomycin, an inhibitor of plastid or chloroplast protein synthesis, but not of protein synthesis by the nuclear genome encoded cytoplasmic ribosomes. Spectinomycin prevents the accumulation of chloroplast proteins required for photosynthesis so spectinomycin resistant transformed plant cells may be distinguished on the basis of their difference in color: the resistant, transformed cells are green, whereas the sensitive cells are white, due to inhibition of plastid-protein synthesis. Transformation of chloroplasts or plastids with a suitable bacterial aad gene, or with a gene encoding a spectinomycin resistant plastid or chloroplast functional ribosomal RNA provides a means for selection and maintenance of transplastonomic events (Maliga, 1993, Trends in Biotechnology 11: 101-106).

It is further contemplated that combinations of screenable and selectable markers will be useful for identification of transformed cells. In some cell or tissue types a selection agent, such as glyphosate or kanamycin, may either not provide enough killing activity to clearly recognize transformed cells or may cause substantial nonselective inhibition of transformants and nontransformants alike, thus causing the selection technique to not be effective. It is proposed that selection with a growth inhibiting compound, such as glyphosate or AMPA (amino-methyl phosponic acid) at concentrations below those that cause 100% inhibition, followed by screening of growing tissue for expression of a screenable marker gene such as kanamycin would allow one to recover transformants from cell or tissue types that are not amenable to selection alone. It is proposed that combinations of selection and screening may enable one to identify transformants in a wider variety of cell and tissue types.

The development or regeneration of plants from either single plant protoplasts or various explants is well known in the art (Weissbach and Weissbach, 1988). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing a foreign, exogenous gene that encodes all or an insecticidal part of a TIC901, TIC1201, TIC407, TIC417, TIC431 or a related polypeptide introduced into the plant genome by *Agrobacterium* transformation of leaf explants can be achieved by methods well known in the art (Horsch et al., 1985). In this procedure, transformants are cultured in the presence of a selection agent and in a medium that induces the regeneration of shoots in the plant strain being transformed as described (Fraley et al., 1983). In particular, U.S. Pat. No. 5,349,124 details the creation of genetically transformed lettuce cells and plants resulting therefrom which express hybrid crystal proteins conferring insecticidal activity against Coleopteran larvae to such plants.

This procedure typically produces shoots within two to four months and those shoots are then transferred to an appropriate root-inducing medium containing the selective agent and an antibiotic to prevent bacterial growth. Shoots that rooted in the presence of the selective agent to form plantlets are then transplanted to soil or other media to allow the production of roots. These procedures vary depending upon the particular plant strain employed, such variations being well known in the art.

Preferably, the regenerated plants are self-pollinated to provide homozygous transgenic plants, or pollen obtained from the regenerated plants is crossed to seed-grown plants of agronomically important, preferably inbred lines. Conversely, pollen from plants of those important lines is used to pollinate regenerated plants. A transgenic plant of the present invention containing a nucleotide sequence encoding a desired insecticidal protein of the present invention or a related polypeptide is cultivated using methods well known to one skilled in the art.

A transgenic plant of the present invention contains at least a coding region encoding one or more polypeptides of the present invention or a related polypeptide, such as an insecticidal fragment of a TIC901, a TIC1201, a TIC407, a TIC417, or a TIC431 protein or a chimera of these proteins. A preferred transgenic plant is an independent segregant and can transmit that gene and its activity to its progeny. A more preferred transgenic plant is homozygous for that gene, and transmits that gene to all of its offspring on sexual mating. Seed from a transgenic plant may be grown in the field or greenhouse, and resulting sexually mature transgenic plants are self-pollinated to generate true breeding plants. The progeny from these plants become true breeding lines that are evaluated for increased expression of the *B. thuringiensis* transgene.

Transgenic plants expressing more than one insecticidal agent are preferred, each agent being toxic to a target insect pest species, and each insecticidal agent exhibiting a separate mode of action or exhibiting a different means for introducing pores into the midgut epithelium of the target insect pest either by binding to separate and independent receptors or by forming pores that are measurably different than the pores formed by the other one or more insecticidal agents present in the same transgenic plant. Such plants conceivably may be transformed to express at least two or more of the proteins of the present invention, or will be transformed to express at least one of the proteins of the present invention along with at least one or more unrelated insecticidal protein including but not limited to delta-endotoxin proteins such as one or more of a Cry1, a Cry2, a Cry3, a Cry9, a Cry22, an ET70, a TIC851, and/or any one or more of the binary toxins ET80/76, ET33/34, PS149B1, and ET100/101 and the like and fusions, chimeras, and variants thereof, insecticidal proteins or insecticidal proteins complexes from such diverse organisms such as *Xenorhabdus* and/or *Photorhabdus*, or VIP, WAR, and/or MIS protein toxins and related proteins, and or one or more transgenic double stranded RNA's for which expression in the plant cell results in suppression of one or more genes in one or more target insect pests.

To identify a transgenic plant expressing high levels of a polypeptide of the present invention or a related protein from a preferred nucleotide sequence, it may be necessary to screen the selected transgenic event, ($R_0$ generation) for insecticidal activity and/or expression of the gene. This can be accomplished by various methods well known to those skilled in the art, including but not limited to: 1) obtaining small tissue samples from the transgenic $R_0$ plant and directly assaying the tissue for activity against susceptible insects in parallel with tissue derived from a non-expressing, negative control plant. [For example, $R_0$ transgenic corn plants expressing an insecticidal fragment of a TIC901 or a related protein can be identified by assaying leaf tissue derived from such plants for activity against Colorado Potato Beetle (CPB, *Leptinotarsa decemlineata*) and Southern Corn Rootworm (SCR, *Diabrotica undecimpunctata howardi*)]; 2) analysis of protein extracts by enzyme linked immunoassays (ELISAs) specific for the insecticidal protein fragment or related protein; or 3) reverse transcriptase thermal amplification (also known in the art as RTPCR) to identify events expressing the sequence encoding the insecticidal protein fragment or related protein.

The pesticidal agents of the present invention can be applied alone or in combination with other pesticidal agents to a seed as a component of a seed coating, or the agents of the present invention can be produced within a transgenic seed and combined with other pesticidal agents in the form of a seed coating. Seed coating methods and compositions that are known in the art are useful when they are modified by the addition of one of the embodiments of the combination of pesticides of the present invention. Such coating methods and apparatus for their application are disclosed in, for example, U.S. Pat. Nos. 5,918,413, 5,891,246, 5,554,445, 5,389,399, 5,107,787, 5,080,925, 4,759,945 and 4,465,017. Seed coating compositions are disclosed, for example, in U.S. Pat. Nos. 5,939,356, 5,882,713, 5,876,739, 5,849,320, 5,834,447, 5,791,084, 5,661,103, 5,622,003, 5,580,544, 5,328,942, 5,300,127, 4,735,015, 4,634,587, 4,383,391, 4,372,080, 4,339,456, 4,272,417 and 4,245,432, among others.

As used herein, the term "biological sample", or "sample", is intended to include nucleic acids, polynucleotides, DNA, RNA, tRNA, cDNA, and the like in a composition or fixed to a substrate which enables the sample to be subjected to molecular probe analysis or thermal amplification using oligonucleotide probes and/or primers. A plant or plant product or the fruit or seed from a plant is considered to be a biological sample, and any extract from such plant or plant product, plant part, fruit, or seed, is also considered to be a biological sample. As such, biological samples can be derived from agronomically and commercially important products and/or compositions of matter including but not limited to animal feed, commodities, and corn products and by-products that are intended for use as food for human consumption or for use in compositions that are intended for human consumption including but not limited to corn flour, corn meal, corn syrup, corn oil, corn starch, popcorn, corn cakes, cereals containing corn and corn by-products, and the like are intended to be within the scope of the present invention if these products and compositions of matter contain detectable amounts of the nucleotide sequences or the pesticidal proteins encoded therefrom as set forth herein.

The following examples further illustrate the characteristics of the nucleotide sequences disclosed herein and the insecticidal activity of the proteins encoded by the disclosed nucleotide sequences. In addition, methods and procedures for practicing the invention are disclosed. However, those of skill in the art should, in light of the present disclosure, appreciate that many changes can be made in the specific embodiments which are disclosed and still obtain a like or similar result without departing from the spirit and scope of the invention.

EXAMPLES

Example 1

This example illustrates the identification of an insecticidal protein secreted into the media by *B. thuringiensis* strain EG2158.

EG2158 is a wild-type *B. thuringiensis* strain originally isolated from soybean grain dust (Donovan et al., 1988). During sporulation cells of EG2158 produce rhomboid-shaped crystals composed of a 73 kDa protein identified to be Cry3C. Spore crystal mixtures of EG2158 are toxic to Colorado potato beetle larvae. *Bacillus megaterium* transformed with the cloned cry3C gene exhibit toxicity to CPB larvae similar to strain EG2158 suggesting that the coleopteran-specific toxicity of EG2158 is due to the Cry3C crystal protein (Donovan et al., 1988). Therefore, it was unexpected that spent media used for fermentation of strain EG2158, which does not contain spores or Cry3C crystal protein, would be toxic to CPB because the processed spent media does not contain sufficient spores or Cry3 crystal protein to exhibit measurable insecticidal toxicity.

*B. thuringiensis* strains were grown in 60 mL of PYG culture medium with shaking overnight at 30° C. PYG medium consisted of 11.8 grams peptone, 23.6 grams yeast extract, 4 milliliters glycerol, 19.4 grams anhydrous $K_2HPO_4$, and 2.2 grams anhydrous $KH_2PO_4$ per liter of deionized water. *B. thuringiensis* cultures fermented overnight were centrifuged at 11,000×g for 30 minutes and the cell free supernatants were transferred to clean flasks. Supernatants are also referred to herein as spent medium and/or clarified spent medium or clarified supernatant.

The supernatants were chilled to 4° C. 34 grams of ammonium sulfate plus 1 milliliter of 1 M NaOH were slowly added to 60 milliliters of supernatant while stirring. The ammonium sulfate saturated supernatant mixtures were centrifuged to collect the precipitable proteins into a pellet. The pellets were dissolved in 2 milliliters of 20 mM Tris.HCl pH 7.5. The Tris suspensions were transferred to dialysis tubing (6000 MWCO) and dialyzed at 4° C. against 20 mM Tris-HCl pH 7.5. The dialyzed suspensions are referred to herein as am.sulf-dialysates (ASD).

The am.sulf.-dialysates (ASD) were tested for toxicity to Colorado potato beetle larvae (CPB, also formally known as *Leptinotarsa decemlineata*). 50 μl of each ASD was applied topically to 2 mL of insect diet in a diet cup. A total of sixteen diet cups were treated for each dialysate. One first-instar CPB larva was placed in each diet cup and insect mortality was scored after 3 days. Numerous repetitions of this procedure were completed with a number of different *B. thuringiensis* strains. The dialysate from *B. thuringiensis* strain EG2158 exhibited toxicity to CPB larvae.

Example 2

This example illustrates a means for purifying an insecticidal protein, designated herein as TIC901, from the spent culture media produced by fermentation of *Bacillus thuringiensis* strain EG2158.

Proteins present in the EG2158 ASD were evaluated by sodium dodecylsulfate polyacrylamide gel electrophoresis (SDS-PAGE). 30 μl of the dialysate was mixed with 15 μl of Laemmli protein solubilization buffer (Mol. Biol. 80:575-599; 1973) and heated to 100° C. for 5 minutes. Approximately 25 μl of the mixture was loaded onto a 10% SDS polyacrylamide gel. The proteins were visualized after electrophoresis after staining with Coomassie Brilliant Blue. The results indicated that the EG2158 ASD contained about thirty proteins ranging in size from approximately 20 kDa to about 120 kDa.

2 milliliters of the EG2158 ASD was applied to a diethylaminoethyl (DEAE) column equilibrated with 20 mM Tris-HCl pH 7.5. Proteins were eluted from the column with a 20 milliliter gradient of NaCl (0 to 500 mM) in 20 mM Tris-HCl, pH 7.5. 1 milliliter fractions of the eluate were collected and each fraction was dialyzed against 20 mM Tris-HCl, pH 7.5. Individual fractions were tested after dialysis for toxicity to CPB using a bioassay similar to that described in Example 1. Fractions exhibiting toxicity to CPB larvae were pooled and dialyzed. The pooled fractions were referred to as the EG2158 DEAE-toxic fraction. Proteins in the EG2158 DEAE-toxic fraction were analyzed by SDS-PAGE and Coomassie staining. The results indicated that the EG2158 DEAE-toxic fraction contained five primary proteins as well as several minor proteins of various sizes.

2 milliliters of the EG2158 DEAE-toxic fraction was applied to a quaternary ammonium (QA) column equilibrated with 20 mM Tris-HCl pH 7.5. Protein was eluted from the column with 20 milliliters of a linear NaCl gradient (0 to 500 mM) in 20 mM Tris-HCl, pH 7.5. 1 milliliter fractions were collected and dialyzed separately, again in 20 mM Tris-HCl, pH 7.5. Dialyzed fractions were tested for toxicity to CPB larvae. Fractions exhibiting the highest CPB toxicity were pooled. The pooled fraction was referred to as the EG2158 QA-toxic fraction. Proteins in the EG2158 QA-toxic fraction were analyzed by SDS-PAGE and Coomassie staining. The results indicated that the EG2158 QA-toxic fraction contained one major protein of approximately 38 kDa, referred to as TIC901, and several other minor protein species of various sizes. The results suggested that the purified 38 kDa protein was responsible for CPB toxicity exhibited by the samples.

Example 3

This example illustrates the isolation and identification of a nucleotide sequence from EG2158 that encodes the TIC901 protein.

Proteins in the EG2158 QA-toxic fraction were size-separated by SDS-PAGE without Coomassie staining. Separated proteins were transferred from the SDS-PAGE to a polyvinylidene difluoride (PVDF) membrane by electrotransfer. The PVDF membrane was stained briefly with Coomassie dye and the portion of the membrane containing the purified TIC901 protein was excised with a clean razor blade and subjected to automated Edmund degradation sequencing. The results indicated that the TIC901 protein contained an amino terminal amino acid sequence corresponding to $^{NH_3}$-V I G P Y A E S Y I D R V Q D-$^{COO-}$ as set forth in SEQ ID NO:1.

It is widely recognized that most proteins produced in vivo in bacterial systems exhibit a methionine (M) residue at their N-terminus. The fact that the N-terminus of the TIC901 protein did not contain an amino terminal methionine residue, along with the fact that the protein was found to be localized to the spent medium, suggested that the TIC901 protein might be formed by proteolytic digestion of a secretory signal peptide from the N-terminal region of a larger precursor protein.

Based on the partial amino acid sequence of the gel purified TIC901 protein as determined by Edmund degradation, and based on the codon usage preference exhibited by native *Bacillus thuringiensis* genes encoding δ-endotoxins, a degenerate oligonucleotide probe was designed for use as a probe to detect nucleotide sequences from *Bacillus thuringiensis* strain EG2158 that might encode the gel purified TIC901 protein. The probe was identified as WD444 and comprised the sequences as set forth in SEQ ID NO:2 (5'-GTA ATT GGA CCA TAT GCA GAA TCA TAT ATT GAT XGA GTA CAA GA-3', where X is either A or C).

DNA was purified from *B. thuringiensis* strain EG2158 cells by standard procedures (e.g., Sambrook et al., 1989). A sample of the DNA extract was digested with HindIII restriction endonuclease, subjected to 0.8% agarose gel electrophoresis in TAE buffer, blotted to a nylon filter, and analyzed by Southern blot by probing with an alkaline phosphatase conjugated WD444 probe mixture for approximately 16 hours at 40° C. in hybridization buffer-under low to moderate stringency, and washed at 40° C. in wash buffer, then exposed to chemi-luminescence reagents, and exposed to film (hybridization and wash buffers were supplied along with AMERSHAM/PHARMACIA BIOTECH Kit, Catalog number RPN3690). The results indicated that the probe appeared to specifically hybridize with a single approximately 8 kilobase pair HindIII fragment.

An *E. coli* library containing EG2158 HindIII restriction fragments of approximately 8 kilobase pairs was constructed in plasmid pUC18. Recombinant colonies were blotted to nylon filters and denatured with NaOH by standard procedures (e.g., Sambrook et al., 1989). The filters were incubated in hybridization solution with labeled WD444 probe mixture. The membranes were washed after incubation with the probe under conditions similar to those described above, exposed to chemiluminescence reagents, and exposed to film. Several colonies were identified that appeared to specifically hybridize to the WD444 probe mixture. Plasmid DNA was extracted from several of these colonies and analyzed by Southern blot using the WD444 oligonucleotide mixture as a probe. The results indicated that the plasmids consisted of the pUC18 vector plus a HindIII insert fragment of approximately 8 kb. One typical plasmid was selected for further characterization and was designated as pEG1379 (and later as pMON74007). The colony purified *E. coli* strain containing pMON1379 was designated EG12447 and was deposited with the NRRL on Feb. 6, 2002 and provided with the deposit accession number NRRL B 30549.

Example 4

This example illustrates the expression of an insecticidal protein from an approximately 8 kilobase pair HindIII fragment in plasmid pEG1381 in an acrystalliferous strain of *Bacillus thuringiensis*.

Native *Bacillus thuringiensis* genes are often poorly expressed in non-*Bacillus* host cells such as *E. coli*. pEG518 was constructed as an *Bacillus-E. coli* shuttle vector and is a chimera of a *Bacillus* replicon pMM101 (Norton et al., Plasmid 13:211-214; 1985) and pUC18 (Yanisch-Perron et al, Gene 33:103-119; 1985) and therefore is capable of replication either in *E. coli* and closely related gram negative bacteria or in *Bacillus* and closely related gram positive bacteria. pEG518 confers β-lactam antibiotic resistance to *E. coli* and related bacteria and tetracycline resistance to *Bacillus* and related bacteria transformed to contain derivatives of this particular plasmid. The 8 kilobase pair HindIII fragment present in plasmid pMON1379 was excised and inserted into the HindIII site in plasmid pEG518. The resulting plasmid, pEG1381, was transformed by electroporation into the acrystalliferous and non-insecticidal *Bacillus thuringiensis* strain EG10650 (NRRL Accession Number NRRL B-30217).

(*Bacillus thuringiensis* strain EG10650. *B. thuringiensis* EG10650 is a derivative of strain EG10368 (U.S. Pat. No. 5,759,538; Jun. 2, 1998) that is deficient in neutral protease and alkaline protease activities and contains only one known extra-chromosomal plasmid element of 7.5 kb. A deletion in the alkaline protease gene was introduced in strain EG10368, resulting in strain EG EG10654 (NRRL Accession Number NRRL B-21344). A deletion in the neutral protease gene was introduced in strain EG10368, resulting in strain EG10624 (NRRL Accession Number NRRL B-21347). These deletions were then combined into one strain to produce strain EG10650, lacking any mega-Dalton plasmids and therefore lacking the potential for expressing any known insecticidal proteins as well as being deficient in the production of both the alkaline and neutral proteases.)

A single colony representing a single transformant and designated as EG12450 was selected on media containing tetracycline for further analysis.

Plasmid pEG1381 was isolated from a culture of strain EG12450 grown overnight in the presence of tetracycline. pEG1381 DNA was digested with HindIII and compared by agarose gel electrophoresis and ethidium bromide staining to the HindIII fragment present in pEG1379. Both plasmids contained an apparently identical about 8 kb HindIII fragment.

Strains EG12450, EG2158, and EG10650 were grown overnight in PYG medium. An ammonium sulfate dialysate (ASD) was prepared from each of the culture supernatants as described in Example 1. ASD samples were applied to a DEAE column, proteins were eluted from the column, and fractions were collected as described in Example 2. Proteins in the DEAE fractions were analyzed by SDS-PAGE and stained with Coomassie Brilliant Blue. The results demonstrated that DEAE fractions of the control acrystalliferous strain EG10650 did not contain significant amounts of any protein corresponding in size to the TIC901 protein, although some minor proteins of approximately the size of the TIC901 protein were present. In contrast, the DEAE fractions obtained from spent culture supernatants in which strain EG2158 was grown contained a prevalent amount of a protein corresponding to the size of the TIC901 protein. DEAE fractions obtained from spent culture supernatants in which the recombinant strain EG12450 was grown contained significant amounts of a protein corresponding to the size of the TIC901 protein produced by strain EG2158. This result indicated that the 8 kb HindIII fragment derived from strain EG2158 present in the recombinant plasmid pEG1381 contained a native *Bacillus thuringiensis* gene a protein exhibiting a mass about equal to that of the the TIC901 protein isolated from strain EG2158 spent fermentation media.

Example 5

This example illustrates the identification of the DNA sequence of the native nucleotide sequence encoding the TIC901 protein, and the deduced TIC901 amino acid sequence.

The approximately 8 kilobase pair HindIII fragment present in plasmid pMON1378 was subjected to dideoxynucleotide sequence analysis. Part of the nucleotide sequence derived from this 8 kb fragment is set forth in SEQ ID NO:5. An open reading frame consisting of 1101 nucleotides was identified within the approximately 8 kilobase pair HindIII fragment, beginning with an ATG methionine codon at nucleotide position 153-155 and terminating at a leucine codon TTG at nucleotide position 1251-1253, immediately upstream of a TAG termination codon as set forth in SEQ ID NO:5. The open reading frame identified within this nucleotide sequence is comprised of 429 adenosine residues (about 39% A), 334 thymidine residues (about 30% T), 196 guanidine residues (about 18% G), and 145 cytosine residues (about 13% C), and exhibits approximately 69% AT and about 31% GC. Three methionine codons are represented within the first eighty four (84) nucleotides of the ORF. Other than the ATG codon at nucleotide positions 153-155 as set forth in SEQ ID NO:3, a second ATG codon in-frame with that at position 153-155 is positioned at nucleotides 182-184 and still a third ATG codon in-frame with these previously mentioned two ATG codons is positioned at nucleotides 201-203. No consensus ribosome binding sequence was observed upstream of either the second or third ATG codons, however a consensus ribosome binding sequence was identified upstream of the first ATG codon, centered at about 10 nucleotides upstream of the first ATG. The consensus ribosome binding sequence consists of nucleotides from about 141 to about 147 as set forth in SEQ ID NO:3.

The amino acid sequence deduced from this open reading frame consists of 367 amino acids as set forth in SEQ ID NO:4. The open reading frame is predicted to encode a precursor protein that has a calculated molecular weight of about 41,492 Daltons. 40 amino acids are strongly basic (lysine and arginine), 43 amino acids are strongly acidic (aspartate and glutamate), 113 amino acids are characteristically hydrophobic in nature (alanine, isoleucine, leucine, phenylalanine, tryptophan, and valine), and 122 amino acids are characteristically polar in nature (asparagine, cysteine, glutamine, serine, threonine, and tyrosine). The precursor protein exhibits a calculated isoelectric point of about 6.368 and exhibits a calculated net charge of about −2.102 at pH 7.0. The first thirty (30) amino acid residues encoded by the open reading frame are predicted to comprise the amino terminal signal peptide that is processed, likely by a type II signal peptidase, to release the insecticidal protein into the extracellular space. These first thirty (30) amino acid residues are predicted to comprise an amino terminal signal peptide based on the algorithm of Nielsen et al. (1997, Protein Engineering 10:1-6). The predicted signal peptide in addition to the amino acid residues from position thirty-one (31) through forty-three (43) as set forth in SEQ ID NO:4 are not found to be linked to or associated with the mature protein localized into the spent media and are believed to be proteolytically removed during membrane translocation and release of the mature insecticidal protein into the extracellular space.

Nucleotides 130 through 174 as set forth in SEQ ID NO:3 correspond most closely to the probe sequence as set forth in SEQ ID NO:2. The SEQ ID NO:2 nucleotides, when read in frame with the corresponding coding sequence of the TIC901 amino acid sequence, correspond to the codons encoding the amino terminal amino acids of the insecticidal protein purified from the spent media of cultures of *Bacillus thuringiensis* strain EG2158. The amino acids encoded by the TIC901 reading frame throughout this nucleotide sequence region were expected to correspond to the amino acid sequence of the amino acids deduced by Edmund Degradation of the insecticidal protein purified from the spent media of cultures of strain EG2158 and as set forth in SEQ ID NO:1. The amino acid sequence as set forth in SEQ ID NO:1 is identical to the amino acid sequence deduced by this region of the open reading frame for TIC901, except that amino acid position 12 as set forth in SEQ ID NO:1 corresponds to an arginine residue, whereas the corresponding amino acid residue deduced by the sequence of the open reading frame in SEQ ID NO:3 corresponds to an isoleucine residue at amino acid position 55 as set forth in SEQ ID NO:4. This result suggested either that an error was encountered as a result of Edmund sequence analysis of the protein purified from EG2158 spent culture media and believed to be TIC901 protein, or that more than one TIC901-like protein was present in the concentrated and purified sample submitted for Edmund sequence analysis. It is well known that mistakes in Edmund sequencing are not uncommon. However, this result alone suggested that more than one gene encoding an extracellular secreted insecticidal protein may be present in *Bacillus thuringiensis* strain EG2158. A full analysis of this hypothesis is set forth herein from about Example 9.

Most bacterial proteins released into the extracellular spaces tend to be synthesized as larger precursors that are processed by a secretion apparatus that cleaves a portion of the precursor protein away from the mature protein that is released into the extracellular milieu. It is possible that the insecticidal protein found in the spent media from cultures of strain EG2158 is synthesized in strain EG2158 as a precursor protein that is targeted for secretion by all or part of the forty three (43) amino acids deduced as a part of the open reading frame as set forth in SEQ ID NO:3. Secreted proteins produced by gram positive and gram negative bacteria that are targeted to a type II secretion apparatus typically exhibit a secretory or signal peptide that is between from about eighteen (18) to about twenty eight (28) to thirty (30) or more amino acids in length. As indicated above, there are two methionine codons corresponding to amino acid residues eighteen (18) and twenty seven (27) respectively, as deduced from the open reading frame as set forth in SEQ ID NO:3, upstream of the valine residue (codon at nucleotides 282-284 as set forth in SEQ ID NO:3) deduced by Edmund Degradation to be the amino terminal amino acid of the TIC901 protein. The valine residue as set forth in SEQ ID NO:4 corresponding to the Edmund degradation predicted amino terminal residue of the secreted protein found in the spent media from cultures of EG2158 is positioned at residue number forty four (44). It is conceivable that the two proximal methionine residues within the amino acid sequence amino terminal to the valine residue at position 44 comprise alternative translation initiation sites for synthesis of the proposed precursor TIC901 protein produced in EG2158. However, very poor consensus Shine-Delgarno sequences are available upstream of these two alternative translation initiation codons. In addition, because the protein is found in the spent media, an analysis of the predicted amino acid sequence encoded by the nucleotides following the MET codon at position 153-155 using signal peptide prediction algorithms well known in the art indicates that the first thirty amino acids fit well within the parameters established for amino acid sequences that function as signal peptides. Therefore, it is believed that the first ATG at nucleotide positions 153-155 as set forth in SEQ ID NO:3 is the transcription initiation codon actually utilized by *Bacillus thuringiensis* strain EG2158 for expression of the precursor TIC901 protein that is subsequently processed to the mature form of the protein secreted from the cell.

The predicted signal peptide, as indicated above, is comprised of amino acid residues one (1) through thirty (30) as set forth in SEQ ID NO:4 and exhibits the hallmarks of a classic type II signal peptide, including a basic charge at the amino terminus, a neutral charged predicted alpha-helical core region from about amino acid residue six (6) through about amino acid residue twenty-two (22) and a consensus signal peptidase II recognition sequence Ala-Xaa-Ala at residues twenty-eight (28) through thirty (30) which would be recognized as a proteolytic cleavage substrate for cleavage of the peptide bond between amino acid residues thirty (30) and thirty-one (31). The carboxyl terminus of the signal peptide has been identified as being crucial as a recognition sequence for the signal peptidase responsible for proteolytic cleavage of the signal peptide from the precursor protein, releasing the mature protein into the extracytoplasmic spaces, i.e., periplasm or extracellular space for gram negative bacteria, or into the extracellular space for gram positive bacteria. The stereotypical consensus signal peptidase II recognition sequence is Ala-Xaa-Ala. The rule for the Xaa residue is that it typically cannot be a large or charged amino acid residue. In contrast, the three residues adjacent to the amino terminal amino acid residue (+1) in the mature TIC901 protein do not conform to the consensus type II signal peptidase recognition sequence. Instead, the TIC901 signal peptide amino acid sequence that may be recognized by an alternative or presently unknown and/or uncharacterized signal peptidase is Ser-Gln-Gln (S-Q-Q), which is remarkably uncharacteristic of any signal peptidase recognition sequence previously observed. Alternatively, there could be some as yet unidentified peptidase that recognizes the overall structure of amino acids thirty-one (31) through forty-three (43) as set forth in SEQ ID NO:4 and removes these amino acids to release the active insecticidal protein into the media or other surrounding extracellular spaces. These last thirteen amino acids from thirty-one (31) through forty-three (43) as set forth in SEQ ID NO:4 may serve to buffer toxicity of the protein until it is released from the cell.

Example 6

This example illustrates a comparison of the insecticidal biological activity of the protein purified from the native *Bacillus thuringiensis* strain EG2158 to the insecticidal protein isolated from the recombinant *Bacillus thuringiensis strain EG*12450.

Spent media samples from cultures of strains EG12450, EG2158, and EG10650 were obtained and soluble proteins present in each of the samples were concentrated and subjected to DEAE fractionation according to the method as set forth in Example 3 herein. Fractions containing the protein corresponding to TIC901 for each strain were pooled. Pooled fractions were compared side by side in bioassay against Colorado potato beetle. The DEAE fractions from EG12450 and EG2158 spent media contained 87 μg/μl and 22 μg/μl TIC901 protein respectively as measured by gel densitometry using known amounts of BSA as a standard. Toxicity to CPB larvae was measured by applying various amounts of the fractions to the surface of insect diet in cups, as described in Example 1. The results are presented in Table 2.

TABLE 2

Percent mortality of CPB larvae.

| | Amount of DEAE Fraction Applied | | | | |
|---|---|---|---|---|---|
| Strain | 50 μl | 25 μl | 12.5 μl | 6.3 μl | 3.1 μl |
| EG2158 | 97% | 78% | 47% | 25% | 19% |
| EG10650 | 3 | 0 | 6 | 3 | 9 |
| EG12450 | 91 | 94 | 72 | 38 | 16 |

The results as shown in Table 2 demonstrate that DEAE fractions containing the TIC901 protein from *B. thuringiensis* strains EG2158 and EG12450 are toxic to CPB larvae. Similar DEAE fractions from strain EG10650 were used as a negative control and were not toxic to CPB larvae. Mean standard errors were not calculated.

Example 7

This example illustrates the isolation of a 1.96 kb NsiI-HincII restriction fragment containing the entire TIC901 coding region from pEG1379, and an analysis of the corn rootworm inhibitory biological activity of the TIC901 protein isolated from spent cultures of a recombinant strain SIC8098 expressing the TIC901 protein from a plasmid containing the NsiI-HincII fragment.

A 1.96 kb NsiI-HincII restriction fragment containing the entire TIC901 coding region from pEG1379 was subcloned into compatible restriction sites (PstI and SmaI) in the *B. thuringiensis-E. coli* shuttle vector pEG597 (Baum et al., 1990). The only open reading frame within this restriction fragment that is capable of encoding a protein the size of TIC901 is the coding sequence as set forth in SEQ ID NO:3. The resulting recombinant plasmid, designated pIC17048, was introduced into the acrystalliferous *B. thuringiensis* host strain EG10650 by electroporation. The recombinant *B. thuringiensis* strain containing pIC17048 was designated as strain SIC8098.

*B. thuringiensis* strains EG10650 and SIC8098 were grown in 300 ml Terrific broth (in 1 L flasks) for 40 hours at 30° C. with vigorous shaking. Spent cultures were centrifuged at 8,000 rpm and 4° C. for 30 minutes in a Sorvall GS3 rotor. Aliquots of the culture supernatants were analyzed by SDS-polyacrylamide gel electrophoresis. Strain SIC8098 accumulates high levels of the TIC901 protein in the culture supernatant. Evaluation of growth conditions for EG2158 and for recombinant *B. thuringiensis* strains encoding TIC901 indicated that a substantially greater amount of TIC901 protein accumulated in the spent media when the strains were fermented at 25° C. for forty eight (48) hours instead of under standard conditions of 30° C. for eighteen (18) hours. This suggests that the TIC901 protein may not be optimally produced until late log or early stationary phases of growth have been attained.

EG10650 and SIC8098 culture supernatants were brought to 85% saturation with ammonium sulfate at 4° C. Precipitated proteins were collected by centrifugation. The protein precipitates were solubilized in 10 mM Tris-HCl, 0.1 mM EDTA, 0.005% Triton X-100 (pH 6.8) and dialyzed against a 200-fold excess volume of the same buffer. Insoluble material was pelleted by centrifugation and the clarified dialysate containing the substantially purified TIC901 protein was used directly for insect bioassays. The amount of purified TIC901 protein in the dialysate was determined by SDS-polyacrylamide polyacrylamide gel electrophoresis and densitometry, using bovine serum albumin as a protein standard. Bioassays were conducted in 96-well plates, each well containing an artificial rootworm diet. Samples containing toxin or control samples were deposited onto the diet providing a toxin impregnated surface overlay. An average of one rootworm egg was deposited per well. An average of twenty-four (24) wells were utilized per treatment. Plates were sealed and incubated for one week before larvae were characterized for mortality and mass.

Bioassays were performed against both southern and western corn rootworm larvae, using the rootworm toxin Cry3Bb (amino acid sequence variant 11231, English et. al., U.S. Pat. No. 6,063,597) as a positive control. Assay results are shown in Tables 3 and 4.

TABLE 3

TIC901 Bioassay vs Western corn rootworm

| Source Strain | Toxin mg/ml | Mean larval mass | 95% CI[1] | Significance[2] |
|---|---|---|---|---|
| EG10650 | 0 | 0.44 | 0.35–0.53 | |
| Cry3Bb | 0.25 | 0.18 | 0.13–0.22 | * |

TABLE 3-continued

TIC901 Bioassay vs Western corn rootworm

| Source Strain | Toxin mg/ml | Mean larval mass | 95% CI[1] | Significance[2] |
|---|---|---|---|---|
| Cry3Bb | 0.50 | 0.15 | 0.10–0.20 | * |
| Cry3Bb | 1.0 | 0.13 | 0.10–0.16 | * |
| TIC901 | 0.25 | 0.36 | 0.25–0.48 | |
| TIC901 | 0.50 | 0.48 | 0.36–0.61 | |
| TIC901 | 1.0 | 0.29 | 0.26–0.31 | * |
| TIC901 | 2.0 | 0.27 | 0.23–0.32 | * |

[1]95% confidence interval
[2]An asterisk (*) indicates that the results were significantly different from the EG10650 negative control, Dunnett's test, alpha = 0.05

TABLE 4

TIC901 Bioassay vs Southern corn rootworm

| Source Strain | Toxin mg/ml | Mean larval mass | 95% CI[1] | Significance[2] |
|---|---|---|---|---|
| EG10650 | 0 | 0.64 | 0.55–0.72 | |
| Cry3Bb | 0.25 | 0.45 | 0.40–0.51 | * |
| Cry3Bb | 0.50 | 0.42 | 0.39–0.44 | * |
| Cry3Bb | 1.0 | 0.31 | 0.19–0.42 | * |
| TIC901 | 0.25 | 0.38 | 0.31–0.45 | * |
| TIC901 | 0.50 | 0.33 | 0.20–0.45 | * |
| TIC901 | 1.0 | 0.26 | 0.14–0.38 | * |

[1]95% confidence interval
[2]An asterisk (*) indicates that the results were significantly different from the EG10650 negative control, Dunnett's test, alpha = 0.05

The results demonstrate that TIC901 is active against both rootworm species, but exhibits greater activity against the southern corn rootworm species.

Example 8

This example illustrates the construction of a nucleotide sequence encoding a TIC901 protein for enhanced expression in plants.

The amino acid sequence of the TIC901 protein as set forth in SEQ ID NO:4 was used to construct a nucleotide sequence essentially according to Fischhoff and Perlak, U.S. Pat. No. 5,500,365, and essentially according to Brown et al., U.S. Pat. No. 5,689,052. Briefly, a codon frequency table was derived from more than 53,000 sequence segments of corn, rice, and wheat genomic DNA believed to encode protein sequence in those plants. More than ten million nine hundred thousand codons (10,900,000) were derived from these sequence segments. Codons were then selected for use in constructing the non-naturally occurring or synthetic sequence encoding TIC901 for use in plants. The resulting coding sequence is composed of a GC-composition which resembles the sequences present in plants, and in particular, because monocot plants were used to derive the codon usage table, the coding sequence resembles a monocot gene in architecture more so than a dicot gene and is therefore preferable for use in expressing TIC901 protein or protein variants in monocot plant species. One such sequence for a non-naturally occurring coding sequence preferable for use in monocot species is set forth in SEQ ID NO:13, and the amino acid sequence of the encoded protein is set forth in SEQ ID NO:14. The skilled artisan would recognize that SEQ ID NO:13 is but one of a myriad number of coding sequences that would function to express the insecticidal protein in a monocot plant species. Furthermore, the skilled artisan would also recognize that a synthetic coding sequence such as SEQ ID NO:13 encoding all or an insecticidal portion of the TIC901 protein or an insecticidal amino acid sequence variant thereof consisting of other than the sequence as set forth in SEQ ID NO:4, but which hybridized to SEQ ID NO:13 under stringent hybridization conditions would also be within the scope of the present invention.

Example 9

This example illustrates the identification and characterization of homologues of tic901 and peptides encoded by these nucleotide sequence homologues that are substantially similar to and thus related to the TIC901 protein.

As set forth in Table 1, a number of strains that produced extracellular protein profiles exhibiting coleopteran insecticidal biological activity were identified. The TIC901 protein coding sequence was identified as exemplified in the Examples herein-above from a strain EG2158 plasmid library by probing with SEQ ID NO:2, corresponding to sequences encoding SEQ ID NO:1 and biased toward the codon usage preference exhibited by native *Bacillus thuringiensis* genes encoding & endotoxins. The tic901 coding sequence was then used as a probe to identify homologues of tic901 in genomic plasmid library clones prepared from genomes of other *Bacillus thuringiensis* strains exhibiting secreted insecticidal protein activity an RFLP profile different from the RFLP profile exhibited by strain EG2158.

As set forth in Table 1, *Bacillus thuringiensis* strain 86833 contained a tic901 homologous sequence different from that of strain EG2158. The secreted protein profile from strain 86833 contains a major band at 38 kDa which is similar to that generated by strain EG2158. These facts together suggested that strain 86833 contained a tic901 homolog. The N-terminal sequence of the strain 86833 protein was determined by Edmund degradation, and a fifteen (15) amino acid sequence was identified (amino acids seventy six (76) through ninety one (91) as set forth in SEQ ID NO:6, which also correspond to residues 2-16 of the predicted mature TIC1201 protein). The amino acid sequence did not correspond to any previously known amino acid sequence, but exhibited an 87% identity with the corresponding amino terminal amino acid sequence of the predicted mature TIC901 protein described herein above. A plasmid clone, pJP263, derived from a Lambda ZAP Express DNA library prepared using SauIIIA partially digested, size selected, strain 86833 total DNA containing an insert of about 5 kilobase pairs was identified by probing essentially as described in Example 2 with tic901 DNA labeled with digoxygenin under thermal amplification conditions. Plasmid pJP263 was subjected to thermal amplification conditions to excise the entire strain 86833 insert which was subsequently inserted into the *E. coli/Bacillus* shuttle vector pEG597. The resulting plasmid pJP274-1 was used to transform the acrystalliferous strain EG10650, and an isolate containing this plasmid was selected and designated as the recombinant *B. thuringiensis* strain SIC4018. Strain SIC4018 was fermented as described in Example 1 and the proteins present in the spent culture media were concentrated and tested for insecticidal activity in bioassay, and analyzed by SDS-PAGE. The spent culture media tested positive for coleopteran insecticidal bioactivity, and a protein of about 38 kDa was identified by SDS PAGE analysis as being present in overabundance in the spent culture media. The insert in pJP274-1 was sequenced by the Sanger dideoxy method and a single open reading frame as set forth in SEQ ID NO:5 from nucleotide four hundred thirty seven (437) through sixteen-hundred-twenty-one (1621) was identified. The amino acid sequence of the precursor insecticidal protein deduced from the open reading frame set forth in SEQ ID NO:5 was designated as TIC1201 (SEQ ID NO:6). The nucleotide sequence of a clone corresponding to the "B" type RFLP profile from another strain, EG3618, was also characterized, and determined to contain an ORF identical in sequence to that as set forth in SEQ ID NO:5.

Strain EG6618 exhibited a "C" type RFLP profile as exemplified in Table 1. A plasmid clone, pJP264, derived from a Lambda ZAP Express DNA library prepared using SauIIIA partially digested, size selected, total DNA from strain EG6618 containing an about 5 kilobase pair fragment was identified by probing essentially as described in Example 2 with tic901 DNA labeled with digoxygenin under thermal amplification conditions. DNA sequence analysis of the inserted DNA in pJP264 indicated that there was an incomplete, or partial, open reading frame within this clone, that possibly encoded the C-terminal portion of a new and previously uncharacterized protein. Alignment of this partial ORF with the ORF encoding TIC901 as set forth in SEQ ID NO:3 revealed that the nucleotide sequence of the inserted DNA in pJP264 (nucleotides 481 through 1302 as set forth in SEQ ID NO:7) encoded a peptide, the deduced amino acid sequence of which was substantially similar to the amino acid sequence corresponding to TIC901 amino acid residues 96 through 367. The new amino acid sequence encoded by the nucleotide sequence in pJP264 exhibited an approximately 78 percent identity with the analogous TIC901 peptide sequence. The nucleotide sequences encoding these peptides exhibited an approximately 81 percent identity. The partial coding sequence within pJP264 corresponds to nucleotide position 481 through 1302 as set forth in SEQ ID NO:7 and is analogous to the TIC901 coding sequence as set forth in SEQ ID NO:3 from nucleotide position 438 through nucleotide 1253. The substantial identity between the carboxyl terminus of each of these two proteins suggested that the peptide encoded by the sequence in pJP264 represented a new member of the genus of insecticidal proteins related to the TIC901 protein. Therefore, this protein was designated as TIC407, and the nucleotide sequence encoding the TIC407 protein was designated as tic407.

It was believed that a full length ORF existed for TIC407 within the genome of EG6618. In order to identify the nucleotide sequence of the balance of the 5' portion of the TIC407 coding sequence, a sample of *Bacillus thuringiensis* strain EG6618 total DNA was digested with the restriction enzyme NdeI, the products of which were then diluted and circularized by ligation to generate a population of templates for use in an inverse thermal amplification reaction. The enzyme NdeI was selected because (1) it did not cut the insert sequence in pJP264, (2) it cut often within the *Bacillus thuringiensis* genome because of the prevalence of A and T in the restriction enzyme recognition sequence, and (3) Southern blot analysis of EG6618 DNA indicated that NdeI cut, within reason, near to the endpoints of the DNA inserted into plasmid pJP264 but sufficiently far enough away from the endpoints to incorporate a full length ORF encoding TIC407.

Two divergent inverse thermal amplification primers were prepared based on the partial tic407 nucleotide sequence present in pJP264. Primer prJWP151 (SEQ ID NO:15 CCTTTGGCAGAAACTTTAACTCC) corresponds to the reverse complement of nucleotides 766-788 as set forth in SEQ ID NO:7. Primer prJWP152 (SEQ ID NO:16 GTGTATTCTGGTACGCATGAC) corresponds to nucleotides 955-975 as set forth in SEQ ID NO:7. These primers were included along with NdeI circularlized template molecules described above and the necessary reagents, buffers and Pfu polymerase in a thermal amplification reaction consisting of a five minute denaturation step at 95° C. for five minutes, followed by thirty cycles consisting of a one minute annealing step at 37° C., a two minute extension step at 55° C., and a one minute denaturation step at 95° C., terminating with a five minute extension step at 55° C. and a 4° C. soak until the samples could be further processed. A single thermal amplification product was identified by gel electrophoresis, which was excised and cloned into a T-vector to construct plasmid pJP300-2. The nucleotide sequence of the inserted DNA sequence in pJP300-2 was obtained and provided sufficient nucleotide sequence upstream and downstream of the previous sequence present in pJP264 to identify the complete open reading frame encoding the TIC407 insecticidal protein as well as upstream and downstream flanking sequences. The nucleotide sequence information obtained from pJP300-2 was assembled by computer using sequence analysis software because the sequence present in pJP300-2 was constructed using inverse thermal amplification of a restriction fragment that was circularized from the genome of strain EG6618. Therefore, to confirm that the sequence that had been assembled was accurate and in fact encoded the TIC407 amino acid sequence, first from the partial open reading frame identified in pJP264, and then from the partial sequences identified in pJP300-2, two new thermal amplification primers flanking the open reading frame encoding TIC407 were designed (prJWP186 and prJWP183) for use in the amplification of a completeTIC407 coding sequence from EG6618 genomic DNA.

Construction of primer prJWP186 (SEQ ID NO:17 gccggatccCTAGCTGAATATGCAGTAGATAATG), was based in part on the sequence identified as being upstream of the TIC407 open reading frame in pJP300-2. The first nine (9) nucleotides of this primer correspond to nucleotide sequence that is not present in the sequence identified as being present in either pJP264 or in pJP300-2, and also contains a sequence that incorporates a BamHI restriction site into the sequence upstream of the amplicon produced using these primers. The terminal twenty-five (25) nucleotides in primer prJWP186 correspond to the sequence as set forth at nucleotides twenty-eight (28) to fifty-two (52) in SEQ ID NO:7 which lie upstream of the proposed ATG initiation sequence in the TIC407 ORF, and enable primer extension in toward the TIC407 ORF.

Construction of primer prJWP183 (SEQ ID NO:18 GTGGCACGTTTATAGGCCATTGTTC) was based entirely on the sequence deduced as being within sequence downstream of the TIC407 ORF within pJP300-2, and is the reverse complement of the sequence from nucleotide position seventeen-hundred-thirty-five (1,735) to seventeen-hundred-fifty-nine (1,759) as set forth in SEQ ID NO:7. While there are no restriction site sequences incorporated into this primer, a naturally occurring HindIII recognition sequence is present downstream of the TIC407 ORF as set forth in SEQ ID NO:7 from nucleotide fifteen-hundred to fifteen-hundred-five (1,500-1,505).

Primers prJWP186 and prJWP183 were included in a thermal amplification reaction along with a sample of EG6618 total DNA and reagents necessary to carry out the reaction. Amplification conditions were similar to those described above for amplification of the NdeI circularized sample. An amplicon comprising 1,732 nucleotides corresponding to the TIC407 ORF, including flanking nucleotide sequence up and down stream of the ORF, was isolated. This amplicon was cloned into a T-vector to construct pJP306-4, and the complete nucleotide sequence of the amplicon was obtained. As expected, the nucleotide sequence of the amplicon in pJP306-4 corresponded to nucleotides twenty-eight (28) through seventeen-hundred-fifty-nine (1,759) as set forth in SEQ ID NO:7, and contained an open reading frame as set forth in SEQ ID NO:7 from nucleotide position one hundred ninety six (196) through twelve-hundred-ninety-nine (1,299) encoding a protein consisting of 368 amino acids. Alignment of the nucleotide sequence encoding TIC407 to the sequence encoding TIC901 demonstrated that the two ORF's are about eighty percent (80%) identical, however, the amino acid sequences deduced from the ORF's exhibit only about 74% identity.

The amino acid sequences of TIC901, TIC1201, and TIC407 were aligned to form a consensus amino acid sequence. Even though the primary amino acid sequences were significantly different, regions of substantial identity were readily identifiable. Two regions, corresponding to amino acid sequence ASN-ASN-ASN-HIS-GLN-THR-ASN-ARG from amino acid sequence position 96-103 as set forth in SEQ ID NO:4 and the amino acid sequence GLN-LYS-PHE-ILE-TYR-PRO-ASN from amino acid sequence position 276-282 as set forth in SEQ ID NO:4 were 100% conserved in primary sequence and position within each of the three insecticidal protein sequences. The nucleotide sequence encoding these protein sequences in each of the corresponding open reading frames, i.e., as set forth in each of the sequences in SEQ ID NO:3, SEQ ID NO:5, and SEQ ID NO:7, (TIC901, TIC1201, and TIC407, respectively) was also substantially conserved, providing a means for identifying other homologous sequences encoding such secreted insecticidal proteins present in other *Bacillus* or *Bacillus thuringiensis* strains.

Two thermal amplification primer sequences were prepared for use in a thermal amplification reaction intended for use in identifying nucleotide sequences encoding other homologs of the three insecticidal proteins TIC901, TIC1201, and TIC407. The amplification primer sequences are set forth herein as (1) SEQ ID NO:11, a forward amplification twenty-one-mer primer sequence designated as prJWP139, corresponding to the coding sequence as set forth in SEQ ID NO:3 from nucleotide position 438 through 458 except that the nucleotide at position eighteen (18) within the oligonucleotide is redundant in that either an adenosine or a thymidine nucleotide is incorporated therein, resulting in two possible primer sequences, and (2) SEQ ID NO:12, a reverse amplification twenty-mer primer sequence designated as prJWP143, corresponding to the reverse complement of the sequence as set forth in SEQ ID NO:3 from nucleotide position 998 through 978, except that the nucleotide within the oligonucleotide at position four (4) and/or at position ten (10) is/are redundant in that either an adenosine or a thymidine nucleotide is incorporated at either position, resulting in four possible primer sequences. SEQ ID NO:11 and SEQ ID NO:12 are comprised of a nucleotide sequence that is biased toward codons preferred for use in gene sequences derived from *Bacillus thuringiensis* or other *Bacillus* species strains, in which the codons contain A and/or T in the third position for each codon represented within the sequence.

As indicated above, the amino acid sequence identified by Edmund Degradation of the about 38 kDa protein isolated and purified from spent culture media from fermentations using strain EG2158 was different by one amino acid from the corresponding sequence ultimately deduced from the open reading frame for TIC901 as set forth in SEQ ID NO:4. It was believed that the difference in amino acid sequences observed by Edmund degradation and the resulting TIC901 amino acid sequence deduced from the tic901 ORF could be the result of more than one gene present in strain EG2158, each gene encoding a different secreted insecticidal protein, and each secreted protein being about 38 kDa in size. In fact, if two or more genes were present in EG2158, each would have to be present on virtually identical HindIII fragments, or both could be present on the same HindIII fragment, or one may be sufficiently different from the tic901 coding sequence that it would not hybridize to a nucleotide sequence comprising SEQ ID NO:2 under stringent hybridization conditions. If each gene indeed encoded a homologous insecticidal protein, or at least a protein that was sufficiently similar to that protein encoded by the other such that the conserved sequences identified above were present within each coding sequence, then redundant primers such as those set forth in SEQ ID NO:11 and SEQ ID NO:12 may allow for the identification of the genes by amplification of the related coding sequences from a common sample in a thermal amplification reaction. For example, primers comprising the sequences as set forth in SEQ ID NO:11 and SEQ ID NO:12 would be expected to produce an amplicon of about 560 base pairs when using the TIC901, TIC1201, or TIC407 coding sequences as templates in a sample. In order to test this hypothesis, EG2158 total DNA was used as the template in a thermal amplification reaction using the amplification primers set forth in SEQ ID NO:11 and SEQ ID NO:12 under standard reaction conditions comprising 10-100 nanograms of bacterial genomic DNA template, 50 picomoles of each primer, 1×ROCHE amplification reaction buffer containing a final 1.5 mM divalent $Mg^{2+}$ cation concentration, 0.2 mM each deoxynucleotide triphosphate (dNTP), and 2.5 units of ROCHE TAQ Polymerase per 50 μl reaction volume, an initial denaturation cycle at 94° C. for two minutes, thirty (30) amplification cycles comprising a 94° C. denaturation phase for one minute, a 45° C. anneal phase for two (2) minutes, and a 72° C. primer extension phase for one (1) minute, followed by a final 72° C. primer extension and finishing phase for five (5) minutes, and a 4° C. soak. In addition, template DNA obtained from the following strains was also used in parallel thermal amplification reactions along with the amplification primers as set forth in SEQ ID NO:11 and SEQ ID NO:12: strain EG10650, strain EG4332, strain EG5552, strain EG5858, strain EG6489, strain EG6561, strain EG3618, strain EG6555, strain EG6618, and strain 86833. Samples of each thermal amplification reaction were analyzed by gel electrophoresis. The results are presented in Table 5.

TABLE 5

Amplicons Produced From *B. thuringiensis* Strains

| Template DNA | HindIII RFLP Type | Presence of Amplicon[1] |
|---|---|---|
| EG10650 | – | – |
| EG4332 | – | – |
| EG5552 | – | – |
| EG5858 | – | – |
| EG2158 | A | + |
| EG6489 | A | + |
| EG6561 | A | + |
| EG3618 | B | + |
| EG6555 | B | + |
| 86833 | B | + |
| EG6618 | C | + |

[1]amplicon produced in thermal amplification reaction using template DNA from indicated strain, amplification primers comprising the sequence as set forth in SEQ ID NO: 11 and SEQ ID NO: 12 under standard conditions as described above.

No amplicon was detected when DNA from strains EG10650, EG4332, EG5552, or EG5858 was used as template along with this particular primer set. This result suggests that these strains do not contain nucleotide sequences encoding a homolog of TIC901, TIC1201, and TIC407. However, each of the other strains tested appeared to produce a single amplicon of about 560 base pairs in length within the limits of resolution of the gel system used. Amplicons from each of the samples producing a positive reaction under these amplification conditions were cloned into a T-vector, and the nucleotide sequence was determined for randomly selected cloned amplicons from each thermal amplification reaction. Strains EG2158, EG6489, and EG6561 each produced an amplicon exhibiting a nucleotide sequence identical to the corresponding TIC901 coding sequence. Strains EG3618 and 86833 produced an amplicon exhibiting a nucleotide sequence identical to the corresponding TIC1201 coding sequence. Strain EG6555, which is a strain exhibiting a "B" type HindIII RFLP profile identical to that exhibited by strains EG3618 and 86833, also produced a 560 base pair amplicon. Strain EG6555 was not previously fully characterized, however, it was previously shown to generate a "B" type RFLP as set forth in Table 1, which corresponds to the RFLP phenotype exhibited by strain 86833 from which TIC1201 was isolated. Therefore it was anticipated that the homolog present in strain EG6555 encoded a protein substantially similar if not identical to TIC1201. Sequence analysis of an amplicon obtained from EG6555 was identical to the corresponding sequence obtained from strain 86833. As expected, strain EG6618 produced an amplicon exhibiting a nucleotide sequence identical to the corresponding TIC407 coding sequence.

Surprisingly, in addition to amplicons comprising the corresponding tic901 sequence, amplicons were derived from total DNA isolated from EG2158 that contained a second coding sequence that was different from the corresponding TIC901 nucleotide sequence identified using the redundant probe as set forth in SEQ ID NO:2. As anticipated, one amplicon obtained from EG2158 DNA was also comprised of about 560 nucleotides, but DNA sequence analysis of the clone resulted in the identification of an ORF (nucleotides 377 through 937 as set forth in SEQ ID NO:9) encoding a peptide sequence (amino acid sequence 96 through 282 as set forth in SEQ ID NO:10) that was substantially different from the corresponding peptide sequence for TIC901. This result suggested that there was yet at least one other nucleotide sequence present in strain EG2158 that may encode a protein homolog of TIC901 that could be considered as another member within the genus of proteins related to TIC901, TIC1201, and TIC407.

In order to fully characterize this second sequence identified from strain EG2158 DNA, inverse thermal amplification primers were designed based upon the second sequence that would specifically amplify the flanking sequences up and downstream of the second sequence. Inverse thermal amplification of EG2158 DNA was used to identify the complete open reading frame containing this second sequence. First, enzymes were selected for use in digesting EG2158 DNA that would (1) not cut within the second sequence identified above, and (2) cut frequently within *Bacillus* DNA as a result of having an AT rich sequence comprising the enzymes' recognition sequence. Considering these parameters, XbaI and SpeI were selected, but neither enzyme when used alone digested EG2158 DNA into fragments that could be easily circularized for use as inverse thermal amplification templates. However, since both enzymes produce compatible 5' overhanging ends, double-digestion of EG2158 DNA using both enzymes produced products of sufficiently small size that, when circularized, could be used as templates for inverse thermal amplification. Inverse amplification primers were designed based on the second sequence identified above, particularly sequences in which the corresponding tic901 sequence (SEQ ID NO:3) and the second sequence exhibited significant differences upon alignment.

Primer prJWP155 (SEQ ID NO:19) corresponds to and is the reverse complement of the second sequence as set forth in SEQ ID NO:9 from nucleotide 454-476). Primer prJWP156 (SEQ ID NO:20) corresponds to the second sequence as set forth in SEQ ID NO:9 from nucleotide 692-717. These two primers were used in an amplification reaction with double-digested, circularized EG2158 template DNA as indicated above, under conditions similar to those set forth above for inverse thermal amplification of EG6618 DNA. A single amplicon was obtained that was inserted into a T-vector to construct plasmid pJP290-1, and the nucleotide sequence of the inserted amplicon was determined. The inverse thermal amplification sequence derived using this method was assembled using DNA sequence analysis software and aligned with the second sequence identified above to construct a sequence as set forth in SEQ ID NO:9 that included a complete open reading frame encoding a peptide sequence designated as TIC417 as well as upstream and downstream flanking sequence.

To confirm the sequence, assembled in part from the second amplicon identified from EG2158 DNA as set forth above, and in part from the inverse thermal amplification reaction using primers prJWP155 and 156, two additional thermal amplification primers were designed that were complementary to the sequences flanking the open reading frame encoding TIC417 (prJWP168 and prJWP170). These primers would allow for the amplification of the complete TIC417 open reading frame along with a short length of DNA upstream and downstream of the TC417 ORF. Primer prJWP168 (SEQ ID NO:21) was constructed based in part on the sequence identified as being downstream of or 3' to the TIC417 ORF and functions to extend nucleotide sequence polymerization into the TIC417 ORF. The first five nucleotides of this primer correspond to nucleotides that are not present in the sequence identified as being present in plasmid pJP290-1 and also serve to incorporate a HindIII restriction site when coupled with bases 7-8 of SEQ ID NO:21. The terminal 39 nucleotides of prJWP168 correspond to the reverse complement of nucleotides 1148 through 1186 as set forth in SEQ ID NO:9. Primer prJWP170 (SEQ ID NO:22) was constructed based in part of the sequence identified as being upstream of or 5' to the TIC417 ORF and functions to enable primer extension in toward the 5' end of the TIC417 ORF. The first 9 nucleotides of this primer correspond to nucleotides that are not present in the sequence identified as being present in pJP290-1 and also serve to incorporate a BamHI restriction site recognition sequence upstream of the predicted TIC417 ATG initiation codon. The terminal 30 nucleotides of this primer correspond to nucleotides. The protein encoded by this different coding sequence was designated as TIC417. The amino acid sequence encoded by the cloned portion of the TIC417 amplicon is set forth in SEQ ID NO:10, and the cloned amplicon coding sequence is set forth in SEQ ID NO:9. The amino acid sequence of TIC417 is about 85% identical to the corresponding sequence from TIC901 and TIC1201, and is about 76% identical to the corresponding amino acid sequence of TIC407. It is believed that the protein fragment corresponding to the TIC417 coding sequence revealed in the TIC417 amplicon derived from EG2158 DNA is an insecticidal protein similar to TIC901, TIC1201 and TIC407, corresponding to a protein that is expressed as a precursor protein exhibiting a signal peptide of about 43 amino acid residues in length that terminates in a consensus signal peptide cleavage sequence corresponding to SER-GLN-GLN, which is processed by a signal peptidase to release an about 38 kDa, plus or minus about 2 kDa, mature protein into the extracellular space. It is also anticipated that the TIC417 mature amino terminal amino acid sequence may correspond to the amino acid sequence as set forth in SEQ ID NO:1, and that the TIC417 protein exhibits coleopteran species inhibitory insecticidal biological activity against corn rootworms and Colorado potato beetles.

Example 10

This example illustrates the design and use of degenerate probes and primers for use in identifying naturally occurring nucleotide sequences encoding all or part of insecticidal proteins derived from the proteins of the present invention or homologues thereof.

Based on an amino acid sequence alignment of the TIC901, TIC1201, TIC407 and TIC417 precursor proteins as set forth in FIG. 1, a number of regions of amino acid sequence identity were observed, and degenerate oligonucleotide sequence primers were designed based on the corresponding native nucleotide coding sequence for each protein, taking into consideration the profile for known Bacillus thuringiensis insecticidal proteins. While there are many conserved amino acid sequence segments to choose from within the alignment as set forth in FIG. 1 for designing degenerate primers, three segments were selected based on the position of the primer sequences within the coding region of the known TIC proteins and the unique size of the amplicons that would be expected to be generated in a thermal amplification reaction with these primers.

A first region or segment of conserved amino acid sequence corresponding to amino acid seventy-five (75) through amino acid eighty-three (83) as set forth in SEQ ID NO:4 was identified, and the corresponding nucleotide sequence encoding this amino acid segment from each of the sequences as set forth in SEQ ID NO:3, SEQ ID NO:5, SEQ ID NO:7, and SEQ ID NO:9 were then aligned. The consensus nucleotide sequence segment encoding this particular amino acid sequence segment was utilized to determine the scope of nucleotide sequences comprising the forward amplification primer sequence as set forth in SEQ ID NO:23 (prJWP200), as well as two other degenerate primers consisting of subsets of the SEQ ID NO:23 degenerate primer (SEQ ID NO:24-25, corresponding to prJWP201 and prJWP202 respectively).

A second region or segment of conserved amino acid sequence between the proteins of the present invention is exemplified by the amino acid sequence from about amino acid one-hundred-forty-seven (147) through about one-hundred-fifty-three (153) as set forth in SEQ ID NO:4. The nucleotide sequence encoding this amino acid segment from each of the sequences as set forth in SEQ ID NO:3, SEQ ID NO:5, SEQ ID NO:7, and SEQ ID NO:9 were then aligned. The consensus nucleotide sequence segment encoding this particular amino acid sequence segment was utilized to determine the scope of nucleotide sequences comprising the forward amplification primer sequence as set forth in SEQ ID NO:26 (prJWP203).

A third region or segment of conserved amino acid sequence between the proteins of the present invention is exemplified by the amino acid sequence from about amino acid two-hundred-seventy-five (275) through about amino acid two-hundred-eighty-three (283) as set forth in SEQ ID NO:4. The nucleotide sequence encoding this amino acid segment from each of the sequences as set forth in SEQ ID NO:3, SEQ ID NO:5, SEQ ID NO:7, and SEQ ID NO:9 were then aligned. The consensus nucleotide sequence segment encoding this particular amino acid sequence segment was utilized to determine the scope of nucleotide sequences comprising the reverse amplification primer sequence as set forth in SEQ ID NO:27 (prJWP204), as well as two other degenerate primers consisting of subsets of the SEQ ID NO:27 degenerate primer (SEQ ID NO:28-29, corresponding to prJWP205 and prJWP206 respectively).

Any combination of primers prJWP200, prJWP201, prJWP202, or prJWP203 with prJWP204, prJWP205, or prJWP206 can be used together in a thermal amplification reaction with a template nucleotide sequence encoding a TIC901, TIC1201, TIC407, TIC417 or a related secreted insecticidal protein or homologue thereof to produce an amplicon corresponding to a sequence segment that hybridizes to the corresponding sequences between the positions within the TIC coding sequences used for designing the primer sequences prJWP200-206. If any of the primers prJWP200-202 are used along with any of the primers prJWP204-206 in a thermal amplification reaction with an appropriate template in a sample, the production of an amplicon of from about 590 to about 650 base pairs in size is characteristically diagnostic for the presence of one or more coding sequences in the sample that are related to the sequences of the present invention. Generally, the diagnostic amplicon using primers within these ranges would consist of from about 617 to about 626 base pairs.

The use of any of the primers comprising SEQ ID NO:26 (prJWP203) along with any of the primers comprising SEQ ID NO:27-29 (prJWP204-206) in a thermal amplification reaction with an appropriate template in a sample, the production of an amplicon of from about 390 to about 415 base pairs in size is characteristically diagnostic for the presence of one or more coding sequences in the sample that are related to the sequences of the present invention. Generally, the diagnostic amplicon using primers within these ranges would consist of from about 400 to about 410 base pairs.

To exemplify the utility of these primers, primer prJWP200 (SEQ ID NO:23) was combined in a thermal amplification reaction with primer prJWP204 (SEQ ID NO:27), each at a concentration of at least about 1 pico-mole per micro-liter along with 1×TAQ amplification buffer, 0.2 molar each deoxy-nucleotide tri-phosphate (dATP, dTTP, dCTP, and dGTP), 2 millimolar $MgCl_2$, 2 units TAQ polymerase, and from about ten (10) to about one hundred (100) nano-grams of a sample of genomic DNA from strain EG2158 known to contain the coding sequences for TIC901 and TIC417. Thermal amplification cycle conditions consisted of an initial denaturation of about 2 minutes at 94° C. followed by 35 cycles of a denaturation step of 30 seconds at 94° C., an annealing step of 30 seconds at 50° C., and an extension step of 45 seconds at 72° C. followed by a final extension step of 7 minutes at 72° C. The temperature of the annealing step was decreased by 0.3° C. for each successive cycle so that the final annealing temperature was about 39.8° C.

A ten microliter sample was analyzed on a 1.2% TAE agarose gel and compared to a co-migrating 100 base pair ladder, and stained with ethidium bromide. The results indicated the production of an amplicon segment corresponding to about 620 base pairs. The about 620 base pair band was excised and the DNA recovered for cloning. Several independent clones representing this segment were isolated and the nucleotide sequence of each was obtained. As expected, a first sequence identical to the corresponding nucleotide sequence encoding TIC901 was identified (not including the primer sequences at either end of the clone, from about nucleotide position four-hundred-two (402) through about nucleotide position nine-hundred-seventy-four (974) as set forth in SEQ ID NO:3), and a second sequence identical to the corresponding nucleotide sequence encoding TIC417 was identified (not including the primer sequences at either end of the clone, from about nucleotide position four-hundred-sixty-four (464) through about nucleotide position one-thousand-thirty-six (1,036) as set forth in SEQ ID NO:9).

Surprisingly, a third sequence (SEQ ID NO:30) was also identified that did not correspond identically to any of the sequences set forth herein. However, the third sequence was substantially similar in nucleotide sequence to each of the sequences encoding a secreted insecticidal protein set forth herein, including tic901, tic1201, tic407, and tic417. As indicated in the examples above, it was quite unexpected to find the tic417 coding sequence in the strain EG2158 genomic DNA. It was even more surprising to identify yet a third nucleotide sequence that likely corresponds to a nucleotide segment that encodes yet a third secreted insecticidal protein from strain EG2158 that is different from those that have been set forth herein above, but which is sufficiently similar in sequence to be classified as one of the species within the genus of secreted insecticidal proteins encoded by a nucleotide sequence that hybridizes to one or more of the sequences set forth herein, and is exemplary of the novelty and utility of the degenerate oligonucleotide probes and primers exemplified herein for use in identifying sequences that encode secreted insecticidal proteins and that hybridize under stringent conditions to the related tic901, tic1201 tic07, and tic417 coding sequences as set forth herein.

The amino acid sequence encoded by the uninterrupted open reading frame as set forth in SEQ ID NO:30, which has had the twenty-six-mer degenerate oligonucleotide sequences deleted from both the 5' and 3' ends, is set forth in SEQ ID NO:31. The amino acid sequence set forth in SEQ ID NO:31 is substantially similar to the amino acid sequence of TIC901 from about amino acid position eighty-five (85) through about amino acid position two-hundred-seventy-four (274) as set forth in SEQ ID NO:4, containing only two (2) amino acids that are different from the analogous sequence in SEQ ID NO:4, corresponding to an about 98.9% identity between SEQ ID NO:31 and the corresponding sequence in SEQ ID NO:4. The amino acid sequence set forth in SEQ ID NO:31 is substantially similar to the amino acid sequence of TIC1201 from about amino acid position eighty-five (85) through about amino acid position two-hundred-seventy-four (274) as set forth in SEQ ID NO:6, containing only thirteen (13) amino acids that are different from the analogous sequence in SEQ ID NO:6, corresponding to an about 93.2% identity between SEQ ID NO:31 and the corresponding sequence in SEQ ID NO:6. The amino acid sequence set forth in SEQ ID NO:31 is substantially similar to the amino acid sequence of TIC417 from about amino acid position eighty-five (85) through about amino acid position two-hundred-seventy-four (274) as set forth in SEQ ID NO:10, containing only thirty (30) amino acids that are different from the analogous sequence in SEQ ID NO:10, corresponding to an about 83.7% identity between SEQ ID NO:31 and the corresponding sequence in SEQ ID NO:10. The amino acid sequence set forth in SEQ ID NO:31 is also substantially similar to the amino acid sequence of TIC401 from about amino acid position eighty-five (85) through about amino acid position two-hundred-seventy-four (274) as set forth in SEQ ID NO:8, containing forty-one (41) amino acids that are different from the analogous sequence in SEQ ID NO:8, corresponding to an about 78.4% identity between SEQ ID NO:31 and the corresponding sequence in SEQ ID NO:8.

In contrast to the results obtained when using DNA template from strains EG5858, EG4332, and EG5552 along with the primer set comprising SEQ ID NO:11 and SEQ ID NO:12 (as set forth in Table 5, above), DNA from these strains each produce an amplicon, the sequence of which appears to correspond to the TIC407 coding sequence, when using a primer set corresponding to primer prJWP200 and prJWP204. The corresponding coding sequence for a TIC407 homolog may be present on a large HindIII fragment in these strains and therefore may not have been readily available for identification when carrying out the initial screen as described above with a Southern blot using tic901 DNA as the probe, the results of which were set forth in Table 1.

Example 11

This example illustrates the identification of unique TIC901 related RFLP patterns and insecticidal protein coding sequences from Bacillus strains that produce in culture supernatant immunologically related TIC901 extracellular protein as determined using ELISA detection methods but whose DNA fails to result in the production of detectable thermal amplification products using standard tic901 thermal amplification detection methods.

Initial analyses as set forth using the examples above relied on the detection of insecticidal activity in culture supernatants grown overnight at 30 C in PYG medium followed by the detection of tic901 related sequences in B. thuringiensis strains when probed by the method of Southern using a TIC901 specific sequence. The total DNA from several hundreds of B. thuringiensis strains was analyzed. RFLP profiles were generated and compared. Thermal amplification from these DNA's using primers specific for tic901, tic1201, tic407, and tic417 determined that about twenty to twenty five percent of Bt strains contain such related sequences. It was believed that some TIC901 related sequences may not be detected using the RFLP and thermal amplification detection methods. Based on the extracellular protein profiles of Bt strains allowed to continue fermentation well into late log and through stationary phase and sporulation, a more direct approach using immunological methods would be useful for detecting Bt strains that produced TIC901 related proteins.

A Bt culture collection was arrayed into a 96-well format and stored as glycerol stocks at −80 C, and these were used as inoculum for micro-scale fermentations by transferring samples to deep well blocks (DWB's, QUIAGEN INC). Each sample was fermented in 1 milliliter of terrific broth (TB) per well. DWB's were sealed with AIRPORE tape sheets (QUIAGEN) and incubated at 30 C for from between 20 and 45 hours with shaking in a HiGro incubarot (GENOMIC SOLUTIONS/GENOMIC INSTRUMENTATION SERVICES) at 300 RPM. At the end of the fermentation time, twenty five units per milliliter of benzonase (SIGMA ALDRICH) were added to the culture broth to reduce viscosity and incubated at 30 C for an additional one hour. Solids, including cells and spores, were removed by centrifugation at 1900×g in a swinging bucket rotor at 4 C for thirty minutes and clarified supernatants were transferred in 200 microliter aliquots to shallow 96 well plates for storage at −80 C and further processing by ELISA analysis.

An ELISA method was developed for identification of supernatant broths containing TIC901 related proteins. 96 well NUNC Immuno MaxSorb plates were coated overnight at 4 C with 100 microliters per well of a 1:1000 diluted reverse-affinity purified rabbit polyclonal anti-TIC901 IgG antibody in coating buffer containing 15 millimolar sodium carbonate, 35 millimolar sodium bicarbonate, 150 millimolar NaCl, pH 9.6. Wells were washed three times with PBST (50 mM K/Na phosphate, 150 mM NaCl, 0.05% Tween 20, pH 7.4) and excess binding sites were blocked with 250 microliters of a 1% BSA solution in PBST for one hour at room temperature. Blocking buffer was discarded and each well was loaded with 200 microliters of a Bt culture supernatant diluted 1:75 (volume to volume) in PBST containing 0.2% BSA, followed by incubation at 4 C overnight. Each well was washed three times with PBST followed by the addition of 200 microliters per well of a 1:2000 diluted biotinylated polyclonal anti-TIC901 IgG in PBST containing 0.2% BSA. The biotinylated antibody solution was allowed to incubated for two hours at room temperature and washed three times as described above. The biotinylated antibody-TIC901 related protein complexes were detected by incubating 200 microliters per well of a 1:3000 diluted HRP conjugated streptavidin for two hours at room temperature, followed by three washes in PBST and the addition of 100 microliters per well of a TMP peroxidase substrate. Reactions were terminated by the addition of 100 microliters per well of a 3M phosphate solution. Absorbance of the individual wells was measured at a wavelength of 450 nanometers, and Bt strain supernatants determined to contain TIC901 related protein were determined by the average absorbance of negative controls plus three standard deviations.

Several strains were identified using this ELISA method that exhibited a positive ELISA result when compared to supernatants obtained from negative control cultures, but which also failed to result in the production of a thermal amplification product when using TIC901, TIC1201, TIC407, or TIC417 specific amplification primer pairs. Genomic DNA was obtained from one such ELISA positive/PCR negative strain previously designated as Bacillus thuringiensis strain EG4653 and a genomic plasmid expression library was constructed in the acrystalliferous strain EG10650. The EG10650 plasmid library derived from DNA of strain EG4653 was blotted to membranes and probed with the rabbit polyclonal anti-TIC901 IgG antibody described above. Positive clones were further purified and amplified and the DNA insert present in one such plasmid was sequenced. A complete TIC901 homologous protein was deduced from a single open reading frame. The homologous protein was designated as TIC431 and exhibits the amino acid sequence as set forth in SEQ ID NO:33. SEQ ID NO:32 consists of the open reading frame from which the TIC431 amino acid sequence was deduced. An alignment of the TIC431 amino acid sequence with the amino acid sequences of TIC901 and homologous proteins TIC1201, 407, and 417 is set forth in FIG. 1. A comparison of the deduced mature TIC431m to TIC901m, TIC1201m, TIC407m, and TIC417m shows that 431 exhibits about 75% identity to 407, about 79% identity to 901, about 80% identity to 1201, and about 95% identity to 417. Therefore, it is anticipated that other TIC431 homologous proteins would exhibit from about 75 to about 95% identity to TIC431 amino acid sequences. The deduced precursor protein consists of a predicted about 30 amino terminal amino acid sequence consistent with a signal peptide that exhibits a consensus type II signal peptidase cleavage sequence. In addition, the same or a substantially similar amino acid sequence exists between the signal peptide sequence and the deduced amino terminal amino acid of the mature peptide beginning at amino acid position 44 as set forth in SEQ ID NO:33. Thermal amplification primers as set forth in SEQ ID NO:23-26 and SEQ ID NO:27-29, consistent with the consensus amino acid sequences encoded by the nucleotide sequences as set forth in SEQ ID NO:32 from about 223 to about 249, or from about 439 to about 456, or from about 823 to about 846 are expected to produce amplicons that are diagnostic for the presence of SEQ ID NO:32, as well as other tic901 homologous insecticidal protein coding sequences.

The ELISA method coupled with the thermal amplification method should provide the skilled artisan with the means for identifying any nucleotide sequence encoding an insecticidal protein derived from a *Bacillus* species that exhibits from about 67% to about 99% or greater amino acid sequence identity to a TIC901 or a TIC901 homologous amino acid sequence as set forth herein.

One skilled in the art win recognize that other embodiments are possible using the probes and primers of the present invention to identify sequences encoding proteins of the present invention and to identify proteins of the present invention genes and proteins related thereto.

In summary, the above specification describes preferred embodiments of the present invention. It will be understood by those skilled in the art that, without departing from the scope and spirit of the present invention and without undue experimentation, the present invention can be performed within a wide range of equivalent parameters. While the present invention has been described in connection with specific embodiments thereof, it win be understood that it is capable of further modifications. The present invention is intended to cover any uses, variations, or adaptations of the invention following the principles of the invention in general. Various permutations and combination of the elements provided in all the claims that follow are possible and fall within the scope of this invention. All publications and patents mentioned in this specification are herein incorporated by reference as if each individual publication or patent was specially and individually stated to be incorporated by reference.

REFERENCES

Barry et al., 1992, Inhibitors of amino acid biosynthesis: Strategies for imparting glyphosate tolerance to crop plants. In: Biosynthesis and Molecular Regulation of Amino Acids in Plants. pp. 139-145. Singh, Flores, and Shannon Eds., American Society of Plant Physiologists, Rockville, Md.

Baum, J. A.; Coyle, D. M.; Gilbert, M. P.; Jany, C. S.; Gawron-Burke, C., 1990 Novel cloning vectors for *Bacillus thuringiensis;* 1983, Applied and Environmental Microbiology 56 (11): 3420-3428.

Bevan, Nature 304:184-187.

Callis et al., 1987, Genes & Develop. 1:1183-1200.

Crickmore et al., 1998, *Microbiol. Molecular Biol. Rev.* 62, pp. 807-813.

DeBarjac and Frachon, 1990, *Entomophaga* 35, pp. 233-240.

Diehn et al., 1996, *In: Genetic Engineering*, Ed. J. K. Setlow, Plenum Press, New York, N.Y., 18:83-99.

Diehn et al., 1998, Plant Physiology, 117:1433-1443.

Donovan et al., 1988, *Mol. Gen. Genet.* 214:365-372.

Ellis et al., 1987, EMBO Journal 6:11-16.

Estruch et al., 1996, *Proc. Natl. Acad. Sci. U.S.A.,* 93:5389-5394.

Fraley et al., 1983, *Proc. Natl. Acad. Sci. U.S.A.,* 80:4803.

Goding, Monoclonal Antibodies: Principles and Practice, $2^{nd}$ eds, Academic Press, NY, 1986. Harlow and Lane, 1988, Antibodies: A Laboratory Manual, Cold Spring Harbor Laboratory, Cold Spring Harbor, N.Y.

Hartley, J., 1988, Mol. Biol. 202: 913.

Herrera-Estrella, 1983, Nature 303:209-213.

Hess, 1987, *Intern Rev. Cytol.,* 107: 367.

Höfte et al., 1989, *Microbiol. Rev.* 53: 242-255,

Horsch et al., 1985, *Science,* 227:1229-1231.

Humason, Gretchen L., 1967, Animal Tissue Techniques, W.H. Freeman and Company.

Joshi, 1987, Nucl. Acids Res. 15:9627-9640.

Klee, 1985, Bio/Technol. 3:637-642.

Kostichka et al., 1996, J. Bacteriol. 178:2141-2144.

Kyte and Doolittle, 1982, J. Mol. Biol., 157:105-132.

Laemmli, 1973, Mol. Biol. 80:575-599.

Lu et al., 2000, J. Plant Phys., 156:277-283.

Ma et al., 1988, Nature 334:631-633.

Maliga, 1993, Trends in Biotechnology 11:101-106.

McElroy et al., 1990, Plant Cell 2:163-171.

Murray et al., 1989, Nucl. Acids. Res., 17:477-498.

Neuhaus et al., 1987, Theor. Appl. Genet., 75:30.

Nielsen et al., 1997, Protein Engineering 10:1-6.

Norton et al., 1985, Plasmid 13:211-214.

Odell et al., 1985, Nature 313:810-812.

Pena et al., 1987, Nature, 325:274.

Perlak et al., 1991, Proc. Natl. Acad. Sci. USA, 88:3324-3328.

Sambrook et al., 1989, *Molecular Cloning—A Laboratory Manual,* $2^{nd}$ Ed., Cold Spring Harbor Laboratory, Cold Spring Harbor, N.Y.

Schnepf et al., 1998, Microbiol. Molec. Biol. Rev. 62:775-806.

Turner et al., 1993, Endophytes: an alternative genome for crop improvement; International Crop Science Congress, Ames, Iowa, USA, 14-22 Jul. 1992, pp. 555-560.

Vasil et al., 1989, Plant Phys. 91:1575-1579.

Yanisch-Perron et al, 1985, Gene 33:103-119.

Zhou et al., 1983, Mol. Cell Biol., 10:4529-4537.

U.S. Pat. No. 6,489,542

U.S. Pat. No. 6,448,476

U.S. Pat. No. 6,279,369

U.S. Pat. No. 6,242,669

U.S. Pat. No. 6,204,435

U.S. Pat. No. 6,107,549

U.S. Pat. No. 6,063,597

U.S. Pat. No. 5,888,801

U.S. Pat. No. 5,872,212

U.S. Pat. No. 5,877,012

U.S. Pat. No. 5,866,326

U.S. Pat. No. 5,849,870

U.S. Pat. No. 5,837,848

U.S. Pat. No. 5,759,538

U.S. Pat. No. 5,689,052

U.S. Pat. No. 5,569,834

U.S. Pat. No. 5,500,365

U.S. Pat. No. 5,424,412

U.S. Pat. No. 5,349,124

U.S. Pat. No. 5,229,112

U.S. Pat. No. 5,135,867

U.S. Pat. No. 5,080,897

U.S. Pat. No. 4,935,353

U.S. Pat. No. 4,695,462

U.S. Pat. No. 4,695,455

U.S. Pat. No. 4,554,101

WO96/10083.

WO94/21795.

WO95/24492.

EPO 0 120 516.

SEQUENCE LISTING

<160> NUMBER OF SEQ ID NOS: 33

<210> SEQ ID NO 1
<211> LENGTH: 15
<212> TYPE: PRT
<213> ORGANISM: Bacillus thuringiensis

<400> SEQUENCE: 1

Val Ile Gly Pro Tyr Ala Glu Ser Tyr Ile Asp Arg Val Gln Asp
 1               5                  10                  15

<210> SEQ ID NO 2
<211> LENGTH: 45
<212> TYPE: DNA
<213> ORGANISM: Artificial Sequence
<220> FEATURE:
<223> OTHER INFORMATION: tic gene probe encoding SEQ ID NO 1

<400> SEQUENCE: 2
gtaattggac catatgcaga atcatatatt gatacgagta caaga             45

<210> SEQ ID NO 3
<211> LENGTH: 1253
<212> TYPE: DNA
<213> ORGANISM: Bacillus thuringiensis
<220> FEATURE:
<221> NAME/KEY: CDS
<222> LOCATION: (153)..(1253)
<223> OTHER INFORMATION:

<400> SEQUENCE: 3
aattatgatt ttaatattct tatgttattc ctataatata caataaaagc ataattatcc     60
ttcatattat gtttataaat ttaataaaat acataaaaat agagtgttat aatattttg    120 aaagcgttat caagagtgat ggagggataa tt atg aaa aat aga ttt tca aaa     173
                                    Met Lys Asn Arg Phe Ser Lys
                                      1               5 gtg gca tta tgc acc gta ccg att tta atg gtt tct aca ttc gcc agt     221
Val Ala Leu Cys Thr Val Pro Ile Leu Met Val Ser Thr Phe Ala Ser
         10                  15                  20 tca agc atg tca gct ttt gct gca gaa gcc aaa tca cca gat tta aat     269
Ser Ser Met Ser Ala Phe Ala Ala Glu Ala Lys Ser Pro Asp Leu Asn
 25                  30                  35 gta tct caa caa gta ata ggt ccc tat gcc gaa tct tat att gat att     317
Val Ser Gln Gln Val Ile Gly Pro Tyr Ala Glu Ser Tyr Ile Asp Ile
 40                  45                  50                  55 gtg cag gat aga atg aaa caa agg gat aag gga tca aaa tta act ggt     365
Val Gln Asp Arg Met Lys Gln Arg Asp Lys Gly Ser Lys Leu Thr Gly
             60                  65                  70 aaa cca ata aat atg caa gaa caa ata ata gat ggg tgg ttt cta gct     413
Lys Pro Ile Asn Met Gln Glu Gln Ile Ile Asp Gly Trp Phe Leu Ala
         75                  80                  85 aga ttt tgg ata ttt aag gat caa aac aat aac cat cag aca aat aga     461
Arg Phe Trp Ile Phe Lys Asp Gln Asn Asn Asn His Gln Thr Asn Arg
     90                  95                 100 ttt ata tcc tgg ttt aaa gat aat att gct agt tca aaa ggg tat aat     509
Phe Ile Ser Trp Phe Lys Asp Asn Ile Ala Ser Ser Lys Gly Tyr Asn
105                 110                 115 agt att gcg gag caa atg ggt tta aaa ata gaa gca gaa aac gat atg     557
Ser Ile Ala Glu Gln Met Gly Leu Lys Ile Glu Ala Glu Asn Asp Met
120                 125                 130                 135 gat gta aca aat ata gat tat aca tct aag aca ggc gat acc att tat     605
Asp Val Thr Asn Ile Asp Tyr Thr Ser Lys Thr Gly Asp Thr Ile Tyr

|     |     |     |     |     |     |     |     |     |     |     |     |     |     |     |     |      |
| --- | --- | --- | --- | --- | --- | --- | --- | --- | --- | --- | --- | --- | --- | --- | --- | --- |
|     |     |     | 140 |     |     |     |     | 145 |     |     |     |     | 150 |     |     |      |
| aat | ggt | att | tca | gaa | ttg | aaa | aat | tat | aca | gga | tca | act | caa | aag | atg | 653  |
| Asn | Gly | Ile | Ser | Glu | Leu | Lys | Asn | Tyr | Thr | Gly | Ser | Thr | Gln | Lys | Met |      |
|     |     | 155 |     |     |     |     | 160 |     |     |     |     | 165 |     |     |     |      |
| aaa | aca | gat | agt | ttt | caa | aga | gat | tat | aca | aaa | tca | gaa | tct | act | tca | 701  |
| Lys | Thr | Asp | Ser | Phe | Gln | Arg | Asp | Tyr | Thr | Lys | Ser | Glu | Ser | Thr | Ser |      |
|     | 170 |     |     |     |     | 175 |     |     |     |     | 180 |     |     |     |     |      |
| gta | act | aat | gga | tta | caa | tta | gga | ttt | aaa | gtt | gct | gct | aaa | gga | gta | 749  |
| Val | Thr | Asn | Gly | Leu | Gln | Leu | Gly | Phe | Lys | Val | Ala | Ala | Lys | Gly | Val |      |
| 185 |     |     |     |     | 190 |     |     |     |     | 195 |     |     |     |     |     |      |
| gtt | gct | ttg | gct | ggg | gca | gac | ttt | gaa | acc | agt | gtt | act | tat | aat | cta | 797  |
| Val | Ala | Leu | Ala | Gly | Ala | Asp | Phe | Glu | Thr | Ser | Val | Thr | Tyr | Asn | Leu |      |
| 200 |     |     |     |     | 205 |     |     |     |     | 210 |     |     |     |     | 215 |      |
| tca | act | act | aca | act | gaa | aca | aat | aca | ata | tca | gac | aag | ttt | act | gtc | 845  |
| Ser | Thr | Thr | Thr | Thr | Glu | Thr | Asn | Thr | Ile | Ser | Asp | Lys | Phe | Thr | Val |      |
|     |     |     |     | 220 |     |     |     |     | 225 |     |     |     |     | 230 |     |      |
| cca | tct | caa | gaa | gtt | aca | ttg | cct | cca | gga | cat | aaa | gcg | ata | gtg | aaa | 893  |
| Pro | Ser | Gln | Glu | Val | Thr | Leu | Pro | Pro | Gly | His | Lys | Ala | Ile | Val | Lys |      |
|     |     |     | 235 |     |     |     |     | 240 |     |     |     |     | 245 |     |     |      |
| cat | gat | tta | aga | aaa | atg | gtt | tat | tct | ggt | act | cat | gat | cta | aag | ggt | 941  |
| His | Asp | Leu | Arg | Lys | Met | Val | Tyr | Ser | Gly | Thr | His | Asp | Leu | Lys | Gly |      |
|     | 250 |     |     |     |     | 255 |     |     |     |     | 260 |     |     |     |     |      |
| gat | tta | att | gtg | agt | ttt | aat | gat | aaa | gag | att | gta | caa | aaa | ttt | att | 989  |
| Asp | Leu | Ile | Val | Ser | Phe | Asn | Asp | Lys | Glu | Ile | Val | Gln | Lys | Phe | Ile |      |
| 265 |     |     |     |     | 270 |     |     |     |     | 275 |     |     |     |     |     |      |
| tat | cca | aat | tat | aga | gaa | att | aat | tta | tct | gat | atc | cgt | gaa | act | atg | 1037 |
| Tyr | Pro | Asn | Tyr | Arg | Glu | Ile | Asn | Leu | Ser | Asp | Ile | Arg | Glu | Thr | Met |      |
| 280 |     |     |     |     | 285 |     |     |     |     | 290 |     |     |     |     | 295 |      |
| att | gaa | att | gat | gaa | tgg | aat | cat | gta | aac | cct | gtg | aat | ttt | tat | gaa | 1085 |
| Ile | Glu | Ile | Asp | Glu | Trp | Asn | His | Val | Asn | Pro | Val | Asn | Phe | Tyr | Glu |      |
|     |     |     |     | 300 |     |     |     |     | 305 |     |     |     |     | 310 |     |      |
| tta | gtt | ggg | gtc | aaa | aat | cat | ata | aaa | aat | ggt | gaa | act | ttg | tat | ata | 1133 |
| Leu | Val | Gly | Val | Lys | Asn | His | Ile | Lys | Asn | Gly | Glu | Thr | Leu | Tyr | Ile |      |
|     |     |     | 315 |     |     |     |     | 320 |     |     |     |     | 325 |     |     |      |
| gat | act | cca | gct | aaa | ttt | atg | ttt | aat | ggt | gct | aat | cca | tat | tat | aga | 1181 |
| Asp | Thr | Pro | Ala | Lys | Phe | Met | Phe | Asn | Gly | Ala | Asn | Pro | Tyr | Tyr | Arg |      |
|     | 330 |     |     |     |     | 335 |     |     |     |     | 340 |     |     |     |     |      |
| gca | aca | ttt | aca | gaa | tac | gac | ggg | aat | aat | aat | cct | gtt | caa | aca | aag | 1229 |
| Ala | Thr | Phe | Thr | Glu | Tyr | Asp | Gly | Asn | Asn | Asn | Pro | Val | Gln | Thr | Lys |      |
| 345 |     |     |     |     | 350 |     |     |     |     | 355 |     |     |     |     |     |      |
| gta | tta | agt | gaa | aac | ttt | aaa | ttg |     |     |     |     |     |     |     |     | 1253 |
| Val | Leu | Ser | Glu | Asn | Phe | Lys | Leu |     |     |     |     |     |     |     |     |      |
| 360 |     |     |     |     | 365 |     |     |     |     |     |     |     |     |     |     |      |

<210> SEQ ID NO 4
<211> LENGTH: 367
<212> TYPE: PRT
<213> ORGANISM: Bacillus thuringiensis

<400> SEQUENCE: 4

Met Lys Asn Arg Phe Ser Lys Val Ala Leu Cys Thr Val Pro Ile Leu
1               5                   10                  15

Met Val Ser Thr Phe Ala Ser Ser Met Ser Ala Phe Ala Ala Glu
            20                  25                  30

Ala Lys Ser Pro Asp Leu Asn Val Ser Gln Gln Val Ile Gly Pro Tyr
        35                  40                  45

Ala Glu Ser Tyr Ile Asp Ile Val Gln Asp Arg Met Lys Gln Arg Asp
    50                  55                  60

Lys Gly Ser Lys Leu Thr Gly Lys Pro Ile Asn Met Gln Glu Gln Ile

```
                65                  70                  75                  80
Ile Asp Gly Trp Phe Leu Ala Arg Phe Trp Ile Phe Lys Asp Gln Asn
                        85                  90                  95
Asn Asn His Gln Thr Asn Arg Phe Ile Ser Trp Phe Lys Asp Asn Ile
            100                 105                 110
Ala Ser Ser Lys Gly Tyr Asn Ser Ile Ala Glu Gln Met Gly Leu Lys
            115                 120                 125
Ile Glu Ala Glu Asn Asp Met Asp Val Thr Asn Ile Asp Tyr Thr Ser
        130                 135                 140
Lys Thr Gly Asp Thr Ile Tyr Asn Gly Ile Ser Glu Leu Lys Asn Tyr
145                 150                 155                 160
Thr Gly Ser Thr Gln Lys Met Lys Thr Asp Ser Phe Gln Arg Asp Tyr
                165                 170                 175
Thr Lys Ser Glu Ser Thr Ser Val Thr Asn Gly Leu Gln Leu Gly Phe
            180                 185                 190
Lys Val Ala Ala Lys Gly Val Val Ala Leu Ala Gly Ala Asp Phe Glu
            195                 200                 205
Thr Ser Val Thr Tyr Asn Leu Ser Thr Thr Thr Glu Thr Asn Thr
        210                 215                 220
Ile Ser Asp Lys Phe Thr Val Pro Ser Gln Glu Val Thr Leu Pro Pro
225                 230                 235                 240
Gly His Lys Ala Ile Val Lys His Asp Leu Arg Lys Met Val Tyr Ser
                245                 250                 255
Gly Thr His Asp Leu Lys Gly Asp Leu Ile Val Ser Phe Asn Asp Lys
            260                 265                 270
Glu Ile Val Gln Lys Phe Ile Tyr Pro Asn Tyr Arg Glu Ile Asn Leu
        275                 280                 285
Ser Asp Ile Arg Glu Thr Met Ile Glu Ile Asp Glu Trp Asn His Val
        290                 295                 300
Asn Pro Val Asn Phe Tyr Glu Leu Val Gly Val Lys Asn His Ile Lys
305                 310                 315                 320
Asn Gly Glu Thr Leu Tyr Ile Asp Thr Pro Ala Lys Phe Met Phe Asn
                325                 330                 335
Gly Ala Asn Pro Tyr Tyr Arg Ala Thr Phe Thr Glu Tyr Asp Gly Asn
            340                 345                 350
Asn Asn Pro Val Gln Thr Lys Val Leu Ser Glu Asn Phe Lys Leu
            355                 360                 365

<210> SEQ ID NO 5
<211> LENGTH: 1621
<212> TYPE: DNA
<213> ORGANISM: Bacillus thuringiensis
<220> FEATURE:
<221> NAME/KEY: CDS
<222> LOCATION: (530)..(1621)
<223> OTHER INFORMATION:

<400> SEQUENCE: 5
actagttttt tcataatggc ataagcggga tgatgatctt gttttttacg atgttcaata      60
tccaatgtgt gccttttctat atcaatcgca cgatataaat aacactatttt ccctttgaat     120 tttatatagg tttcatctaa ttttcaagac atgtggttgt tttgcgtttt cttcttccaa     180
atttgataaa tcaagctccc atattcatga atccagcgca taatgattgt gggatgaact     240
gaaacatcac gatagcttaa agcaaaacga caatagtagc ggacggctac cataataata     300
tcttgtttga actgtttccc tttaaaatat cacatttgtg attctcctcg atgctttttt     360
```

-continued

```
tagagtgtag cttcatctag aacactttgc aatagaacca ttcctttgat atacaattaa     420
accacattta tccttcatgg aatgtttata tattaaagaa tataaaaaaa catacgatgt     480
tataattaat ttgaaagcgt taacaaaaat gaatgatgga gggataatt atg aaa tac     538
                                                     Met Lys Tyr
                                                       1 aag ttt tca aaa gtc gtt aag tgt act tta cca gct tta atg att act       586
Lys Phe Ser Lys Val Val Lys Cys Thr Leu Pro Ala Leu Met Ile Thr
      5              10                  15 aca ttc gtt act cca agt atg gca gtt ttt gcc gca gaa acc aag tcg       634
Thr Phe Val Thr Pro Ser Met Ala Val Phe Ala Ala Glu Thr Lys Ser
 20              25                  30                  35 cca aat cta aat gca tct caa caa gca ata act cca tat gct gaa tct       682
Pro Asn Leu Asn Ala Ser Gln Gln Ala Ile Thr Pro Tyr Ala Glu Ser
             40                  45                  50 tat att gat act gtt caa gat aga atg aaa caa aga gat agg gaa tca       730
Tyr Ile Asp Thr Val Gln Asp Arg Met Lys Gln Arg Asp Arg Glu Ser
                 55                  60                  65 aaa cta act ggt aaa cca ata aat atg caa gaa caa ata ata gat gga       778
Lys Leu Thr Gly Lys Pro Ile Asn Met Gln Glu Gln Ile Ile Asp Gly
          70                  75                  80 tgg ttt tta gct aga ttc tgg ata ttt aaa gat caa aat aac aat cat       826
Trp Phe Leu Ala Arg Phe Trp Ile Phe Lys Asp Gln Asn Asn Asn His
 85                  90                  95 caa aca aat aga ttt ata tcc tgg ttt aaa gat aat ctt gct agt tcg       874
Gln Thr Asn Arg Phe Ile Ser Trp Phe Lys Asp Asn Leu Ala Ser Ser
100                 105                 110                 115 aag ggg tat gac agt ata gca gaa caa atg ggc tta aaa ata gaa gca       922
Lys Gly Tyr Asp Ser Ile Ala Glu Gln Met Gly Leu Lys Ile Glu Ala
                    120                 125                 130 tta aat gat atg gat gta aca aat att gat tat aca tct aaa aca ggt       970
Leu Asn Asp Met Asp Val Thr Asn Ile Asp Tyr Thr Ser Lys Thr Gly
             135                 140                 145 gat acc ata tat aat gga att tct gaa cta aca aat tat aca gga aca      1018
Asp Thr Ile Tyr Asn Gly Ile Ser Glu Leu Thr Asn Tyr Thr Gly Thr
         150                 155                 160 acc caa aaa atg aaa acc gat agt ttt caa aga gat tat aca aaa tct      1066
Thr Gln Lys Met Lys Thr Asp Ser Phe Gln Arg Asp Tyr Thr Lys Ser
165                 170                 175 gaa tcc act tca gta aca aat ggg tta caa tta gga ttt aaa gtt gct      1114
Glu Ser Thr Ser Val Thr Asn Gly Leu Gln Leu Gly Phe Lys Val Ala
180                 185                 190                 195 gct aag gga gta gtt gca tta gca ggt gca gat ttt gaa aca agt gtt      1162
Ala Lys Gly Val Val Ala Leu Ala Gly Ala Asp Phe Glu Thr Ser Val
                200                 205                 210 acc tat aat tta tca tct act aca act gaa aca aat aca ata tcg gat      1210
Thr Tyr Asn Leu Ser Ser Thr Thr Thr Glu Thr Asn Thr Ile Ser Asp
             215                 220                 225 aag ttt act gtt cca tct caa gaa gtt aca tta tcc cca gga cat aaa      1258
Lys Phe Thr Val Pro Ser Gln Glu Val Thr Leu Ser Pro Gly His Lys
         230                 235                 240 gca gtg gtg aaa cat gat ttg aga aaa atg gtg tat ttt ggg act cat      1306
Ala Val Val Lys His Asp Leu Arg Lys Met Val Tyr Phe Gly Thr His
245                 250                 255 gat tta aag ggt gat tta aaa gta ggt ttt aat gat aaa gag att gta      1354
Asp Leu Lys Gly Asp Leu Lys Val Gly Phe Asn Asp Lys Glu Ile Val
260                 265                 270                 275 caa aaa ttt att tat cca aat tat aga tca att gat tta tct gat att      1402
Gln Lys Phe Ile Tyr Pro Asn Tyr Arg Ser Ile Asp Leu Ser Asp Ile
```

```
                    280                 285                 290
cgt aaa aca atg att gaa att gat aaa tgg aat cat gta aat acc att       1450
Arg Lys Thr Met Ile Glu Ile Asp Lys Trp Asn His Val Asn Thr Ile
            295                 300                 305 gac ttt tat caa tta gtt gga gtt aaa aat cat ata aaa aat ggt gat       1498
Asp Phe Tyr Gln Leu Val Gly Val Lys Asn His Ile Lys Asn Gly Asp
            310                 315                 320 act tta tat ata gat acc ccg gcc gaa ttt aca ttt aat gga gct aat       1546
Thr Leu Tyr Ile Asp Thr Pro Ala Glu Phe Thr Phe Asn Gly Ala Asn
            325                 330                 335 cca tat tat aga gca aca ttt aca gaa tac gac gag aac gga aat cct       1594
Pro Tyr Tyr Arg Ala Thr Phe Thr Glu Tyr Asp Glu Asn Gly Asn Pro
340                 345                 350                 355 gtt caa aca aag att tta agt gga aat                                   1621
Val Gln Thr Lys Ile Leu Ser Gly Asn
                360

<210> SEQ ID NO 6
<211> LENGTH: 364
<212> TYPE: PRT
<213> ORGANISM: Bacillus thuringiensis

<400> SEQUENCE: 6

Met L

```
                    260                 265                 270
Glu Ile Val Gln Lys Phe Ile Tyr Pro Asn Tyr Arg Ser Ile Asp Leu
            275                 280                 285

Ser Asp Ile Arg Lys Thr Met Ile Glu Ile Asp Lys Trp Asn His Val
        290                 295                 300

Asn Thr Ile Asp Phe Tyr Gln Leu Val Gly Val Lys Asn His Ile Lys
305                 310                 315                 320

Asn Gly Asp Thr Leu Tyr Ile Asp Thr Pro Ala Glu Phe Thr Phe Asn
                325                 330                 335

Gly Ala Asn Pro Tyr Tyr Arg Ala Thr Phe Thr Glu Tyr Asp Glu Asn
            340                 345                 350

Gly Asn Pro Val Gln Thr Lys Ile Leu Ser Gly Asn
            355                 360

<210> SEQ ID NO 7
<211> LENGTH: 1552
<212> TYPE: DNA
<213> ORGANISM: Bacillus thuringiensis
<220> FEATURE

```
cct caa aaa atg aaa tca gat agt ttt caa aga gat tat acc aaa tct      705
Pro Gln Lys Met Lys Ser Asp Ser Phe Gln Arg Asp Tyr Thr Lys Ser
    165                 170                 175 caa tca acc tca gta aca aat ggg tta caa tta gga gtt aaa gtt tct      753
Gln Ser Thr Ser Val Thr Asn Gly Leu Gln Leu Gly Val Lys Val Ser
180                 185                 190                 195 gcc aaa ggt acg gtt gtc tta gga gag gca agc ctt gaa aca agc gtt      801
Ala Lys Gly Thr Val Val Leu Gly Glu Ala Ser Leu Glu Thr Ser Val
                200                 205                 210 act tat aat tta tcg tct act gca act gaa aca gat aca aca tcg gac      849
Thr Tyr Asn Leu Ser Ser Thr Ala Thr Glu Thr Asp Thr Thr Ser Asp
            215                 220                 225 aag ttt act gtc cca tcc caa gaa gtt aca tta cca cca gga cat aaa      897
Lys Phe Thr Val Pro Ser Gln Glu Val Thr Leu Pro Pro Gly His Lys
        230                 235                 240 gca gta att aag cat gat tta aga aaa atg gtg tat tct ggt acg cat      945
Ala Val Ile Lys His Asp Leu Arg Lys Met Val Tyr Ser Gly Thr His
    245                 250                 255 gac tta aag ggg gat tta aaa gta gct ttt aac gat aaa gca att gta      993
Asp Leu Lys Gly Asp Leu Lys Val Ala Phe Asn Asp Lys Ala Ile Val
260                 265                 270                 275 caa aaa ttt att tat cca aat tat aga tct ata aat tta tct gat att     1041
Gln Lys Phe Ile Tyr Pro Asn Tyr Arg Ser Ile Asn Leu Ser Asp Ile
                280                 285                 290 cgt aaa aca atg aaa gaa att gat gaa tgg aat cat gta aaa ccc att     1089
Arg Lys Thr Met Lys Glu Ile Asp Glu Trp Asn His Val Lys Pro Ile
            295                 300                 305 gat ttt tat caa ctg gtt gga ata aaa aat cat ata aaa aat ggg gat     1137
Asp Phe Tyr Gln Leu Val Gly Ile Lys Asn His Ile Lys Asn Gly Asp
        310                 315                 320 acc tta tat ata gag act cca gct aaa ttt att ttt aat gga gct aat     1185
Thr Leu Tyr Ile Glu Thr Pro Ala Lys Phe Ile Phe Asn Gly Ala Asn
    325                 330                 335 gta tat tat aga gca act ttt aca gaa tat gat aag gat gga aaa cct     1233
Val Tyr Tyr Arg Ala Thr Phe Thr Glu Tyr Asp Lys Asp Gly Lys Pro
340                 345                 350                 355 gtt caa ttc aac aaa ttt tta agt gaa aat tac aag tta tagaggaagt      1282
Val Gln Phe Asn Lys Phe Leu Ser Glu Asn Tyr Lys Leu
                360                 365 aaagatgccg tagtgagatc gtttcacagc tactgagtat tcaaataata cacgggaaaa   1342
ttcaccttcc tggaaggacg gatttacttt ttttacggag gaacttgttt tatacatcaa   1402
aatgtttttt tatgaggttt gtgtattctt atttgagcct ggaacggaac cattttgagt   1462
aagcttaatt tgacttggaa atgtattttt attaccttat tacgtgaaca atggcctata   1522
aacgtgccac acaggaatgg gaggacgagt                                    1552
```

```
<210> SEQ ID NO 8
<211> LENGTH: 368
<212> TYPE: PRT
<213> ORGANISM: Bacillus thuringiensis

<400> SEQUENCE: 8

Met Lys Tyr Lys Ser Ser Lys Val Ala Ile Cys Thr Leu Ser Ala Leu
1               5                   10                  15

Met Leu Ser Thr Ile Gly Thr Ser Ser Met Ser Thr Phe Ala Ala Glu
            20                  25                  30

Thr Thr Leu Pro Gly Gln Thr Leu Lys Glu Gln Ser Ile Thr Pro Arg
        35                  40                  45
```

Ala Glu Ser Tyr Ile Asp Ile Val Gln Asp Arg Met Lys Gln Arg Asp
 50                  55                  60

Ile Glu Ser Lys Arg Thr Gly Lys Pro Ile Asn Met Gln Glu Gln Ile
 65                  70                  75                  80

Ile Asp Gly Trp Phe Leu Ala Arg Phe Trp Ile Phe Lys Asp Gln Asn
                 85                  90                  95

Asn Asn His Gln Thr Asn Arg Phe Ile Thr Trp Phe Lys Asn Asn Val
             100                 105                 110

Ala Ser Ser Lys Gly Tyr Glu Gly Ile Ala Glu Gln Met Gly Leu Lys
         115                 120                 125

Ile Glu Ser Met Ser Asp Met Asn Val Ser Asn Ile Asn Tyr Thr Gly
130                 135                 140

Lys Lys Gly Asp Thr Ile Tyr Asn Gly Val Ser Glu Leu Glu Asn Lys
145                 150                 155                 160

Met Gly Thr Pro Gln Lys Met Lys Ser Asp Ser Phe Gln Arg Asp Tyr
                165                 170                 175

Thr Lys Ser Gln Ser Thr Ser Val Thr Asn Gly Leu Gln Leu Gly Val
            180                 185                 190

Lys Val Ser Ala Lys Gly Thr Val Val Leu Gly Glu Ala Ser Leu Glu
        195                 200                 205

Thr Ser Val Thr Tyr Asn Leu Ser Ser Thr Ala Thr Glu Thr Asp Thr
210                 215                 220

Thr Ser Asp Lys Phe Thr Val Pro Ser Gln Glu Val Thr Leu Pro Pro
225                 230                 235                 240

Gly His Lys Ala Val Ile Lys His Asp Leu Arg Lys Met Val Tyr Ser
                245                 250                 255

Gly Thr His Asp Leu Lys Gly Asp Leu Lys Val Ala Phe Asn Asp Lys
            260                 265                 270

Ala Ile Val Gln Lys Phe Ile Tyr Pro Asn Tyr Arg Ser Ile Asn Leu
        275                 280                 285

Ser Asp Ile Arg Lys Thr Met Lys Glu Ile Asp Glu Trp Asn His Val
290                 295                 300

Lys Pro Ile Asp Phe Tyr Gln Leu Val Gly Ile Lys Asn His Ile Lys
305                 310                 315                 320

Asn Gly Asp Thr Leu Tyr Ile Glu Thr Pro Ala Lys Phe Ile Phe Asn
                325                 330                 335

Gly Ala Asn Val Tyr Tyr Arg Ala Thr Phe Thr Glu Tyr Asp Lys Asp
            340                 345                 350

Gly Lys Pro Val Gln Phe Asn Lys Phe Leu Ser Glu Asn Tyr Lys Leu
        355                 360                 365

<210> SEQ ID NO 9
<211> LENGTH: 1378
<212> TYPE: DNA
<213> ORGANISM: Bacillus thuringiensis
<220> FEATURE:
<221> NAME/KEY: CDS
<222> LOCATION: (215)..(1306)
<223> OTHER INFORMATION:

<400> SEQUENCE: 9
cagtggatag gaatttgttt tcgtgctagg tatcaattta atttgttcta taagataagt        60
gaagtacgat caaaatgaat acttttgtgt attagatcaa taggtaaaat aataataaat       120
tttatatttg aaccttaaaa aattatttaa tcaaatcttt ttcactttaa aaacaaaata       180

-continued

```
tccagaaaaa acaatagtta acggagggat aata atg aaa tac aag tca tca aaa       235
                                     Met Lys Tyr Lys Ser Ser Lys
                                      1               5 gta gca atg tgt aca tta tca gct tta atg ctt tcg aca atc gcc act         283
Val Ala Met Cys Thr Leu Ser Ala Leu Met Leu Ser Thr Ile Ala Thr
         10                  15                  20 cca agt ata tct gtt ttc gct gca gaa aca act tcg tca cat gcg gtt         331
Pro Ser Ile Ser Val Phe Ala Ala Glu Thr Thr Ser Ser His Ala Val
 25                  30                  35 act aat cag caa aca att acg cag cgt gca gaa tct tat att gat att         379
Thr Asn Gln Gln Thr Ile Thr Gln Arg Ala Glu Ser Tyr Ile Asp Ile
 40                  45                  50                  55 gtg cac aat aga atg aaa caa aga gat att gaa tca aaa atg aca ggt         427
Val His Asn Arg Met Lys Gln Arg Asp Ile Glu Ser Lys Met Thr Gly
                 60                  65                  70 aaa tcc att aat atg caa gaa caa ata att gat gga tgg ttt tta gct         475
Lys Ser Ile Asn Met Gln Glu Gln Ile Ile Asp Gly Trp Phe Leu Ala
                     75                  80                  85 aga ttt tgg ata ttt aag gat caa aat aat agt cac caa aca aat aga         523
Arg Phe Trp Ile Phe Lys Asp Gln Asn Asn Ser His Gln Thr Asn Arg
                 90                  95                 100 ttt att tca tgg ttt aag gat aat ttg gct agc cca gga ggg tat gat         571
Phe Ile Ser Trp Phe Lys Asp Asn Leu Ala Ser Pro Gly Gly Tyr Asp
            105                 110                 115 agt atc gct gaa cag atg ggc cta aaa gta gca gca tta aat gat atg         619
Ser Ile Ala Glu Gln Met Gly Leu Lys Val Ala Ala Leu Asn Asp Met
120                 125                 130                 135 gat ata tca aat gta aat tat act tct aag aca ggg gat act ata tat         667
Asp Ile Ser Asn Val Asn Tyr Thr Ser Lys Thr Gly Asp Thr Ile Tyr
                140                 145                 150 aat ggt gtt tca gaa tta aaa aat atc aca gga aca act caa aaa atg        715
Asn Gly Val Ser Glu Leu Lys Asn Ile Thr Gly Thr Thr Gln Lys Met
                155                 160                 165 aaa aca gat agt ttt caa aga gat tat aca aaa tcc cag tca act tca         763
Lys Thr Asp Ser Phe Gln Arg Asp Tyr Thr Lys Ser Gln Ser Thr Ser
                170                 175                 180 atc acc aat gga tta caa tta gga ttt aaa gtt tca gct aaa gga ata         811
Ile Thr Asn Gly Leu Gln Leu Gly Phe Lys Val Ser Ala Lys Gly Ile
            185                 190                 195 gtg gcc tta gcc ggt gcg gat ttt gaa gca agt gta aac tat aat tta         859
Val Ala Leu Ala Gly Ala Asp Phe Glu Ala Ser Val Asn Tyr Asn Leu
200                 205                 210                 215 tcc act acc gca act gaa acc aat aca ata tct gat aaa ttt acc gtt         907
Ser Thr Thr Ala Thr Glu Thr Asn Thr Ile Ser Asp Lys Phe Thr Val
                220                 225                 230 cct tca caa gaa gtc aca tta gcg cca gga cat aag gcg atc gta aaa         955
Pro Ser Gln Glu Val Thr Leu Ala Pro Gly His Lys Ala Ile Val Lys
                235                 240                 245 cat agt ttg aag aaa atg gta tac tct gga acg cat gat tta aaa gga        1003
His Ser Leu Lys Lys Met Val Tyr Ser Gly Thr His Asp Leu Lys Gly
            250                 255                 260 gat tta aca att act ttt aat gat aag gat tta gtt caa aaa ttt att        1051
Asp Leu Thr Ile Thr Phe Asn Asp Lys Asp Leu Val Gln Lys Phe Ile
265                 270                 275 tat cca aat tat aaa gct att gat tta tct aat att cgt aaa gca atg        1099
Tyr Pro Asn Tyr Lys Ala Ile Asp Leu Ser Asn Ile Arg Lys Ala Met
280                 285                 290                 295 aca gaa att gat gaa tgg aat cat gta aaa cct acc gat ttc tat caa        1147
Thr Glu Ile Asp Glu Trp Asn His Val Lys Pro Thr Asp Phe Tyr Gln
                300                 305                 310
```

-continued

```
tta gtt ggg aat aaa aat tat ata aaa aac ggg gac act tta tac atc      1195
Leu Val Gly Asn Lys Asn Tyr Ile Lys Asn Gly Asp Thr Leu Tyr Ile
            315                 320                 325 gaa aca cct gct aaa ttc act ttg aat gga ggc aac cct tat tat aca      1243
Glu Thr Pro Ala Lys Phe Thr Leu Asn Gly Gly Asn Pro Tyr Tyr Thr
        330                 335                 340 gca acc ttt acg gaa tat gat gaa aat gga aat caa gtc aaa aca aag      1291
Ala Thr Phe Thr Glu Tyr Asp Glu Asn Gly Asn Gln Val Lys Thr Lys
    345                 350                 355 cgt tta aat aac aaa taagttactt aaaggtaatt cattaacaat gtatccatta      1346
Arg Leu Asn Asn Lys
360 tataattaat ttataaaaat aatgttttaa aa                                  1378

<210> SEQ ID NO 10
<211> LENGTH: 364
<212> TYPE: PRT
<213> ORGANISM: Bacillus thuringiensis

<400> SEQUENCE: 10

Met Lys Tyr Lys Ser Ser Lys Val Ala Met Cys Thr Leu Ser Ala Leu
1               5                   10                  15

Met Leu Ser Thr Ile Ala Thr Pro Ser Ile Ser Val Phe Ala Ala Glu
            20                  25                  30

Thr Thr Ser Ser His Ala Val Thr Asn Gln Gln Thr Ile Thr Gln Arg
        35                  40                  45

Ala Glu Ser Tyr Ile Asp Ile Val His Asn Arg Met Lys Gln Arg Asp
    50                  55                  60

Ile Glu Ser Lys Met Thr Gly Lys Ser Ile Asn Met Gln Glu Gln Ile
65                  70                  75                  80

Ile Asp Gly Trp Phe Leu Ala Arg Phe Trp Ile Phe Lys Asp Gln Asn
                85                  90                  95

Asn Ser His Gln Thr Asn Arg Phe Ile Ser Trp Phe Lys Asp Asn Leu
            100                 105                 110

Ala Ser Pro Gly Gly Tyr Asp Ser Ile Ala Glu Gln Met Gly Leu Lys
        115                 120                 125

Val Ala Ala Leu Asn Asp Met Asp Ile Ser Asn Val Asn Tyr Thr Ser
    130                 135                 140

Lys Thr Gly Asp Thr Ile Tyr Asn Gly Val Ser Glu Leu Lys Asn Ile
145                 150                 155                 160

Thr Gly Thr Thr Gln Lys Met Lys Thr Asp Ser Phe Gln Arg Asp Tyr
                165                 170                 175

Thr Lys Ser Gln Ser Thr Ser Ile Thr Asn Gly Leu Gln Leu Gly Phe
            180                 185                 190

Lys Val Ser Ala Lys Gly Ile Val Ala Leu Ala Gly Ala Asp Phe Glu
        195                 200                 205

Ala Ser Val Asn Tyr Asn Leu Ser Thr Thr Ala Thr Glu Thr Asn Thr
    210                 215                 220

Ile Ser Asp Lys Phe Thr Val Pro Ser Gln Glu Val Thr Leu Ala Pro
225                 230                 235                 240

Gly His Lys Ala Ile Val Lys His Ser Leu Lys Lys Met Val Tyr Ser
                245                 250                 255

Gly Thr His Asp Leu Lys Gly Asp Leu Thr Ile Thr Phe Asn Asp Lys
            260                 265                 270

Asp Leu Val Gln Lys Phe Ile Tyr Pro Asn Tyr Lys Ala Ile Asp Leu
```

```
        275                 280                 285

Ser Asn Ile Arg Lys Ala Met Thr Glu Ile Asp Glu Trp Asn His Val
    290                 295                 300

Lys Pro Thr Asp Phe Tyr Gln Leu Val Gly Asn Lys Asn Tyr Ile Lys
305                 310                 315                 320

Asn Gly Asp Thr Leu Tyr Ile Glu Thr Pro Ala Lys Phe Thr Leu Asn
                325                 330                 335

Gly Gly Asn Pro Tyr Tyr Thr Ala Thr Phe Thr Glu Tyr Asp Glu Asn
            340                 345                 350

Gly Asn Gln Val Lys Thr Lys Arg Leu Asn Asn Lys
        355                 360

<210> SEQ ID NO 11
<211> LENGTH: 21
<212> TYPE: DNA
<213> ORGANISM: Artificial Sequence
<220> FEATURE:
<223> OTHER INFORMATION: probe sequence, or amplification primer
      sequence for use with primer as set forth in SEQ ID NO 12,
      corresponding to CDS as set forth in SEQ ID NO 3 from 438-458,
      biased toward codons preferred in Bacillus species genes
      containing A or T in 3rd position

<400> SEQUENCE: 11
aataataatc atcaaacwaa t                                                21

<210> SEQ ID NO 12
<211> LENGTH: 21
<212> TYPE: DNA
<213> ORGANISM: Artificial Sequence
<220> FEATURE:
<223> OTHER INFORMATION: probe sequence, or amplification primer
      sequence for use with SEQ ID NO 11 corresponding to SEQ ID NO 3
      from nucleotide position 978- 998, biased toward codons preferred
      in Bacillus species genes in which A or T is in 3rd position

<400> SEQUENCE: 12
attwggataw ataaattttt g                                                21

<210> SEQ ID NO 13
<211> LENGTH: 1101
<212> TYPE: DNA
<213> ORGANISM: Artificial Sequence
<220> FEATURE:
<223> OTHER INFORMATION: coding sequence preferred for use in monocot
      species encoding a Bt TIC901 amino acid sequence variant
<220> FEATURE:
<221> NAME/KEY: CDS
<222> LOCATION: (1)..(1101)
<223> OTHER INFORMATION:

<400> SEQUENCE: 13 atg aag aac cgc ttc agc aag gtc gcc ctc tgc acg gtg cct atc ctc       48
Met Lys Asn Arg Phe Ser Lys Val Ala Leu Cys Thr Val Pro Ile Leu
1               5                   10                  15 atg gtt tct acg ttc gcg tcc agc tcg atg tcc gcg ttc gca gcg gag       96
Met Val Ser Thr Phe Ala Ser Ser Ser Met Ser Ala Phe Ala Ala Glu
            20                  25                  30 gcc aaa agt cct gac ttg aac gtg tcc caa cag gtc ata ggc cct tac      144
Ala Lys Ser Pro Asp Leu Asn Val Ser Gln Gln Val Ile Gly Pro Tyr
        35                  40                  45 gca gaa tct tac atc gac atc gtc cag gac aga atg aag cag aga gac      192
Ala Glu Ser Tyr Ile Asp Ile Val Gln Asp Arg Met Lys Gln Arg Asp
    50                  55                  60
```

```
aaa gga tcc aaa ctc act ggc aaa ccc atc aac atg caa gag cag atc     240
Lys Gly Ser Lys Leu Thr Gly Lys Pro Ile Asn Met Gln Glu Gln Ile
 65                  70                  75                  80 atc gat ggg tgg ttt ctc gca cga ttc tgg att ttc aag gat cag aac     288
Ile Asp Gly Trp Phe Leu Ala Arg Phe Trp Ile Phe Lys Asp Gln Asn
                 85                  90                  95 aat aac cac cag aca aac agg ttc atc tca tgg ttt aag gat aac atc     336
Asn Asn His Gln Thr Asn Arg Phe Ile Ser Trp Phe Lys Asp Asn Ile
            100                 105                 110 gcc tca tct aag gga tac aac tca ata gcc gaa cag atg ggc ctc aaa     384
Ala Ser Ser Lys Gly Tyr Asn Ser Ile Ala Glu Gln Met Gly Leu Lys
        115                 120                 125 atc gaa gca gag aat gat atg gac gtg aca aat atc gac tac act agt     432
Ile Glu Ala Glu Asn Asp Met Asp Val Thr Asn Ile Asp Tyr Thr Ser
130                 135                 140 aag acc gga gac aca atc tac aac ggc att tcg gaa ctt aaa aac tat     480
Lys Thr Gly Asp Thr Ile Tyr Asn Gly Ile Ser Glu Leu Lys Asn Tyr
145                 150                 155                 160 acg ggc agc acc cag aaa atg aag acc gat agc ttt caa agg gac tac     528
Thr Gly Ser Thr Gln Lys Met Lys Thr Asp Ser Phe Gln Arg Asp Tyr
                165                 170                 175 aca aaa tcc gag tcg acc tcc gtg acc aat ggc ctc cag ctg ggc ttc     576
Thr Lys Ser Glu Ser Thr Ser Val Thr Asn Gly Leu Gln Leu Gly Phe
            180                 185                 190 aag gtg gca gca aag ggc gtc gtc gct tta gcc ggc gca gac ttc gag     624
Lys Val Ala Ala Lys Gly Val Val Ala Leu Ala Gly Ala Asp Phe Glu
        195                 200                 205 act tcg gtg acc tac aat ctg tct aca act acg act gag acg aac aca     672
Thr Ser Val Thr Tyr Asn Leu Ser Thr Thr Thr Thr Glu Thr Asn Thr
210                 215                 220 att tcc gac aag ttt acg gtt ccg tct cag gag gtt acg ttc cct cca     720
Ile Ser Asp Lys Phe Thr Val Pro Ser Gln Glu Val Thr Phe Pro Pro
225                 230                 235                 240 ggc cac aag gca atc gtc aag cac gac ctg agg aaa atg gtc tac agc     768
Gly His Lys Ala Ile Val Lys His Asp Leu Arg Lys Met Val Tyr Ser
                245                 250                 255 ggc acc cat gat ctc aaa ggc gac ctc atc gtg tcg ttc aac gac aag     816
Gly Thr His Asp Leu Lys Gly Asp Leu Ile Val Ser Phe Asn Asp Lys
            260                 265                 270 gag ata gtc cag aag ttc atc tac cca aat tac cgc gac atc aac ctc     864
Glu Ile Val Gln Lys Phe Ile Tyr Pro Asn Tyr Arg Asp Ile Asn Leu
        275                 280                 285 agt gac atc cga gag acc atg atc gag atc gac gag tgg aac cac gtg     912
Ser Asp Ile Arg Glu Thr Met Ile Glu Ile Asp Glu Trp Asn His Val
290                 295                 300 aac cct gtc aat ttc tac gaa ctc gta gga gtt aag aac cac atc aag     960
Asn Pro Val Asn Phe Tyr Glu Leu Val Gly Val Lys Asn His Ile Lys
305                 310                 315                 320 aac ggt gaa aca ttg tac atc gac acg ccg gct aag ttc atg ttc aac    1008
Asn Gly Glu Thr Leu Tyr Ile Asp Thr Pro Ala Lys Phe Met Phe Asn
                325                 330                 335 gga gcg aat cct tac tat cga gct acc ttc acg gag tac gat ggc aac    1056
Gly Ala Asn Pro Tyr Tyr Arg Ala Thr Phe Thr Glu Tyr Asp Gly Asn
            340                 345                 350 aac aat cct gtt cag acc aag gtg ttg agt gag aat ttc aag ctg        1101
Asn Asn Pro Val Gln Thr Lys Val Leu Ser Glu Asn Phe Lys Leu
        355                 360                 365

<210> SEQ ID NO 14
<211> LENGTH: 367
```

```
<212> TYPE: PRT
<213> ORGANISM: Artificial Sequence
<220> FEATURE:
<223> OTHER INFORMATION: coding sequence preferred for use in monocot
      species encoding a Bt TIC901 amino acid sequence variant

<400> SEQUENCE: 14
```

| | | | | | | | | | | | | | | |
|---

```
<210> SEQ ID NO 15
<211> LENGTH: 23
<212> TYPE: DNA
<213> ORGANISM: Artificial Sequence
<220> FEATURE:
<223> OTHER INFORMATION: oligonucleotide primer coupled with prJPW152
      SEQ ID NO 16 in thermal amplification reactions

<400> SEQUENCE: 15
cctttggcag aaactttaac tcc                                              23

<210> SEQ ID NO 16
<211> LENGTH: 21
<212> TYPE: DNA
<213> ORGANISM: Artificial Sequence
<220> FEATURE:
<223> OTHER INFORMATION: oligonucleotide primer coupled with prJPW151
      SEQ ID NO 15 in thermal amplification reactions

<400> SEQUENCE: 16
gtgtattctg gtacgcatga c                                                21

<210> SEQ ID NO 17
<211> LENGTH: 34
<212> TYPE: DNA
<213> ORGANISM: Artificial Sequence
<220> FEATURE:
<223> OTHER INFORMATION: oligonucleotide primer coupled with prJPW183
      SEQ ID NO 18 in thermal amplification reactions

<400> SEQUENCE: 17
gccggatccc tagctgaata tgcagtagat aatg                                  34

<210> SEQ ID NO 18
<211> LENGTH: 25
<212> TYPE: DNA
<213> ORGANISM: Artificial Sequence
<220> FEATURE:
<223> OTHER INFORMATION: oligonucleotide primer coupled with prJPW186
      SEQ ID NO 17 in thermal amplification reactions

<400> SEQUENCE: 18
gtggcacgtt tataggccat tgttc                                            25

<210> SEQ ID NO 19
<211> LENGTH: 23
<212> TYPE: DNA
<213> ORGANISM: Artificial Sequence
<220> FEATURE:
<223> OTHER INFORMATION: oligonucleotide primer coupled with prJPW156
      SEQ ID NO 20 in thermal amplification reactions

<400> SEQUENCE: 19
cttttaggcc catctgttca gcg                                              23

<210> SEQ ID NO 20
<211> LENGTH: 26
<212> TYPE: DNA
<213> ORGANISM: Artificial Sequence
<220> FEATURE:
<223> OTHER INFORMATION: oligonucleotide primer coupled with prJPW155
      SEQ ID NO 19 in thermal amplification reactions

<400> SEQUENCE: 20
gccttagccg gtgcggattt tgaagc                                           26

<210> SEQ ID NO 21
<211> LENGTH: 44
```

<212> TYPE: DNA
<213> ORGANISM: Artificial Sequence
<220> FEATURE:
<223> OTHER INFORMATION: oligonucleotide primer coupled with prJPW170
      SEQ ID NO 22 in thermal amplification reactions

<400> SEQUENCE: 21
ggagcttatt tgttatttaa acgctttgtt ttgacttgat ttcc                44

<210> SEQ ID NO 22
<211> LENGTH: 39
<212> TYPE: DNA
<213> ORGANISM: Artificial Sequence
<220> FEATURE:
<223> OTHER INFORMATION: oligonucleotide primer coupled with prJPW168
      SEQ ID NO 21 in thermal amplification reactions

<400> SEQUENCE: 22
gccggatccc agtggatagg aatttgtttt cgtgctagg                       39

<210> SEQ ID NO 23
<211> LENGTH: 26
<212> TYPE: DNA
<213> ORGANISM: Artificial Sequence
<220> FEATURE:
<223> OTHER INFORMATION: universal forward amplification primer similar
      to SEQ ID NO:24 and SEQ ID NO:25 that, when used in a thermal
      amplification reaction with any of SEQ ID NO:SEQ ID NO:27-29 and
      template DNA homologous to tic901, 1201, 407, 417, or 431 and the
      like result in amplicon of from about 600 to about 650 base pairs

<400> SEQUENCE: 23
aayatgcarg arcarathat hgaygg                                     26

<210> SEQ ID NO 24
<211> LENGTH: 23
<212> TYPE: DNA
<213> ORGANISM: Artificial Sequence
<220> FEATURE:
<223> OTHER INFORMATION: universal forward amplification primer similar
      to SEQ ID NO:23 and SEQ ID NO:25 that, when used in a thermal
      amplification reaction with any of SEQ ID NO:27-29 and template
      DNA homologous to tic901, 1201, 407, 417, or 431 and the like
      result in amplicon of from about 600 to about 650 base pairs

<400> SEQUENCE: 24
aayatgcarg arcarathat hga                                        23

<210> SEQ ID NO 25
<211> LENGTH: 20
<212> TYPE: DNA
<213> ORGANISM: Artificial Sequence
<220> FEATURE:
<223> OTHER INFORMATION: universal forward amplification primer similar
      to SEQ ID NO:23 and SEQ ID NO:24 that, when used in a thermal
      amplification reaction with any of SEQ ID NO:27-29 and template
      DNA homologous to tic901, 1201, 407, 417, or 431 and the like
      result in amplicon of from about 600 to about 650 base pairs

<400> SEQUENCE: 25
aayatgcarg arcarathat                                            20

<210> SEQ ID NO 26
<211> LENGTH: 20
<212> TYPE: DNA
<213> ORGANISM: Artificial Sequence
<220> FEATURE:
<223> OTHER INFORMATION: universal forward amplification primer that,
      when used in a thermal amplification reaction with any of SEQ ID

```
        NO:27-29 and template DNA homologous to tic901, 1201, 407, 417,
        431 and the like result in amplicon of from about 395 to about
        425 base pairs
<220> FEATURE:
<221> NAME/KEY: misc_feature
<222> LOCATION: (3)..(3)
<223> OTHER INFORMATION: inosine
<220> FEATURE:
<221> NAME/KEY: misc_feature
<222> LOCATION: (9)..(9)
<223> OTHER INFORMATION: inosine

<400> SEQUENCE: 26
ggngayacna thtayaaygg                                                   20

<210> SEQ ID NO 27
<211> LENGTH: 26
<212> TYPE: DNA
<213> ORGANISM: Artificial Sequence
<220> FEATURE:
<223> OTHER INFORMATION: universal reverse amplification primer similar
        to SEQ ID NO:28 and SEQ ID NO:29
<220> FEATURE:
<221> NAME/KEY: misc_feature
<222> LOCATION: (6)..(6)
<223> OTHER INFORMATION: inosine
<220> FEATURE:
<221> NAME/KEY: misc_feature
<222> LOCATION: (24)..(24)
<223> OTHER INFORMATION: inosine

<400> SEQUENCE: 27
tarttnggrt adatraaytt ytgnac                                            26

<210> SEQ ID NO 28
<211> LENGTH: 23
<212> TYPE: DNA
<213> ORGANISM: Artificial Sequence
<220> FEATURE:
<223> OTHER INFORMATION: universal reverse amplification primer similar
        to SEQ ID NO:27 and SEQ ID NO:29
<220> FEATURE:
<221> NAME/KEY: misc_feature
<222> LOCATION: (6)..(6)
<223> OTHER INFORMATION: inosine

<400> SEQUENCE: 28
tarttnggrt adatraaytt ytg                                               23

<210> SEQ ID NO 29
<211> LENGTH: 20
<212> TYPE: DNA
<213> ORGANISM: Artificial Sequence
<220> FEATURE:
<223> OTHER INFORMATION: universal reverse amplification primer similar
        to SEQ ID NO:27 and SEQ ID NO:28
<220> FEATURE:
<221> NAME/KEY: misc_feature
<222> LOCATION: (18)..(18)
<223> OTHER INFORMATION: inosine

<400> SEQUENCE: 29
ggrtadatra ayttytgnac                                                   20

<210> SEQ ID NO 30
<211> LENGTH: 570
<212> TYPE: DNA
<213> ORGANISM: Bacillus thuringiensis
<220> FEATURE:
<221> NAME/KEY: CDS
<222> LOCATION: (1)..(570)
```

<223> OTHER INFORMATION:

<400> SEQUENCE: 30

```
ttt tta gct aga ttt tgg ata ttt gag g

```
                   100                 105                 110
Lys Gly Val Val Ala Leu Ala Gly Ala Asp Phe Glu Thr Ser Val Thr
            115                 120                 125

Tyr Asn Leu Ser Thr Thr Thr Glu Thr Asn Thr Ile Ser Asp Lys
        130                 135                 140

Phe Thr Val Pro Ser Gln Glu Val Thr Leu Pro Pro Gly His Lys Ala
145                 150                 155                 160

Ile Val Lys His Asp Leu Arg Lys Met Val Tyr Ser Gly Thr His Asp
                165                 170                 175

Leu Lys Gly Asp Leu Ile Val Ser Phe Asn Asp Lys Glu Ile
            180                 185                 190

<210> SEQ ID NO 32
<211> LENGTH: 1095
<212> TYPE: DNA
<213> ORGANISM: Bacillus thuringiensis
<220> FEATURE:
<221> NAME/KEY: CDS
<222> LOCATION: (1)..(1092)
<223> OTHER INFORMATION: sequence encoding TIC431 precursor amino acid
      sequence

<400> SEQUENCE: 32 atg aaa tac aag tct tca aaa gta gca atg tgt aca tta tcg gct tta        48
Met Lys Tyr Lys Ser Ser Lys Val Ala Met Cys Thr Leu Ser Ala Leu
1               5                   10                  15 atg ctt tcg aca atc gcc act cca agt ata tct gtt tcc gct gct gaa       96
Met Leu Ser Thr Ile Ala Thr Pro Ser Ile Ser Val Phe Ala Ala Glu
                20                  25                  30 aca act gca tca cat aag gtt act aat cag caa aca att gca cag cgt      144
Thr Thr Ala Ser His Lys Val Thr Asn Gln Gln Thr Ile Ala Gln Arg
            35                  40                  45 gca gaa tct tat atc gat att gtg cat aat aga atg aaa aaa cga gat      192
Ala Glu Ser Tyr Ile Asp Ile Val His Asn Arg Met Lys Lys Arg Asp
        50                  55                  60 att gaa tca aaa atg aca ggt aaa cct att aat atg caa gaa caa ata      240
Ile Glu Ser Lys Met Thr Gly Lys Pro Ile Asn Met Gln Glu Gln Ile
65                  70                  75                  80 att gat gga tgg ttt tta gct aga ttt tgg ata ttc aag gac caa aat      288
Ile Asp Gly Trp Phe Leu Ala Arg Phe Trp Ile Phe Lys Asp Gln Asn
                85                  90                  95 aat agt cac caa aca aat aga ttt att tca tgg ttt aaa gat aat tta      336
Asn Ser His Gln Thr Asn Arg Phe Ile Ser Trp Phe Lys Asp Asn Leu
            100                 105                 110 gct agt cca gga ggg tat aat agt atc gct aaa caa atg ggg tta aaa      384
Ala Ser Pro Gly Gly Tyr Asn Ser Ile Ala Lys Gln Met Gly Leu Lys
        115                 120                 125 ata gaa gta tta aat gat atg gat ata tca aat gta aat tat act tct      432
Ile Glu Val Leu Asn Asp Met Asp Ile Ser Asn Val Asn Tyr Thr Ser
130                 135                 140 aag aca ggg gat act ata tat aat ggt gtt tcc gaa tta aaa aat atc      480
Lys Thr Gly Asp Thr Ile Tyr Asn Gly Val Ser Glu Leu Lys Asn Ile
145                 150                 155                 160 aca ggt aca act caa aaa atg aaa aca gat agt ttt caa aga gat tat      528
Thr Gly Thr Thr Gln Lys Met Lys Thr Asp Ser Phe Gln Arg Asp Tyr
                165                 170                 175 aca aaa tca cag tca act tca atc acc aat gga tta caa tta gga ttt      576
Thr Lys Ser Gln Ser Thr Ser Ile Thr Asn Gly Leu Gln Leu Gly Phe
            180                 185                 190 aaa gtt tct gcc aaa ggg gtg ata gct tta gca gga gca gac ttc gaa      624
Lys Val Ser Ala Lys Gly Val Ile Ala Leu Ala Gly Ala Asp Phe Glu
```

```
Lys Val Ser Ala Lys Gly Val Ile Ala Leu Ala Gly Ala Asp Phe Glu
            195                 200                 205 gca agt gtc aac tat aat tta tcc act acc gca act gaa acc aat ata        672
Ala Ser Val Asn Tyr Asn Leu Ser Thr Thr Ala Thr Glu Thr Asn Ile
210                 215                 220 ata tct gat aaa ttt acc gtt cct tca caa gaa gtt aca tta gcg cca        720
Ile Ser Asp Lys Phe Thr Val Pro Ser Gln Glu Val Thr Leu Ala Pro
225                 230                 235                 240 gga cat aag gcg atc gta aaa cat agt tta aag aaa atg gta tac tcc        768
Gly His Lys Ala Ile Val Lys His Ser Leu Lys Lys Met Val Tyr Ser
            245                 250                 255 gga acg cat gat tta aaa gga gat tta aca att act ttt aat gat aag        816
Gly Thr His Asp Leu Lys Gly Asp Leu Thr Ile Thr Phe Asn Asp Lys
            260                 265                 270 gat tta gtt caa aaa ttt att tat cca aat tat aaa gct att gat tta        864
Asp Leu Val Gln Lys Phe Ile Tyr Pro Asn Tyr Lys Ala Ile Asp Leu
            275                 280                 285 tct aat att cgt aaa gca ctg act gaa att gat gaa tgg aat cat gta        912
Ser Asn Ile Arg Lys Ala Leu Thr Glu Ile Asp Glu Trp Asn His Val
290                 295                 300 aaa cct acc gat ttc tat caa tta gtt ggg aac aaa aat tat ata aaa        960
Lys Pro Thr Asp Phe Tyr Gln Leu Val Gly Asn Lys Asn Tyr Ile Lys
305                 310                 315                 320 aac ggg gac act tta tac atc gaa aca cct gct aaa ttc act ttg aat       1008
Asn Gly Asp Thr Leu Tyr Ile Glu Thr Pro Ala Lys Phe Thr Leu Asn
            325                 330                 335 gga gga aac cct tat tat aca gca acc ttt acg gaa tat gat gaa agt       1056
Gly Gly Asn Pro Tyr Tyr Thr Ala Thr Phe Thr Glu Tyr Asp Glu Ser
            340                 345                 350 gga aat caa gtc aaa aca aag cat tta agt gtc aaa taa                    1095
Gly Asn Gln Val Lys Thr Lys His Leu Ser Val Lys
            355                 360

<210> SEQ ID NO 33
<211> LENGTH: 364
<212> TYPE: PRT
<213> ORGANISM: Bacillus thuringiensis

<400> SEQUENCE: 33

Met Lys Tyr Lys Ser Ser Lys Val Ala Met Cys Thr Leu Ser Ala Leu
1               5                   10                  15

Met Leu Ser Thr Ile Ala Thr Pro Ser Ile Ser Val Phe Ala Ala Glu
                20                  25                  30

Thr Thr Ala Ser His Lys Val Thr Asn Gln Gln Thr Ile Ala Gln Arg
            35                  40                  45

Ala Glu Ser Tyr Ile Asp Ile Val His Asn Arg Met Lys Lys Arg Asp
        50                  55                  60

Ile Glu Ser Lys Met Thr Gly Lys Pro Ile Asn Met Gln Glu Gln Ile
65                  70                  75                  80

Ile Asp Gly Trp Phe Leu Ala Arg Phe Trp Ile Phe Lys Asp Gln Asn
                85                  90                  95

Asn Ser His Gln Thr Asn Arg Phe Ile Ser Trp Phe Lys Asp Asn Leu
            100                 105                 110

Ala Ser Pro Gly Gly Tyr Asn Ser Ile Ala Lys Gln Met Gly Leu Lys
        115                 120                 125

Ile Glu Val Leu Asn Asp Met Asp Ile Ser Asn Val Asn Tyr Thr Ser
    130                 135                 140

Lys Thr Gly Asp Thr Ile Tyr Asn Gly Val Ser Glu Leu Lys Asn Ile
```

-continued

```
145                 150                 155                 160
Thr Gly Thr Thr Gln Lys Met Lys Thr Asp Ser Phe Gln Arg Asp Tyr
                165                 170                 175
Thr Lys Ser Gln Ser Thr Ser Ile Thr Asn Gly Leu Gln Leu Gly Phe
            180                 185                 190

Lys Val Ser Ala Lys Gly Val Ile Ala Leu Ala Gly Ala Asp Phe Glu
        195                 200                 205

Ala Ser Val Asn Tyr Asn Leu Ser Thr Thr Ala Thr Glu Thr Asn Ile
    210                 215                 220

Ile Ser Asp Lys Phe Thr Val Pro Ser Gln Glu Val Thr Leu Ala Pro
225                 230                 235                 240
Gly His Lys Ala Ile Val Lys His Ser Leu Lys Lys Met Val Tyr Ser
                245                 250                 255
Gly Thr His Asp Leu Lys Gly Asp Leu Thr Ile Thr Phe Asn Asp Lys
            260                 265                 270

Asp Leu Val Gln Lys Phe Ile Tyr Pro Asn Tyr Lys Ala Ile Asp Leu
        275                 280                 285

Ser Asn Ile Arg Lys Ala Leu Thr Glu Ile Asp Glu Trp Asn His Val
    290                 295                 300

Lys Pro Thr Asp Phe Tyr Gln Leu Val Gly Asn Lys Asn Tyr Ile Lys
305                 310                 315                 320
Asn Gly Asp Thr Leu Tyr Ile Glu Thr Pro Ala Lys Phe Thr Leu Asn
                325                 330                 335
Gly Gly Asn Pro Tyr Tyr Thr Ala Thr Phe Thr Glu Tyr Asp Glu Ser
            340                 345                 350

Gly Asn Gln Val Lys Thr Lys His Leu Ser Val Lys
        355                 360
```

What is claimed is:

1. A DNA construct comprising a polynucleotide operably linked to a heterologous promoter, said polynucleotide encoding a secreted *Bacillus thuringiensis* insecticidal protein toxic to a coleopteran insect pest, wherein said protein comprises an amino acid sequence at least 95% identical to SEQ ID NO:6 from amino acid positions 44-364.

2. The DNA construct of claim 1, wherein said coleopteran insect pest is selected from the group consisting of a corn rootworm and a Colorado potato beetle.

3. The DNA construct of claim 2, wherein said corn rootworm is selected from the group consisting of a western corn rootworm, a southern corn rootworm, or a northern corn rootworm.

4. The DNA construct of claim 1, comprising the nucleotide sequence as set forth in SEQ ID NO:5.

5. The DNA construct of claim 1, comprising a nucleotide sequence modified from SEQ ID NO:5 for use in plants.

6. A host cell transformed to contain the DNA construct of claim 1.

7. The host cell of claim 6, wherein said host cell is a plant cell.

8. A method for detecting a polynucleotide from a *Bacillus* species encoding an insecticidal protein in a sample, said protein exhibiting an amino acid sequence at least 95% identical to SEQ ID NO:6 from amino acid positions 44-364, said method comprising:

(a) constructing a probe that hybridizes to the nucleotide sequence as set forth in SEQ ID NO:5 (tic1201) or the complement thereof under stringent hybridization conditions;

(b) subjecting said probe and sample to stringent hybridization conditions, wherein detection of hybridization of said probe to said sample is indicative of presence of said polynucleotide in said sample.

9. The host cell of claim 7, wherein said host cell is selected from the group consisting of a monocot plant cell and a dicot plant cell.

10. The host cell of claim 9, wherein said monocot plant cell is selected from the group consisting of a corn plant cell, a wheat plant cell, a rice plant cell, an oat plant cell, an onion plant cell, and a grass plant cell.

11. The host cell of claim 9, wherein said dicot plant cell is selected from the group consisting of a cotton plant cell, a canola plant cell, a soybean plant cell, a fruit tree plant cell, an okra plant cell, a pepper plant cell, an ornamental plant cell, a sunflower plant cell, a cucurbit plant cell, and a melon plant cell.

* * * * *